(12) United States Patent
Cali et al.

(10) Patent No.: US 11,672,702 B2
(45) Date of Patent: Jun. 13, 2023

(54) METHOD AND APPARATUS FOR IMPLANT IN THE CONVENTIONAL AQUEOUS HUMOR OUTFLOW PATHWAY OF A MAMMALIAN EYE

(71) Applicant: eyeFlow, Inc., Mission Viejo, CA (US)

(72) Inventors: Douglas Cali, Mission Viejo, CA (US); David Dean Richardson, Pasadena, CA (US)

(73) Assignee: eyeFlow, Inc., Mission Viejo, CA (US)

( * ) Notice: Subject to any disclaimer, the term of this patent is extended or adjusted under 35 U.S.C. 154(b) by 0 days.

(21) Appl. No.: 17/838,066

(22) Filed: Jun. 10, 2022

(65) Prior Publication Data
US 2023/0011719 A1 Jan. 12, 2023

Related U.S. Application Data

(63) Continuation-in-part of application No. 17/610,426, filed as application No. PCT/US2020/033296 on May 15, 2020.

(51) Int. Cl.
*A61F 9/007* (2006.01)
*A61F 9/00* (2006.01)

(52) U.S. Cl.
CPC ........ *A61F 9/00781* (2013.01); *A61F 9/0017* (2013.01); *A61F 2250/0067* (2013.01)

(58) Field of Classification Search
CPC ................ A61F 9/00781; A61F 9/0017; A61F 2250/0067
See application file for complete search history.

(56) References Cited

U.S. PATENT DOCUMENTS

2008/0228127 A1* 9/2008 Burns ................ A61F 9/00781
 604/9
2013/0331760 A1* 12/2013 Grieshaber ......... A61F 9/00781
 604/8

(Continued)

FOREIGN PATENT DOCUMENTS

JP 2011513002 A 4/2011
WO 2020050968 A1 3/2020

OTHER PUBLICATIONS

International Search Report and Written Opinion for International Patent Application No. PCT/US20/33296, dated Feb. 15, 2021, 8 pages.

*Primary Examiner* — Leslie R Deak
(74) *Attorney, Agent, or Firm* — Elliott, Ostrander & Preston, P.C.

(57) ABSTRACT

An aqueous humor outflow device includes an arcuate scaffold that fits within a conventional aqueous humor outflow pathway of a mammalian eye to receive aqueous humor from a trabecular meshwork of the mammalian eye and allow flow of the aqueous humor through the arcuate scaffold to one or more collector channels that originate in a posterior wall of a Schlemm's canal. The arcuate scaffold includes a first arcuate rail, and a second arcuate rail spaced apart from, and substantially parallel to, the first arcuate rail. The first and second arcuate rails each have an anterior edge that is adjacent to the trabecular meshwork when inserted in the Schlemm's canal, and a posterior edge that is adjacent to the posterior wall of the Schlemm's canal. Structural components coupled to the first arcuate rail and the second arcuate rail maintain the respective anterior and posterior edges of the first and second arcuate rails spaced apart from, and substantially parallel to, each other.

28 Claims, 41 Drawing Sheets

(56) References Cited

U.S. PATENT DOCUMENTS

| | | |
|---|---|---|
| 2014/0276332 A1 | 9/2014 | Grimaldi et al. |
| 2015/0290033 A1* | 10/2015 | Wardle .................. A61F 9/0017 606/107 |
| 2016/0331588 A1 | 11/2016 | Ambati et al. |
| 2019/0247232 A1 | 8/2019 | Lynch et al. |
| 2023/0053897 A1 | 2/2023 | Richardson et al. |

* cited by examiner

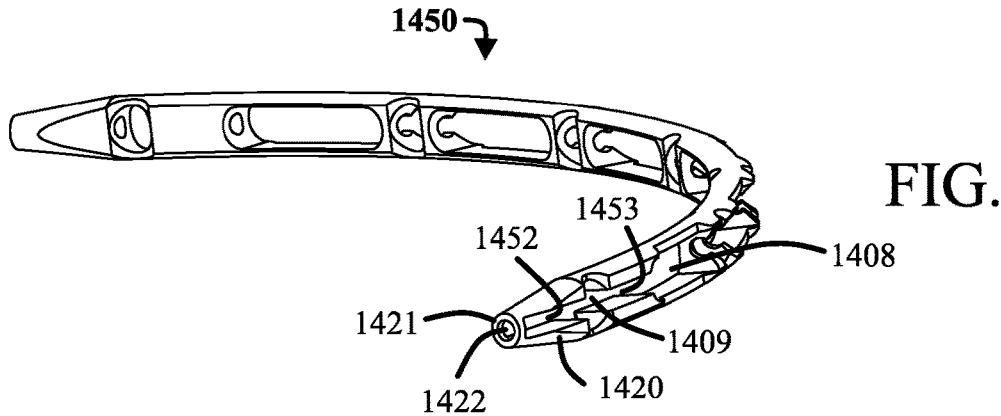
FIG. 14E
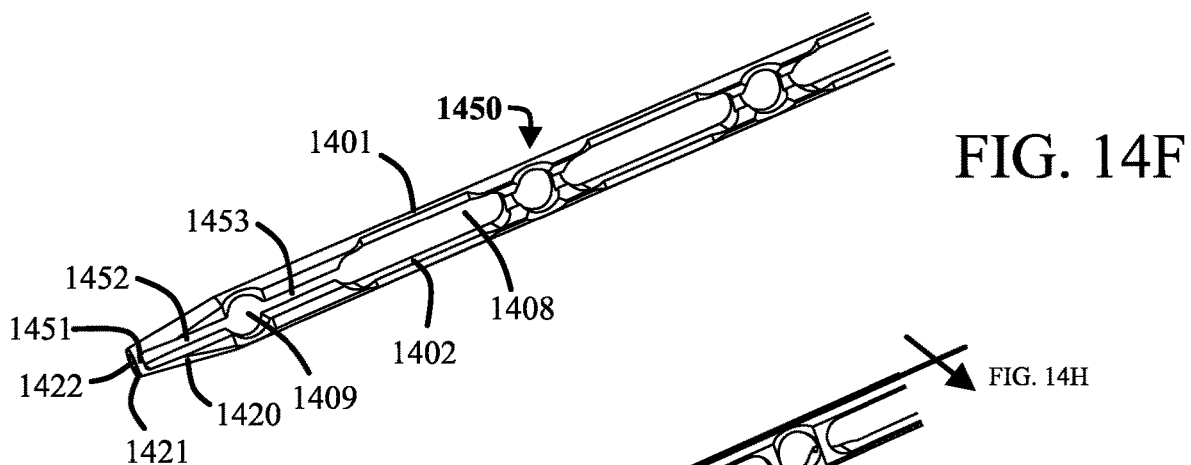
FIG. 14F
FIG. 14G
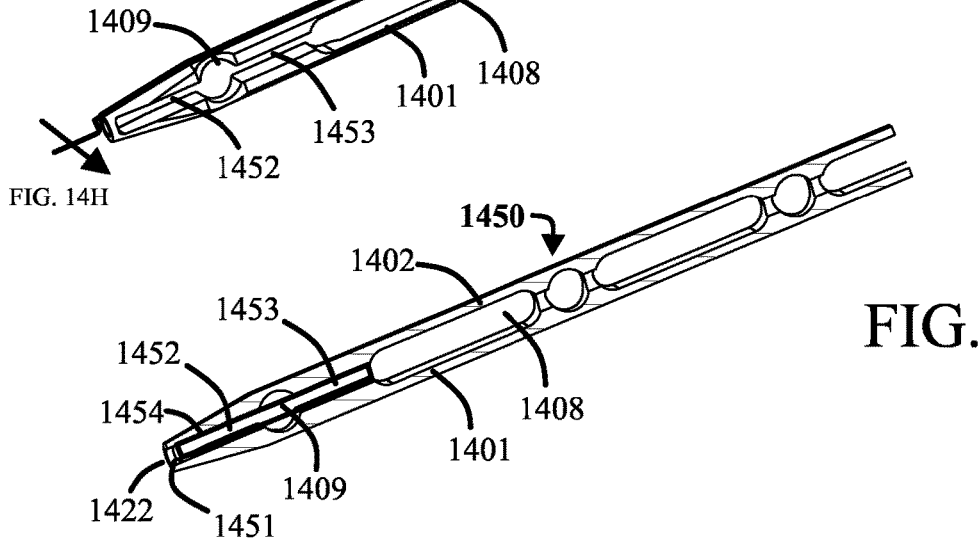
FIG. 14H

METHOD AND APPARATUS FOR IMPLANT IN THE CONVENTIONAL AQUEOUS HUMOR OUTFLOW PATHWAY OF A MAMMALIAN EYE

CROSS REFERENCE TO RELATED APPLICATIONS

This application is a continuation-in-part of U.S. patent application Ser. No. 17/610,426 filed Nov. 10, 2021, entitled "Method and Apparatus for Implant in the Conventional Aqueous Humor Outflow Pathway of a Mammalian Eye", which is a National Stage Entry of PCT Application No. PCT/US20/33296, the disclosure of which is incorporated herein by reference in its entirety.

COPYRIGHT NOTICE

This document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

Embodiments of the invention relate to a method and apparatus intended for use within the conventional aqueous humor outflow pathway of the mammalian eye.

BACKGROUND

FIGS. 1 and 2 are cross-sectional views of an anterior segment of a mammalian eye showing the basic anatomy relevant to a better understanding of the problems addressed by the various embodiments of the scaffolding device discussed herein. The internal structures of the eye are bathed in aqueous fluid which is produced by a ciliary body 101. This fluid must eventually leave the eye by various routes. A common route of exit involves movement of aqueous humor between zonules 102 (which support a lens 103) through a pupil 104, and into the anterior chamber which is defined by the space between an iris 105 and a cornea 106. That portion of the anterior chamber where the iris, a sclera (i.e., the white of the eye) 107, and cornea meet is termed the "angle". In what is termed the conventional outflow pathway, aqueous humor leaves the anterior chamber through an angle structure called a trabecular meshwork 108 which is bordered by a scleral spur 109 inferiorly, cornea 106 superiorly, and posteriorly by a Schlemm's canal 110. Aqueous humor passes through the trabecular meshwork 108 into the Schlemm's canal 110 and from there through a collector channel entrance 121 located on a posterior wall 122 of the Schlemm's canal 110 into a collector channel 123 which connects to an aqueous humor outflow vein (not pictured) from which aqueous humor may enter the larger venous blood vessels of the body. The combination of rate of aqueous fluid production, rate of aqueous fluid outflow, and elasticity of the ocular structures largely determines the intraocular pressure (IOP) of the mammalian eye.

The trabecular meshwork 108 is the point of greatest resistance to aqueous flow within the conventional outflow pathway. This resistance to flow varies according to physiologic and disease states. One structure that is known to have an effect on flow through the trabecular meshwork 108 is a ciliary body muscle 111. When the ciliary body muscle 111 contracts, the trabecular meshwork 108 is stretched, decreasing resistance to flow (i.e., increasing flow) of aqueous humor across the trabecular meshwork 108 into the Schlemm's canal 110.

The human trabecular meshwork 108 is composed of trabecular meshwork cells and a complex supporting structure made up of collagen and other molecular components called the extracellular matrix. This structure functions as a physical restrictor of aqueous humor flow out of the eye. Decades of laboratory and clinical evidence suggest that the primary cause of elevated IOP in humans with open angle glaucoma is a restriction to flow through the trabecular meshwork 108, specifically a portion of the trabecular meshwork 108 called the juxtacanalicular trabecular meshwork and the inner wall of Schlemm's canal 110, which includes a supporting structure made up primarily of collagen, called the extracellular matrix.

The amount of collagen in the extracellular matrix is not static, but rather dynamically altered by a rate of turnover. This turnover is controlled by a complex system of chemical messengers and enzymes, of which two classes of molecules appear to be of primary importance: matrix metalloproteinases (MMP) which function to degrade collagen, and tissue inhibitors of metalloproteinase (TIMP) which prevent degradation and remodeling of the extracellular matrix.

The incidence of glaucoma increases with age which is associated with an increase in the amount of collagen and other molecular components within the extracellular matrix. This leads to increased stiffness and decreased permeability of aqueous humor into Schlemm's canal 110. The trabecular meshwork 108 extracellular matrix has been shown to be markedly stiffer than that of the trabecular meshwork 108 of eyes without glaucoma. Additionally, the trabecular meshwork 108 in eyes with glaucoma varies in stiffness resulting in non-uniform resistance to flow of the aqueous humor. It makes sense, therefore, that therapies targeting the extracellular matrix (e.g., through altering the MMP/TIMP balance) hold potential as an effective treatment for glaucoma.

Laboratory studies have provided evidence of a number of potential mechanisms by which the trabecular meshwork 108 and Schlemm's canal 110 extracellular matrix might be modified. The trabecular meshwork 108 has both mechanosensing and mechanotransducing molecules which can "sense" trabecular meshwork 108 stretch as well as flow of the aqueous humor. Mechanotransducing (mechano+transducing) involves any of various mechanisms by which cells convert mechanical stimulus into electrochemical activity. This form of sensory transduction is responsible for a number of physiological processes in the body. The basic mechanism of mechanotransduction involves converting mechanical signals into electrical or chemical signals. Prolonged stretching of the trabecular meshwork 108 results in upregulation of MMPs and downregulation of TIMP (increasing permeability of the extracellular matrix and reducing resistance to aqueous humor flow). Stretching the trabecular meshwork 108 also results in release of Nitric Oxide (NO) and Vascular Endothelial Growth Factor (VEGF) by Schlemm's canal 110 endothelial cells resulting in increased outflow of aqueous humor through the drainage system and the accompanying reduction in IOP. Stretching the trabecular meshwork 108 also results in release of adenosine by the trabecular meshwork cells resulting in increased outflow of aqueous humor through the conventional aqueous humor outflow system and the accompanying reduction in IOP. Evidence of other mechanisms by which stretching of the trabecular meshwork 108 leads to regulation of aqueous humor outflow and lowering of IOP also exists. As such, a potential IOP lowering benefit could be provided by mechanisms that stretch the trabecular meshwork 108 or otherwise result in tension across its surface as occurs with pilocarpine.

The trabecular meshwork 108 also demonstrates limited elasticity and has been shown to deform under normal physiologic conditions such as accommodation and blinking. Pulsatile movement of the trabecular meshwork 108 (correlating to the cardiac cycle) is present in the normal physiologic state and this movement is hypothesized to function as a membrane-shaped piston in a fluid-displacement pump effectively pushing aqueous humor out of the Schlemm's canal 110 into the collector channels 123.

It should be noted that Schlemm's canal 110 can be thought of as a space separated from the anterior chamber by the trabecular meshwork 108. As shown in FIG. 2 Schlemm's canal 110 has a concave shaped cross-section, with the concavity defined to be generally oriented towards the anterior chamber. Schlemm's canal 110 forms a channel which enables the flow of aqueous fluid in the region of the angle of the eye and into the collector channels 123 that originate on the posterior wall 122 of Schlemm's canal 110.

If the trabecular meshwork 108 is removed (as is occasionally performed as a surgical treatment for glaucoma) the space within the Schlemm's canal 110 remains allowing direct access of aqueous fluid from the anterior chamber into the "unroofed" or exposed Schlemm's canal 110 and collector channels 123. However, removal of the trabecular meshwork 108 also destroys the trabecular meshwork dependent mechanosensing/mechanotransducing mechanisms regulating the homeostatic control of intraocular pressure. Additionally, removal of the trabecular meshwork 108 would be expected to reduce the shear stress on the Schlemm's canal endothelial cells potentially uncoupling another important intraocular pressure homeostatic control mechanism.

FIG. 3 is an enlarged cross-sectional view of an anterior chamber of an eye illustrating an angle in an eye with open angle glaucoma in which there is increased resistance of flow through the trabecular meshwork 108 into the Schlemm's canal 110 which is diminished in cross-sectional area. The trabecular meshwork 108 is collapsed onto the posterior wall 122 of the Schlemm's canal 110 limiting circumferential flow. The trabecular meshwork 108 may also herniate 108' into the collector channel entrance 121 blocking flow of aqueous humor into the collector channel 123.

FIG. 4 is an enlarged cross-sectional view of the anterior chamber of the eye of FIG. 3 illustrating the effect of pilocarpine on the angle anatomy. Pilocarpine stretches the ciliary body muscle 111, placing downward tension on the scleral spur 109, which is attached to the trabecular meshwork 108, as depicted by arrow 140. This stretches the trabecular meshwork 108 reducing resistance to flow of aqueous humor into the Schlemm's canal 110. The trabecular meshwork 108 is also pulled away from the posterior wall 122 of the Schlemm's canal 110 pulling the trabecular meshwork 108 herniation 108' out of the collector channel entrance 121, as depicted by arrow 141, resulting in flow of aqueous humor into the collector channel 123.

FIG. 5A is an overhead view of a Schlemm's canal 110 demonstrating the irregular contour of the posterior wall 122 of the Schlemm's canal 110. Rather than having a smooth, tubular vessel-like structure, the Schlemm's canal 110 has a natural configuration suggestive of a chain of irregularly shaped and sized chambers 131. As would be expected of such an irregular configuration, flow of aqueous through the Schlemm's canal 110 is non-uniform. When combined with the ocular pulse pressure, aqueous humor moves from chamber to chamber toward a collector channel entrance 121 and collector channel 123 through which aqueous humor drains into an aqueous vein (not shown) and into the general circulatory system of the body (not shown). The portions of the posterior wall 122 of Schlemm's canal 110 that separate these chambers 131 may act in a manner similar to membrane valves (i.e., diaphragm valves) 132 providing some element of directional flow of aqueous humor down a pressure gradient toward the collector channel entrance 121.

FIG. 5B is an enlarged view of a portion of the overhead view of the Schlemm's canal 110 shown in FIG. 5A showing a more detailed view of a collector channel entrance 121 and collector channel 123. Additionally, this view demonstrates how the interaction of the trabecular meshwork 108 and the posterior wall 122 of the Schlemm's canal 110 may create a membrane valve 132 functionally separating the Schlemm's canal 110 into flexible chambers 131, enabling the flexible chambers to function as a pulsatile pump moving aqueous humor from chamber to chamber.

FIG. 5C is another view of a portion of the enlarged overhead view of the Schlemm's canal 110 shown in FIG. 5B demonstrating the herniation 108' of trabecular meshwork 108 into a collector channel entrance 121 in the setting of elevated intraocular pressure (IOP). Herniation 108' of the trabecular meshwork 108 blocks the passage of aqueous humor into the collector channel 123, which may then result in further IOP elevation.

SUMMARY

An aqueous humor outflow device includes an arcuate scaffold that fits within a conventional aqueous humor outflow pathway of a mammalian eye to receive aqueous humor from a trabecular meshwork of the mammalian eye and allow flow of the aqueous humor through the arcuate scaffold to one or more collector channels that originate in a posterior wall 122 of a Schlemm's canal 110.

BRIEF DESCRIPTION OF THE DRAWINGS

Embodiments are illustrated by way of example, and not by way of limitation, and will be more fully understood with reference to the following written description when considered in connection with the figures, in which like reference numbers refer to like parts, and in which:

FIG. 14E is a perspective view of an embodiment of the aqueous humor outflow implants disclosed herein, in particular, with an alternative embodiment of an end thereof;

FIG. 14F is a posterior view of an embodiment of the aqueous humor outflow implants disclosed herein, in particular, with an alternative embodiment of an end thereof;

FIG. 14G is an anterior view of an embodiment of the aqueous humor outflow implants disclosed herein, in particular, with an alternative embodiment of an end thereof;

FIG. 14H is a cross-sectional view of an embodiment of the aqueous humor outflow implants disclosed herein, in particular, with an alternative embodiment of an end thereof;

WRITTEN DESCRIPTION

Embodiments of the invention involve a scaffolding device intended for use within the conventional aqueous humor outflow pathway of the mammalian eye. As a physical scaffold it may function to support anatomic structures, mechano-sensory, mechano-transducing, and associated homeostatic physiologic feedback loops either known or hypothesized to regulate outflow of aqueous humor from the eye. The scaffolding device may also function to support secondary implants or devices that may have diagnostic or therapeutic functions either related or unrelated to the regulation of aqueous humor outflow. Embodiments of the invention are described in enabling detail in the following examples.

Figure 6A:
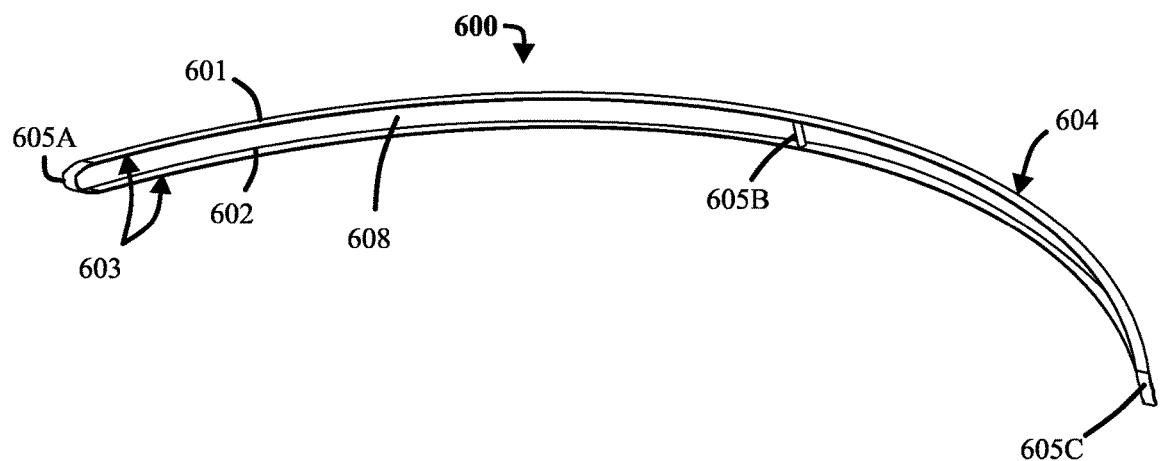
FIG. 6A is an anterior perspective view of an embodiment of the aqueous humor outflow implants disclosed herein.
Figure 6B:
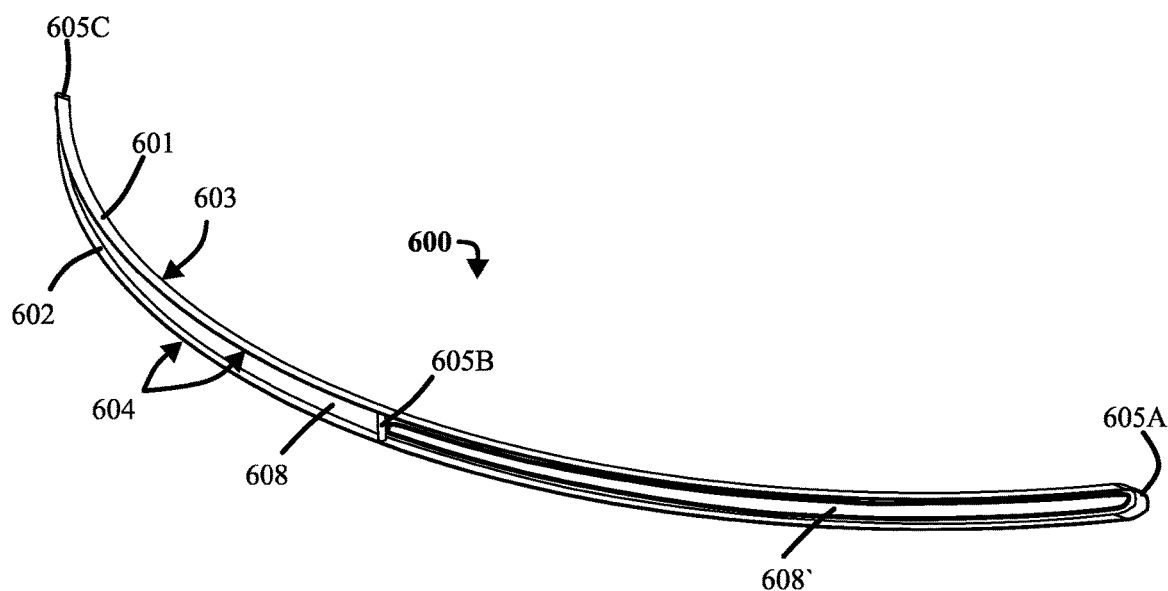
FIG. 6B is a posterior perspective view of an embodiment of the aqueous humor outflow implants disclosed herein.

FIG. 6A is an anterior perspective view of an embodiment 600 of one of the aqueous humor outflow implant devices disclosed herein. FIG. 6B is a posterior perspective view of the embodiment 600 of the aqueous humor outflow implant devices disclosed herein.

The embodiment 600 of the aqueous humor outflow implant device comprises an arcuate scaffold, shaped like a bow or curved, and sized in terms of length and cross sectional area to fit within a conventional aqueous humor outflow pathway, including a trabecular meshwork 108, a Schlemm's canal 110, collector channels, and aqueous veins of a mammalian eye. According to one embodiment, the aqueous humor outflow device is capable of fully fitting with the conventional aqueous humor outflow pathway. There are a number of reasons why fitting the aqueous humor outflow device fully within the conventional aqueous humor outflow pathway are advantageous, including prevention of endothelial cell loss, prevention of iris incarceration into implant openings, and the ease of positioning the aqueous humor outflow device (i.e., it is not necessary to estimate the "right amount" of extension into the anterior chamber as is necessary with trabecular microbypass devices).

According to other embodiments, the aqueous humor outflow device may only partially fit within the conventional aqueous humor outflow pathway, for example, in embodiments in which a portion of the device is intentionally positioned with the supracillary or suprachoroidal space or the sclera, in order to take advantage of non-conventional aqueous humor outflow pathways.

The device, when inserted within the conventional aqueous humor outflow pathway, receives aqueous humor from the trabecular meshwork 108 of the mammalian eye and allows flow of the aqueous humor through the space defined by the arcuate scaffold to one or more collector channels 123 that originate in a posterior wall 122 of the Schlemm's canal 110. With reference to FIGS. 6A and 6B, the arcuate scaffold comprises a first (i.e., a top, or a superior) arcuate rail 601, and a second (i.e., a bottom, or an inferior) arcuate rail 602 spaced apart from, and substantially parallel to, the first arcuate rail 601. In one embodiment, the first and second arcuate rails each comprise an anterior edge 603 defining an inside curve or circumference of the scaffold that is adjacent to the trabecular meshwork 108 when inserted in the Schlemm's canal 110. Similarly, the first and second arcuate rails each comprise a posterior edge 604 defining an outside curve or circumference of the arcuate scaffold that is adjacent the posterior wall 122 of the Schlemm's canal 110 and the one or more collector channels when inserted in the Schlemm's canal 110. The device 600 further comprises a number of structural components 605A, 605B and 605C coupled to the first arcuate rail and the second arcuate rail to maintain the respective anterior and posterior edges 603, 604 of the first and second arcuate rails 601, 602 spaced apart from, and substantially parallel to, each other. The structural posts in this and all other embodiments described herein can be of any size or shape so long as they serve the functions described herein, namely to maintain the respective anterior and posterior edges of the first and second arcuate rails spaced apart from, and substantially parallel to, each other. Although the embodiment depicts only one structural component 605B it should be understood that multiple structural components 605B may be present according to embodiments of the invention. The space bounded by the first and second arcuate rails 601, 602 and adjacent structural components 605A, 605B and 605C defines a potential space 608. According to the embodiment, structural component 605B is a straight post, while structural components 605A and 605C at respective ends of the arcuate scaffold, are of a different shape, e.g., curved or bowed outwardly, in order to ease passage of the arcuate scaffold along the Schelmm's canal 110.

In the above described embodiment, and in the embodiments described below, the shape of the first and second arcuate rails is the same, for example, flat or straight, or curved, between their anterior and posterior edges, and the planes in which the first and second rails are oriented are substantially the same, but offset from one another. It is appreciated that other embodiments are possible in which the shape of the first and second arcuate rails may be different, for example, the first arcuate rail may be curved while the second arcuate rail may be flat, or the first arcuate rail may be convex, while the second arcuate rail may be concave, between their respective anterior and posterior edges. Likewise, the planes in which the first and second rails are oriented may be different, for example, where the distance between the respective anterior edges is different than the distance between the respective posterior edges of the first and second arcuate rails.

Figure 7A:
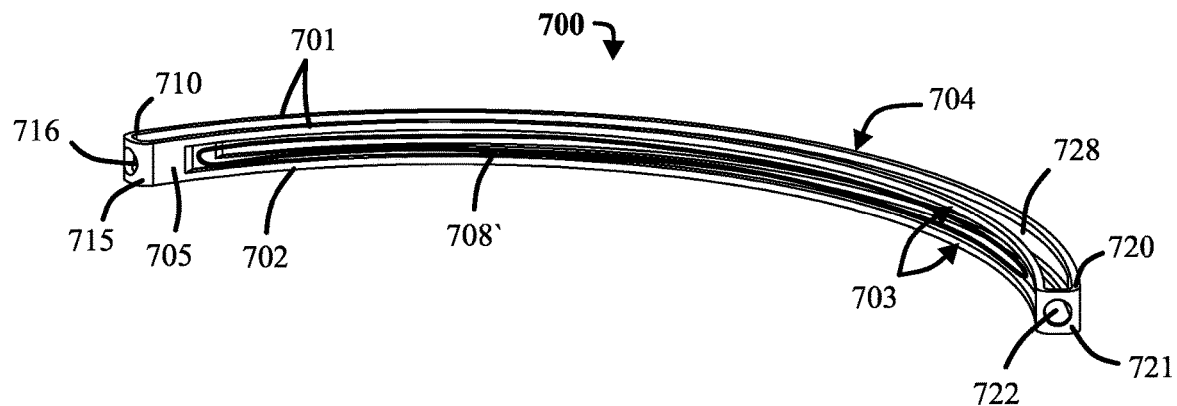
FIG. 7A is an anterior perspective view of an embodiment of the aqueous humor outflow implants disclosed herein.
Figure 7B:
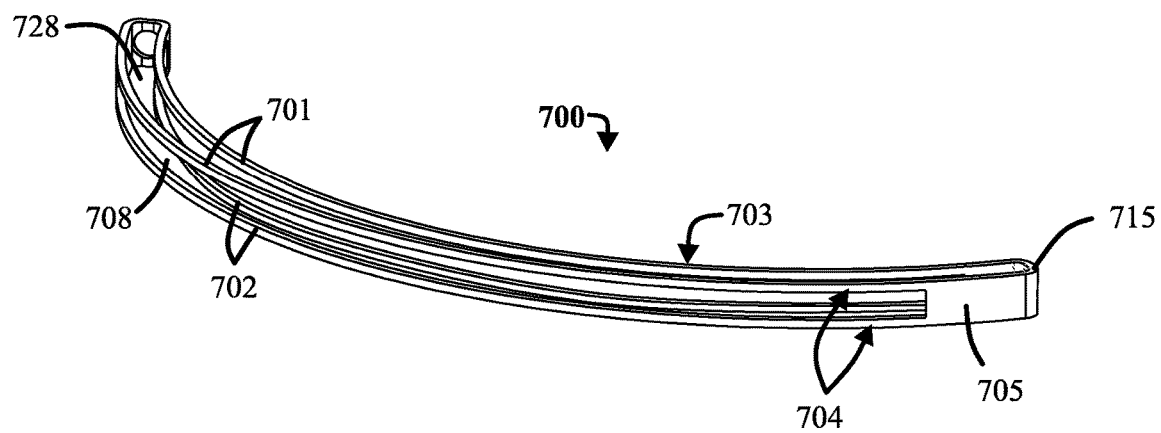
FIG. 7B is a posterior perspective view of an embodiment of the aqueous humor outflow implants disclosed herein.

FIGS. 7A and 7B are respective anterior and posterior views depicting an embodiment 700 created with a flat sheet that has sheet material removed at appropriate locations to create arcuate rails that form a structure with open spaces separating the arcuate rails. Alternatively, embodiment 700 is created with a flat sheet cutout and folded upon itself. The embodiment 700 of the aqueous humor outflow implant device comprises an arcuate scaffold shaped and sized like the embodiment 600 to fit within a conventional aqueous humor outflow pathway of a mammalian eye to receive aqueous humor from the trabecular meshwork 108 of the mammalian eye and allow aqueous humor to flow through the arcuate scaffold to one or more collector channels 123 that originate in a posterior wall 122 of the Schlemm's canal 110. The arcuate scaffold comprises a first (i.e., a top, or a superior) arcuate rail 701, and a second (i.e., a bottom, or an inferior) arcuate rail 702 spaced apart from, and substantially parallel to, the first arcuate rail 701. In one embodiment, the first and second arcuate rails each comprise an anterior edge 703 defining an inside curve or circumference of the scaffold that is adjacent to the trabecular meshwork 108 when inserted in the Schlemm's canal 110. Similarly, the first and second arcuate rails each comprise a posterior edge 704 defining an outside curve or circumference of the arcuate scaffold that is adjacent the posterior wall 122 of the Schlemm's canal 110 and the one or more collector channel entrances 121 when inserted in the Schlemm's canal 110. The embodiment 700 further comprises a number of structural components 705 coupled to the first arcuate rail and the second arcuate rail to maintain the respective anterior and posterior edges 703, 704 of the first and second arcuate rails 701, 702 spaced apart from, and substantially parallel to, each other. Unlike the embodiment 600, the embodiment 700 includes a window or space 728 between the respective anterior and posterior edges 703, 704 of the first and second arcuate rails 701, 702. In this embodiment, the structural components 705 coupled to the first arcuate rail and the second arcuate rail also maintain the anterior and posterior edges 703, 704 of the first arcuate rail 701 spaced apart from, and substantially parallel to, each other, and maintain the anterior and posterior edges 703, 704 of the second arcuate rail 702 spaced apart from, and substantially parallel to, each other. As mentioned above, the embodiment 700 is created with a flat sheet that has material removed at appropriate locations to create arcuate rails that form a structure with open spaces separating the arcuate rails. The points of the folds 710 and 720 establish respective ends 715 and 721 adjacent to structural components 705. The ends are curved or bowed outwardly, rather than squared or angular, in order to ease passage of the arcuate scaffold along the Schelmm's canal 110. The ends 715 and 721 each comprise a hole or opening 716, 722 to facilitate flow of aqueous humor. The hole in both ends of the arcuate scaffold, as discussed further below, can also be used to interact with a delivery device mechanism.

Figure 8A:
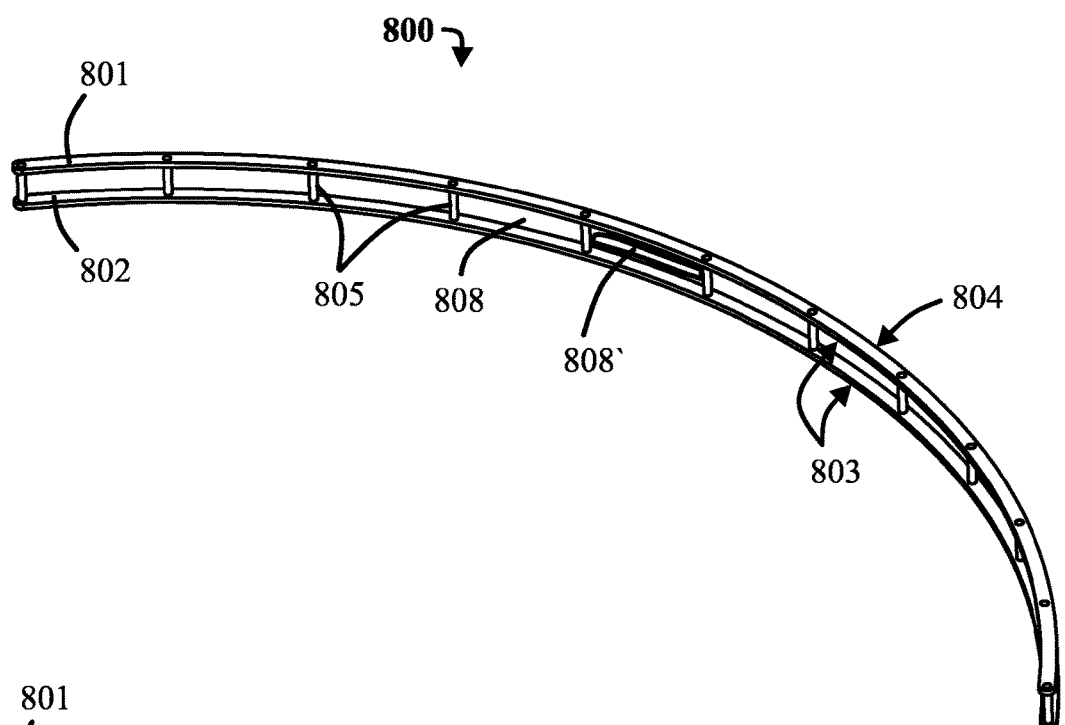
FIG. 8A is an anterior perspective view of an embodiment of the aqueous humor outflow implants disclosed herein.
Figure 8B:
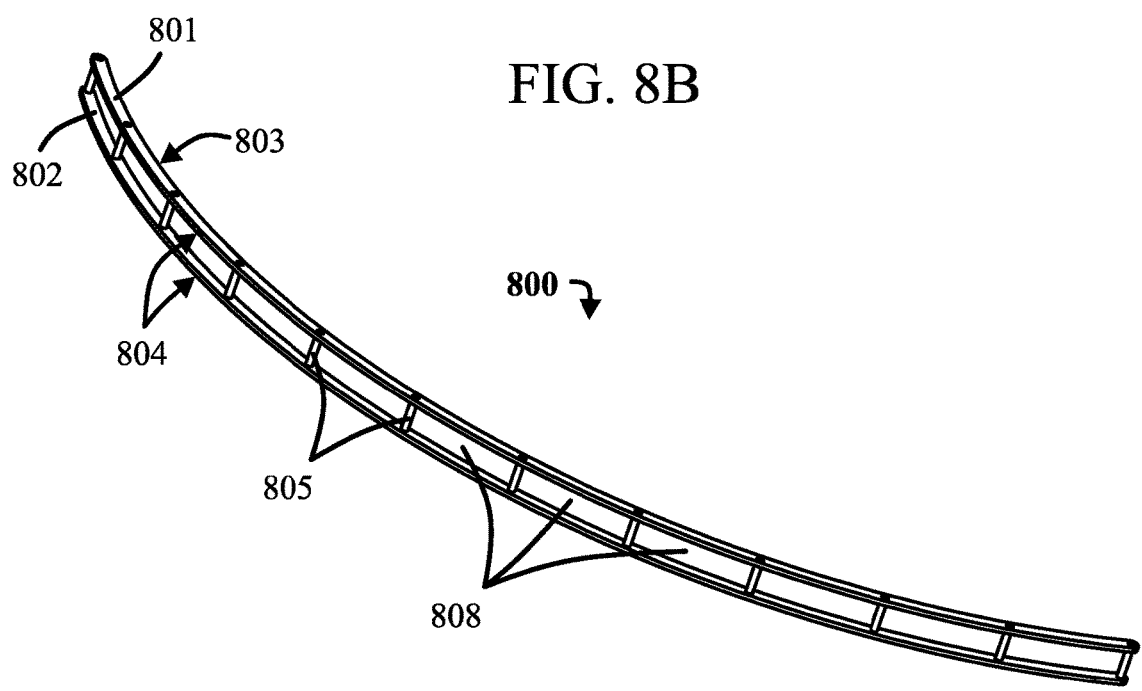
FIG. 8B is a posterior perspective view of an embodiment of the aqueous humor outflow implants disclosed herein.

FIGS. 8A and 8B are respective anterior and posterior views depicting an embodiment 800 with a micro-welded body in which arcuate rails are joined by one or more structural components that connect the top arcuate rail with the bottom arcuate rail. The structural components may be of any cross-sectional shape. The structural components may connect the top and bottom arcuate rails by a variety of methods including interference fits between ends of the structural components and the holes that receive them in the arcuate rails and welding of the structural components to the arcuate rails. The embodiment 800 of the aqueous humor outflow implant device comprises an arcuate scaffold shaped and sized like the embodiments 600 and 700 to fit within a conventional aqueous humor outflow pathway of a mammalian eye to receive aqueous humor from the trabecular meshwork 108 of the mammalian eye and allow aqueous humor to flow through the arcuate scaffold to one or more collector channels 123 that originate in a posterior wall 122 of the Schlemm's canal 110 The arcuate scaffold comprises a first (i.e., a top, or a superior) arcuate rail 801, and a second (i.e., a bottom, or an inferior) arcuate rail 802 spaced apart from, and substantially parallel to, the first arcuate rail 801. In one embodiment, the first and second arcuate rails 801 and 802 each comprise an anterior edge 803 defining an inside curve or circumference of the scaffold that is adjacent to the trabecular meshwork 108 when inserted in the Schlemm's canal 110. Similarly, the first and second arcuate rails 801 and 802 each comprise a posterior edge 804 defining an outside curve or circumference of the arcuate scaffold that is adjacent the posterior wall 122 of the Schlemm's canal 110 and one or more collector channel entrances 121 when inserted in the Schlemm's canal 110. The embodiment 800 further comprises a number of structural components 805 coupled to the first arcuate rail and the second arcuate rail to maintain the respective anterior and posterior edges 803, 804 of the first and second arcuate rails 801, 802 spaced apart from, and substantially parallel to, each other.

Figure 9A:
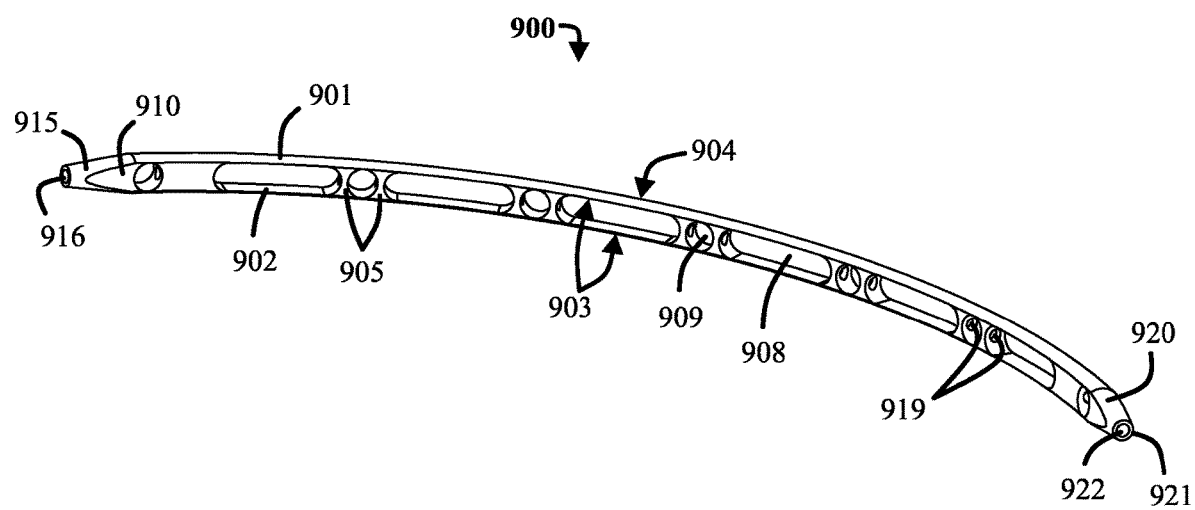
FIG. 9A is an anterior perspective view of an embodiment of the aqueous humor outflow implants disclosed herein.
Figure 9B:
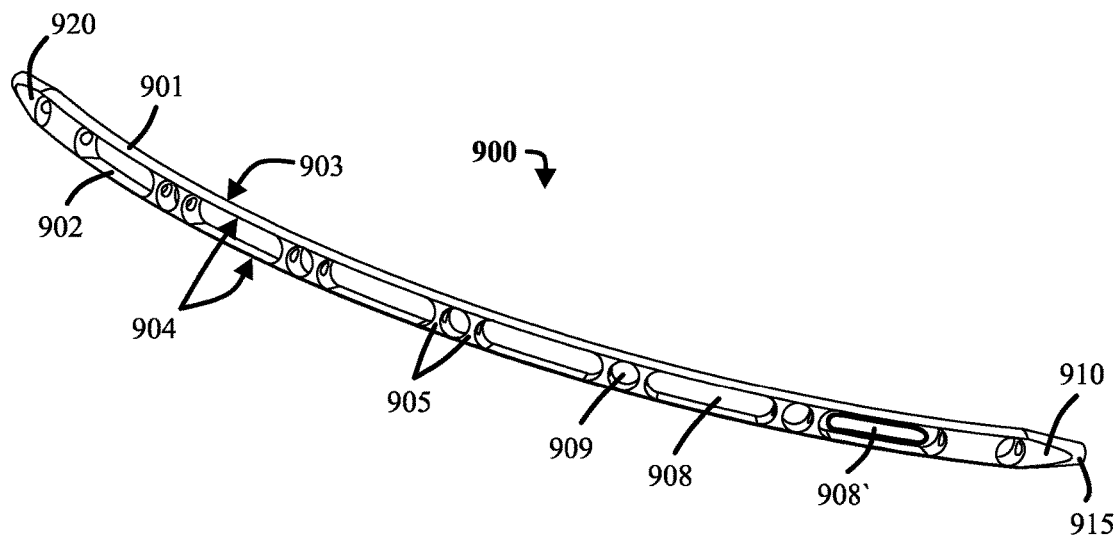
FIG. 9B is a posterior perspective view of an embodiment of the aqueous humor outflow implants disclosed herein.

FIGS. 9A and 9B are respective anterior and posterior views depicting an embodiment 900, similar to the embodiments 600 and 800, with anterior-posterior (front-back) symmetry (i.e., full anterior-posterior rail thickness). Unlike embodiment 700, embodiment 900 is without top or bottom windows or spaces. The embodiment 900 comprises an arcuate scaffold designed to fit within the conventional aqueous humor outflow pathway of a mammalian eye. The arcuate scaffold comprises a first arcuate rail 901, and a second arcuate rail 902 spaced apart from, and substantially parallel to, the first arcuate rail 901. In one embodiment, the first and second arcuate rails each comprise an anterior edge 903 defining an inside curve or circumference of the scaffold that is adjacent to the trabecular meshwork 108 when inserted in the Schlemm's canal 110. Similarly, the first and second arcuate rails each comprise a posterior edge 904 defining an outside curve or circumference of the arcuate scaffold that is adjacent the posterior wall 122 of the Schlemm's canal 110 and the one or more collector channel entrances 121 when inserted in the Schlemm's canal 110. The embodiment 900 further comprises a number of structural components 905 coupled to the first arcuate rail and the second arcuate rail to maintain the respective anterior and posterior edges 903, 904 of the first and second arcuate rails 901, 902 spaced apart from, and substantially parallel to, each other. These structural components 905 may frame an opening, e.g., a circular opening 909, normal to the longitudinal axis of the arcuate scaffold. Further, the structural components 905 may further include openings 919 along the longitudinal axis of the arcuate scaffold connecting opening 909 with openings or spaces 908. Note this embodiment has both an opening or space 908 between structural components 905 and the above mentioned smaller space or opening 909 within, or between a colocated pair of, the structural components 905. These two spaces 908 and 909 have different functions: space 908 combines with the trabecular meshwork 108 and the posterior wall 122 of Schlemm's canal 110 to form an analogous chamber 908' (as depicted by the dotted line in FIG. 9B). However, the smaller space 909 within the structural components 905 is primarily for manipulation of the implant device with a tool or instrument.

As will be discussed further below in connection with other embodiments, the structural components 905 may not extend to the posterior edge 904 of the first and second arcuate rails 901, 902, providing not so much an opening, but a depression or a recession (see, e.g., 1007 in FIGS. 10A and 10B, 1207 in FIGS. 12A and 12B, 1407 in FIGS. 14A-14O, FIG. 14O, and corresponding description). This recession provides the same function as opening 919, however, which is to allow flow of aqueous humor between the analogous chambers 908'. An additional benefit of the recess versus an opening within the structural component is reducing the implant device's surface area against the posterior wall 122 of Schlemm's canal 110. This both limits damage to the posterior wall 122 of Schlemm's canal 110 and decreases the likelihood of obstruction of a collector channel entrance 121 by the implant. According to the embodiments illustrated in FIGS. 10B, 12B, 14A, 14B, 14N, 14O, 15A, and corresponding discussion herein, the recession 1007, 1207, and 1407, depending on the extent to which is anteriorly depressed, may combine or merge with respective opening 1019, 1219, and 1419 as depicted, e.g., in FIGS. 10B, 12B, 14A, 14D, 14N, 14O, 15A, to further increase the flow of aqueous humor between the respective analogous chambers 1008', 1208' and 1408'.

It is appreciated that while opening 909 is circular in the embodiment depicted in FIGS. 9A and 9B, other geometries or shapes are envisioned according to the form factor of the tool or instrument that engages the arcuate scaffold at opening 909 to manipulate the implant device. Likewise, openings 1009, 1109, 1209, 1309, 1409 in the embodiments discussed below may be circular, or some other shape that accommodates a tool for manipulation of the implant device.

Figure 10A:
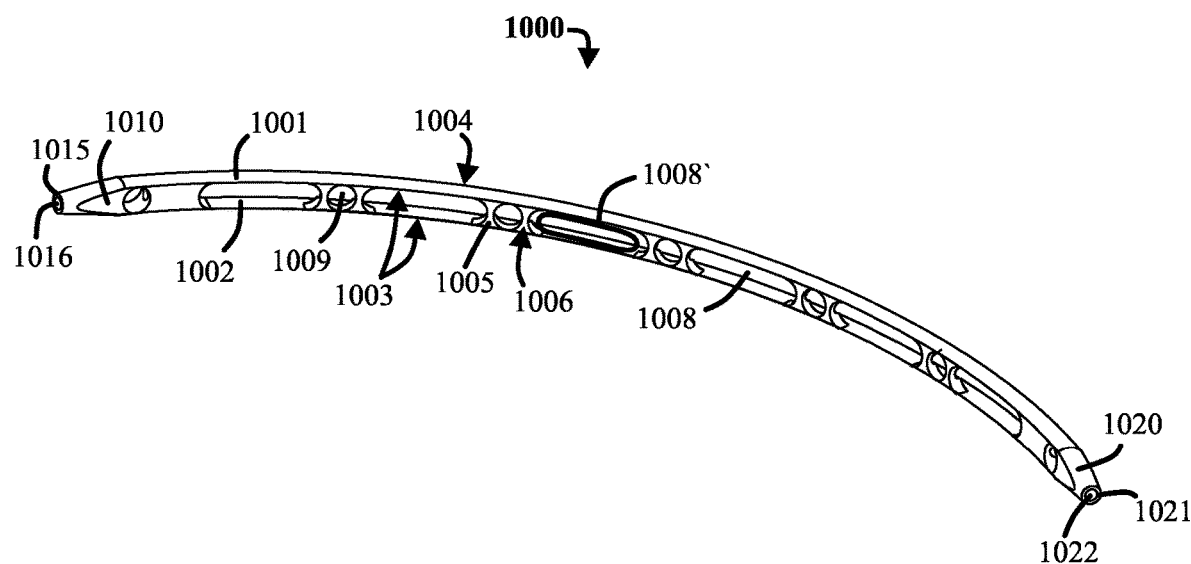
FIG. 10A is an anterior perspective view of an embodiment of the aqueous humor outflow implants disclosed herein.
Figure 10B:
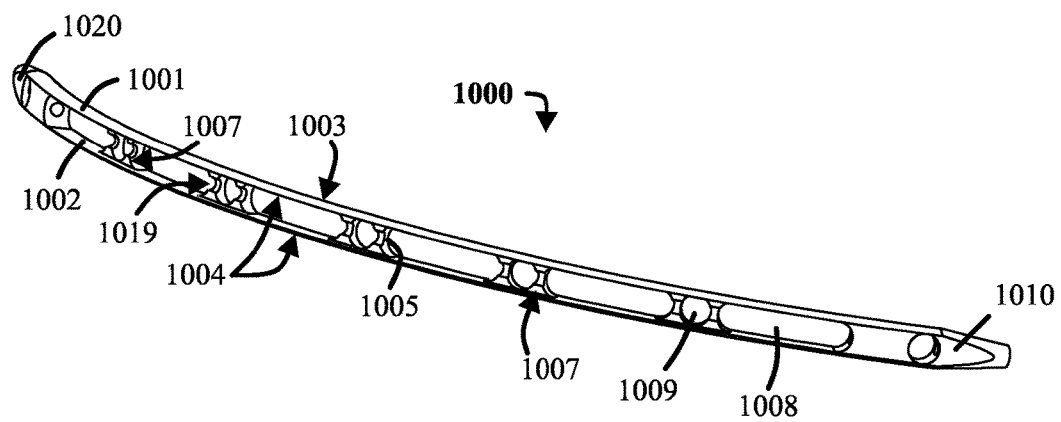
FIG. 10B is a posterior perspective view of an embodiment of the aqueous humor outflow implants disclosed herein.

FIGS. 10A and 10B are respective anterior and posterior views depicting an embodiment with a recessed posterior post/structural component (i.e., without full anterior-posterior post/structural component thickness, relative to the full width, anterior-posterior, of the first and second arcuate rails). The embodiment 1000 comprises an arcuate scaffold designed to fit within the conventional aqueous humor outflow pathway of a mammalian eye. The arcuate scaffold comprises a first arcuate rail 1001, and a second arcuate rail 1002 spaced apart from, and substantially parallel to, the first arcuate rail 1001. In one embodiment, the first and second arcuate rails each comprise an anterior edge 1003 defining an inside curve or circumference of the scaffold that is adjacent to the trabecular meshwork 108 when inserted in the Schlemm's canal 110. Similarly, the first and second arcuate rails each comprise a posterior edge 1004 defining an outside curve or circumference of the arcuate scaffold that is adjacent the posterior wall 122 of the Schlemm's canal 110 and the one or more collector channel entrances 121 when inserted in the Schlemm's canal 110. The embodiment 1000 further comprises a number of structural components 1005 coupled to the first arcuate rail and the second arcuate rail to maintain the respective anterior and posterior edges 1003, 1004 of the first and second arcuate rails 1001, 1002 spaced apart from, and substantially parallel to, each other. Unlike the embodiment 900 depicted in FIGS. 9A and 9B, the structural components 1005 (i.e., "posts") in embodiment 1000 do not extend the full width between the anterior and posterior edges of the first and second arcuate rails. In particular, while the anterior edge 1006 of the structural components 1005 aligns with the anterior edges 1003 of the first and second arcuate rails 1001, 1002, the posterior edge 1007 of the structural components 1005 is recessed with respect to the posterior edges 1004 of the first and second arcuate rails 1001, 1002. Further, the structural components 1005 may include openings 1019 along the longitudinal axis of the arcuate scaffold connecting opening 1009 with openings or spaces 1008.

Said another way, the structural components in the aqueous humor outflow device each comprises a first face (i.e., a top face) coupled to the first arcuate rail, a second face (i.e., a bottom face) coupled to the second arcuate rail, an anterior face having respective first/top and second/bottom edges that meet at the anterior edges of the first and second arcuate rails, and a posterior face, at least a portion of which is recessed with respect to at least one of the posterior edges of the first and second arcuate rails. In one embodiment of the aqueous humor outflow device, the posterior face of the structural component that is recessed with respect to at least one of the posterior edges of the first and second arcuate rails comprises a posterior face with at least one edge (either the top or bottom edge) that is recessed with respect to at least one of the posterior edges of the first and second arcuate rails.

In one embodiment, the manufacturing process for the aqueous humor outflow device involves fastening the structural components to the first and second arcuate rails, for example, by welding, micro-welding, or weaving. It is appreciated, however, that depending on the manufacturing process used to produce the aqueous humor outflow device that the structural components and first and second arcuate rails are not so much coupled to one another in the sense that the components and rails are separately manufactured and then assembled, but rather manufactured as a single component from a block, strip, wire, tube, or sheet of raw material. For example, the device could be 3D-printed, stamped, extruded, laser-etched, or cut out of raw material such as a biocompatible material, including metal, Nitinol® sheet (depicted in FIGS. 6A and 6B), titanium, a polymer, a drug eluting polymer, ceramic material, biological material, or combinations thereof. In the case of biological material, the manufacturing process for the aqueous humor outflow device may involve growing the structural components and the first and second arcuate rails in a laboratory from living cells or 3D printing them onto a biocompatible substrate.

According to another embodiment of the aqueous humor outflow device, the arcuate scaffold may further comprise a functional coating, such as a drug coating, an anticoagulant drug coating, or a wetting agent to improve aqueous humor flow within the arcuate scaffold.

Figure 11A:
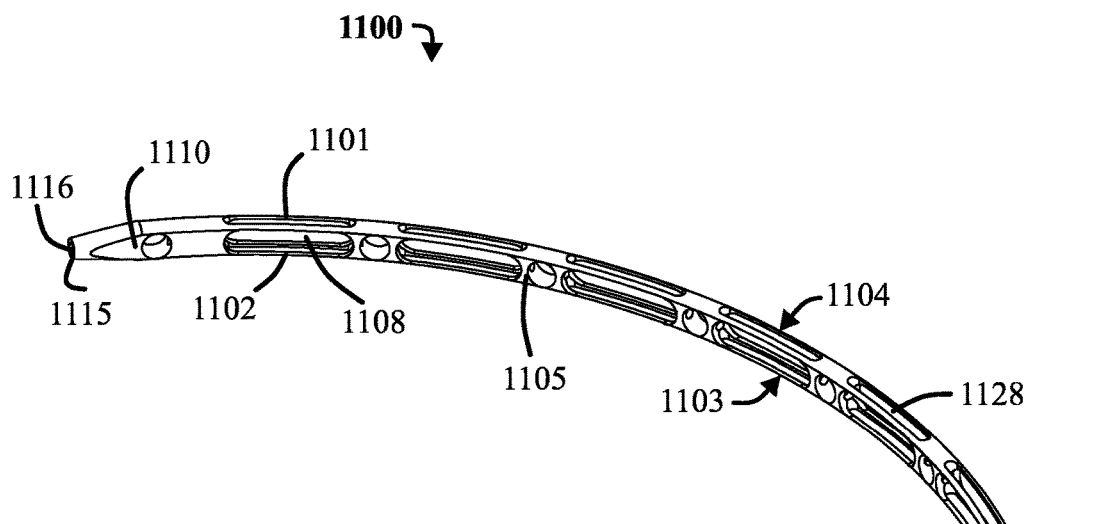
FIG. 11A is an anterior perspective view of an embodiment of the aqueous humor outflow implants disclosed herein.
Figure 11B:
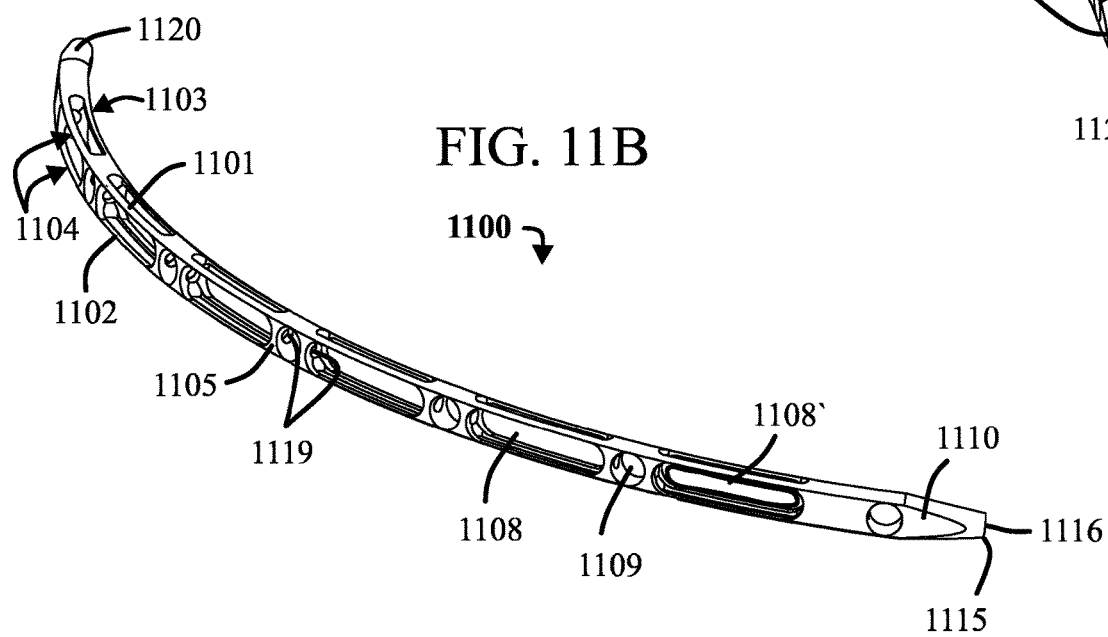
FIG. 11B is a posterior perspective view of an embodiment of the aqueous humor outflow implants disclosed herein.

FIGS. 11A and 11B are respective anterior and posterior views depicting another embodiment 1100 with anterior-posterior (front-back) symmetry. FIGS. 11A and 11B depict an embodiment 1100 that is similar to the embodiments 600 and 800, with anterior-posterior (front-back) symmetry (i.e., full anterior-posterior rail thickness). Furthermore, like embodiment 700, embodiment 1100 includes top and/or bottom windows or spaces 1128. The embodiment 1100 comprises an arcuate scaffold designed to fit within the conventional aqueous humor outflow pathway of a mammalian eye. The arcuate scaffold comprises a first arcuate rail 1101, and a second arcuate rail 1102 spaced apart from, and substantially parallel to, the first arcuate rail 1101. In one embodiment, the first and second arcuate rails each comprise an anterior edge 1103 defining an inside curve or circumference of the scaffold that is adjacent to the trabecular meshwork 108 when inserted in the Schlemm's canal 110. Similarly, the first and second arcuate rails each comprise a posterior edge 1104 defining an outside curve or circumference of the arcuate scaffold that is adjacent to the posterior wall 122 of the Schlemm's canal 110 and the one or more collector channel entrances 121 when inserted in the Schlemm's canal 110. The embodiment 1100 further comprises a number of structural components 1105 coupled to the first arcuate rail and the second arcuate rail to maintain the respective anterior and posterior edges 1103, 1104 of the first and second arcuate rails 1101, 1102 spaced apart from, and substantially parallel to, each other. These structural components 1105 may frame an opening, e.g., circular opening 1109, normal to the longitudinal axis of the arcuate scaffold. Further, the structural components 1105 may further include openings 1119 along the longitudinal axis of the arcuate scaffold connecting opening 1109 with openings or spaces 1108.

Figure 12A:
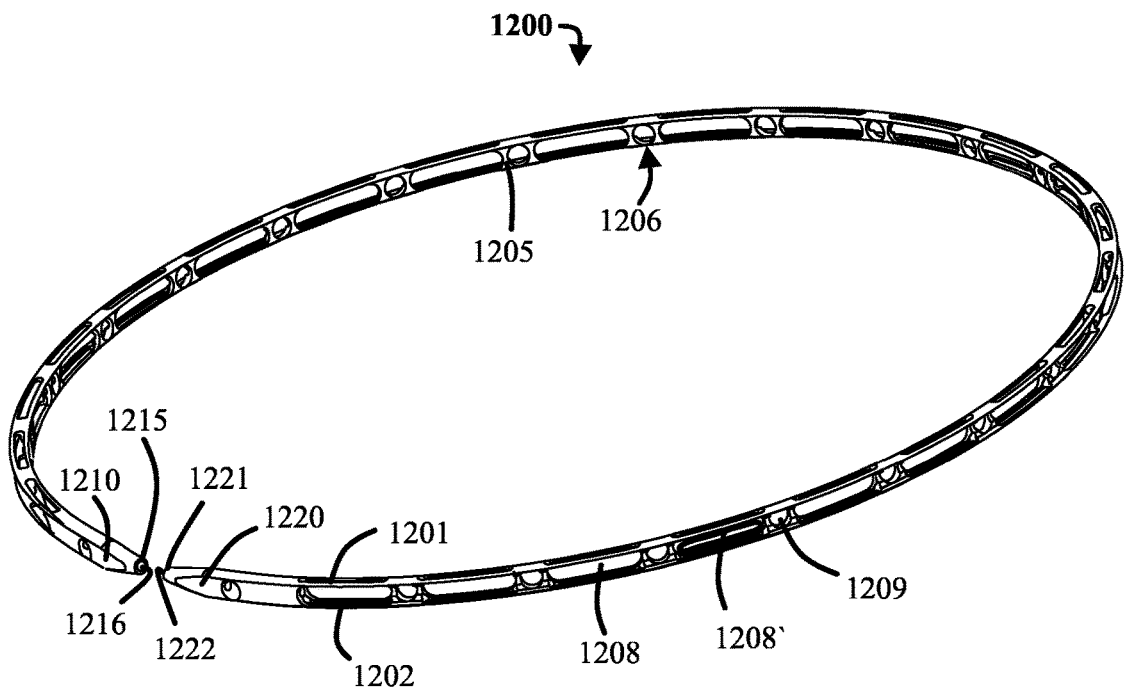
FIG. 12A is a perspective view of an embodiment of the aqueous humor outflow implants disclosed herein.
Figure 12B:
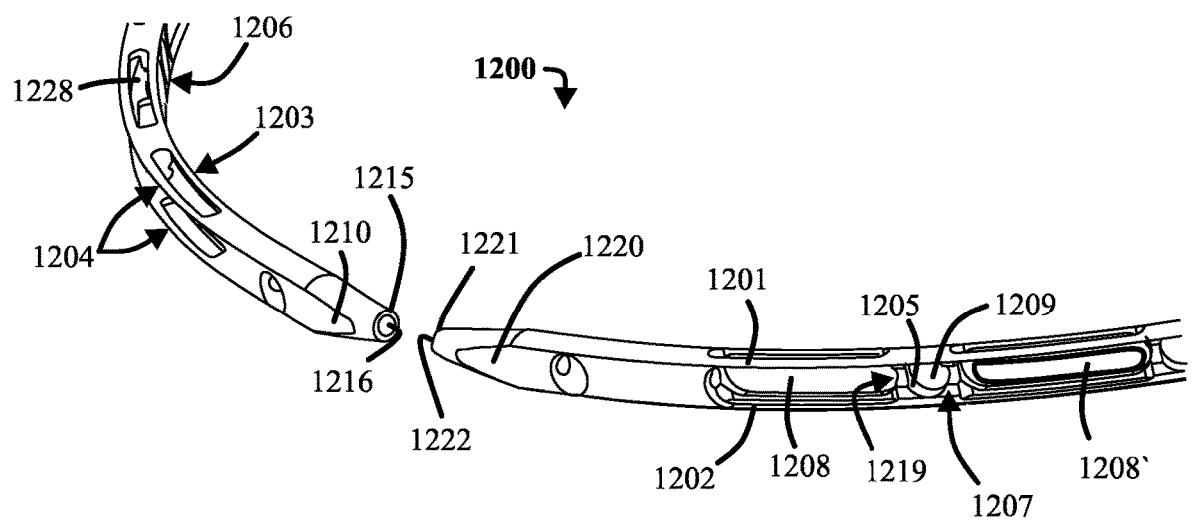
FIG. 12B is an enlarged perspective view of the ends of the embodiment of the aqueous humor outflow implants disclosed herein.

FIGS. 12A and 12B depict an embodiment 1200 with a longer arc length than, but otherwise similar in many respects to, the embodiment 1000 depicted in FIGS. 10A and 10B and the embodiment 1100 depicted in FIGS. 11A and 11B. Like embodiment 1000, embodiment 1200 does not include full anterior-posterior post/structural component 1205 thickness, relative to the full width, anterior-posterior, of the first and second arcuate rails 1201, 1202, as depicted by depression 1207. However, it is appreciated that the embodiment may be modified to be similar to the embodiment 900 depicted in FIGS. 9A and 9B, in which the structural components 1205 (i.e., "posts") in embodiment 1200 do extend the full width between the anterior and posterior edges 1203, 1204 of the first and second arcuate rails 1201, 1202. In particular, the posterior edge 1207 of the structural components 1205 may be extended in a posterior direction so that the posterior edge 1207 is aligned with respect to the posterior edges 1204 of the first and second arcuate rails 1201, 1202. Like the structural components 905, structural components 1205 may further include openings 1219 along the longitudinal axis of the arcuate scaffold connecting openings 1209 with openings or spaces 1208.

Figure 13A:
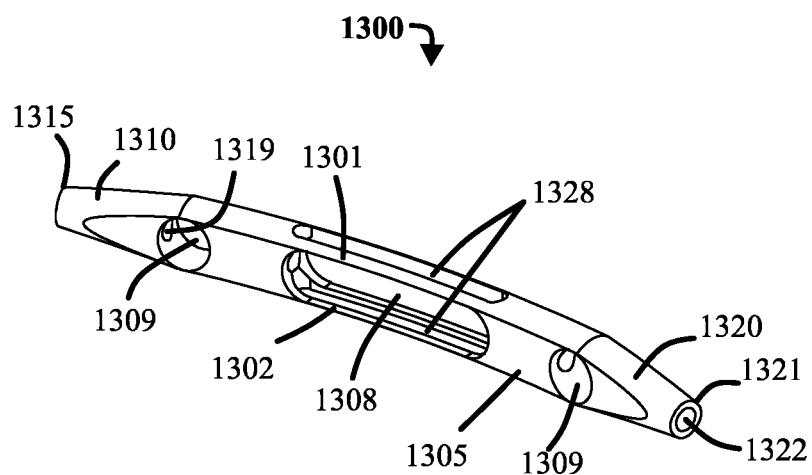
FIG. 13A is an anterior perspective view of an alternative embodiment of the aqueous humor outflow implants disclosed herein.
Figure 13B:
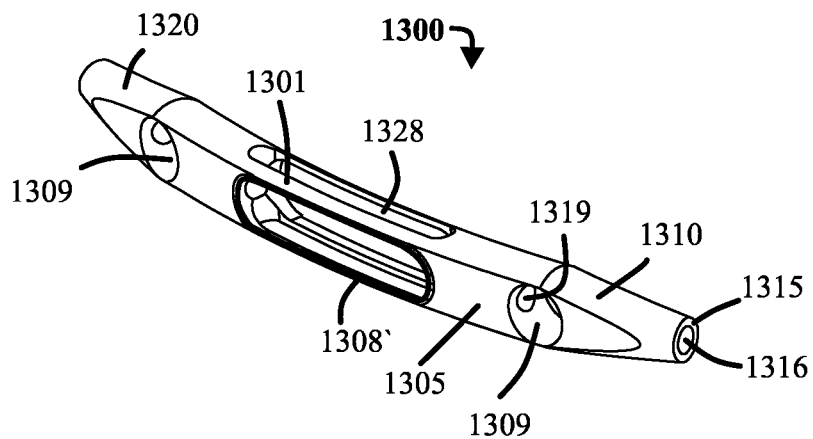
FIG. 13B is a posterior perspective view of an alternative embodiment of the aqueous humor outflow implants disclosed herein.
Figure 13C:
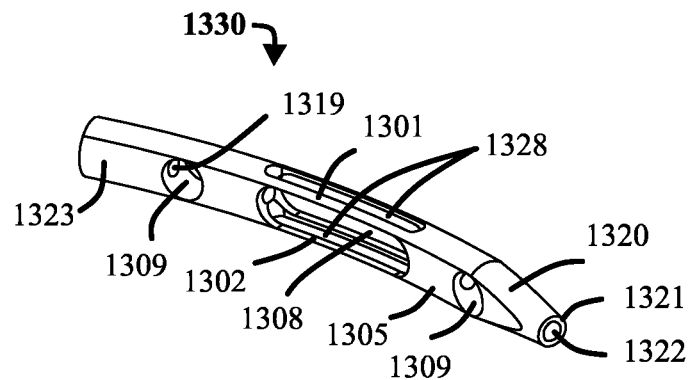
FIG. 13C is an anterior perspective view of an alternative embodiment of the aqueous humor outflow implants disclosed herein.
Figure 13D:
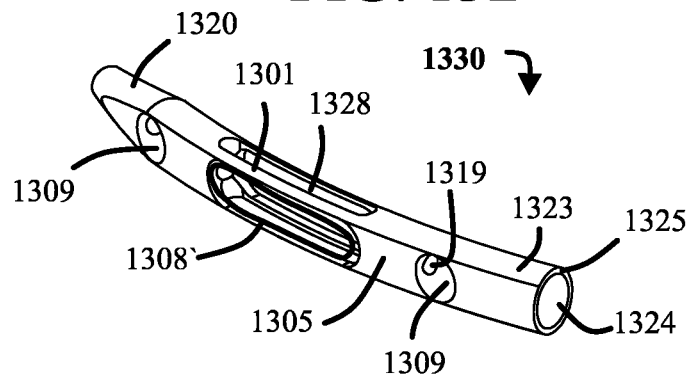
FIG. 13D is a posterior perspective view of an alternative embodiment of the aqueous humor outflow implants disclosed herein.
Figure 13E:
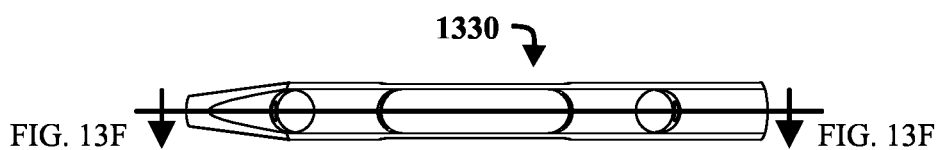
FIG. 13E is a posterior elevation view of an alternative embodiment of the aqueous humor outflow implants disclosed herein.
Figure 13F:
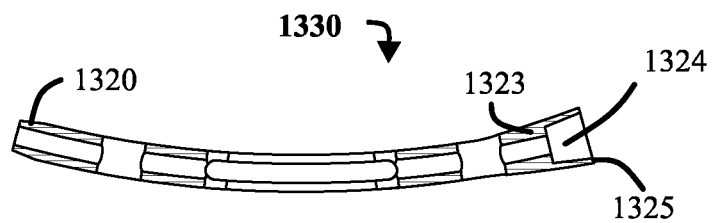
FIG. 13F is an overhead sectional view of an alternative embodiment of the aqueous humor outflow implants disclosed herein.

FIGS. 13A and 13B are respective anterior and posterior views depicting an embodiment 1300 with only one respective window 1328 in the first (top) and second (bottom) arcuate rails 1301 and 1302. Like the embodiment 1100 depicted in FIGS. 11A and 11B, embodiment 1300 manifests anterior-posterior (front-back) symmetry, similar to the embodiments 600 and 800, with anterior-posterior (front-back) symmetry. Structural components 1305 along with ends 1310 or 1320 may frame an opening, e.g., circular opening 1309, normal to the longitudinal axis of the arcuate scaffold. Further, the structural components 1305 may further include openings 1319 along the longitudinal axis of the arcuate scaffold connecting opening 1309 with openings or spaces 1308. Similarly, respective openings 1319 located adjacent to the ends 1310 and 1320 of the embodiment 1300 form a lumen connecting to the respective openings 1316 and 1322 in ends 1310 and 1320.

Furthermore, like embodiment 1100, embodiment 1300 includes a top and/or bottom window or space 1328. In other respects, this embodiment is similar to embodiments previously discussed, such as embodiment 1100. According to this shorter embodiment, the arcuate scaffold having a first and/or second end that tapers to an apex enables introduction of the arcuate scaffold into one of the one or more collector channels 123 that originate in the posterior wall 122 of the Schlemm's canal 110, or entrances thereof, and the dilation thereof as the collector channel entrance 121 and collector channel 123 widen to accommodate the increasing cross-sectional area of the scaffold as the scaffold is inserted into the collector channel 123.

In the aqueous humor outflow device in embodiments 600, 700, 800, 900, 1000, 1100, 1200 and 1300, the first and second arcuate rails and the structural components frame one or more respective openings 608, 708, 808, 908, 1008, 1108, 1208 and 1308. Ideally, but not required according to some embodiments, there is at least one opening per Schlemm's canal chamber 131, through which to receive the aqueous humor from the trabecular meshwork 108 and to allow the flow of the aqueous humor through the arcuate scaffold to the one or more collector channels 123 when inserted in the Schlemm's canal 110. When implanted into the Schlemm's canal 110, the openings 608, 708, 808, 908, 1008, 1108, 1208 and 1308 bounded by the first and second arcuate rails 601, 602, 701, 702, 801, 802, 901, 902, 1001, 1002, 1101, 1102, 1201, 1202 and 1301, 1302, adjacent structural components 605A, 605B, 605C, 705, 805, 905, 1005, 1105, 1205 and 1305, trabecular meshwork 108, and posterior wall 122 of Schlemm's canal 110 defines a potential three dimensional space or chamber, indicated by dotted lines, and referenced at 608', 708', 808', 908', 1008', 1108', 1208', and 1308' that is analogous to the chambers 131 present in a healthy Schlemm's canal 110.

Figure 29A:
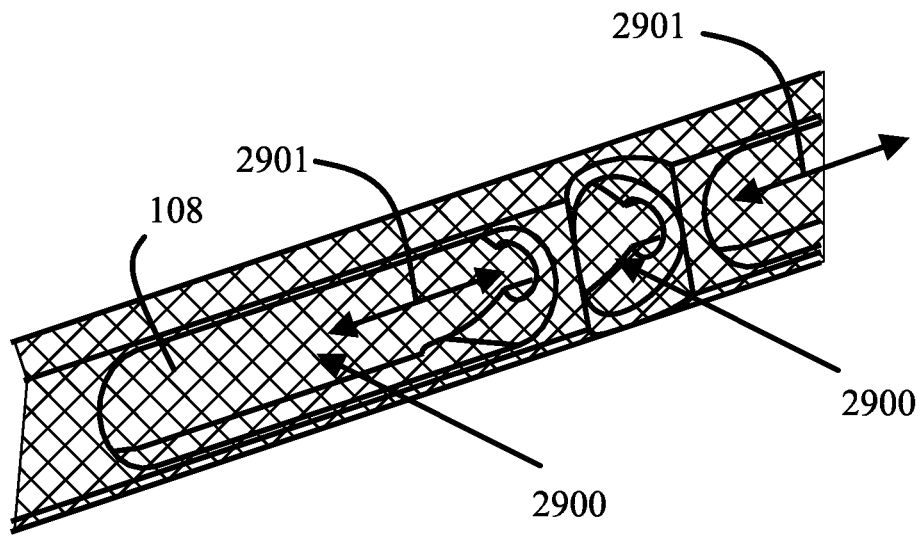
FIG. 29A is an enlarged front perspective partial view of an embodiment showing the flow of aqueous humor through the trabecular meshwork into the lumen of the embodiment.
Figure 29B:
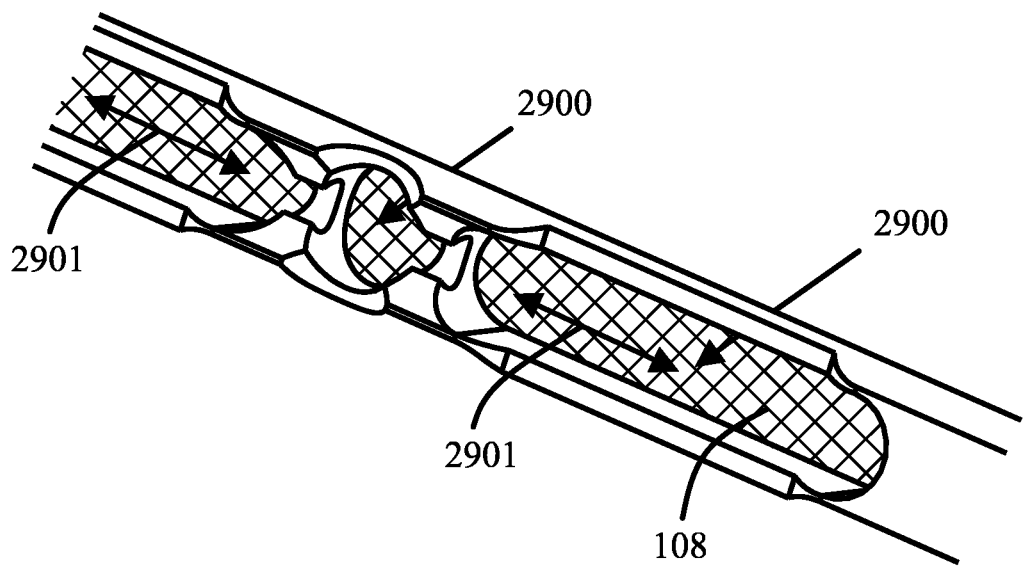
FIG. 29B is an enlarged back perspective partial view of an embodiment showing the flow of aqueous humor through the trabecular meshwork into the lumen of the embodiment.

In the embodiments 1000 and 1200 depicted in FIGS. 10A, 10B, 12A and 12B, the structural components 1005, 1205 (i.e., "posts") do not extend the full width between the anterior and posterior edges of the first and second arcuate rails. In particular, while the anterior edge 1006, 1206 of the structural components 1005, 1205 aligns with the anterior edges 1003, 1203 of the first and second arcuate rails 1001, 1002, 1201, 1202, the posterior edge 1007, 1207 of the structural components 1005, 1205 is recessed with respect to the posterior edges 1004, 1204 of the first and second arcuate rails 1001, 1002, 1201, 1202. This can be expressed in geometric terms, wherein:

a. the first and second arcuate rails of the aqueous humor outflow device, and their respective anterior and posterior edges define a first cross-sectional area in a plane normal to a longitudinal axis of the arcuate scaffold, b. a cross section of at least one of the structural components defines a second cross-sectional area in the plane normal to the longitudinal axis of the arcuate scaffold less than the first cross-sectional area, and c. a difference between the first cross-sectional area and the second cross-sectional area defines an open area, such that the arcuate scaffold allows for the flow of the aqueous humor through the open area in a direction from the anterior edge of the arcuate scaffold to the posterior edge of the arcuate scaffold and in a direction generally along the longitudinal axis of the arcuate scaffold when inserted in the Schlemm's canal 110, as depicted for example in FIGS. 29A and 29B, discussed below. According to the embodiments 1000 and 1200 of the aqueous humor outflow device, the arcuate scaffold allows for flow of aqueous humor through the open area in a direction generally along the longitudinal axis of the arcuate scaffold, and in particular, within and between chambers 131 of the Schlemm's canal 110 to the one or more collector channels 123 that originate in the posterior wall 122 of the Schlemm's canal 110 when inserted in the Schlemm's canal 110.

In one embodiment, the first cross-sectional area of the aqueous humor outflow device in the plane normal to the longitudinal axis of the arcuate scaffold is greater than a cross-sectional area of the Schlemm's canal 110. In particular, according to one embodiment, the first cross-sectional area of the aqueous humor outflow device in the plane normal to the longitudinal axis of the arcuate scaffold is greater than an age- and/or quadrant-specific average cross-sectional area (whether measured in terms of a diameter, or cross-sectional profile) of an expected, or smaller than expected, resting configuration of the Schlemm's canal 110 or a collector channel in a patient without glaucoma or other intraocular disease state.

According to one embodiment, the first cross-sectional area of the aqueous humor outflow device in the plane normal to the longitudinal axis of the arcuate scaffold being greater than the cross-sectional area of the Schlemm's canal 110 causes dilation of the Schlemm's canal 110 and/or the collector channel 123. According to one embodiment, the first cross-sectional area of the aqueous humor outflow device in the plane normal to the longitudinal axis of the arcuate scaffold being greater than the cross-sectional area of the Schlemm's canal 110 improves aqueous flow by physically stretching the trabecular meshwork 108. In one embodiment, the first cross-sectional area of the aqueous humor outflow device in the plane normal to the longitudinal axis of the arcuate scaffold being greater than the cross-sectional area of the Schlemm's canal 110 separates the trabecular meshwork 108 from the posterior wall 122 of the Schlemm's canal 110, thereby improving aqueous humor flow.

In one embodiment, the first cross-sectional area of the aqueous humor outflow device in the plane normal to the longitudinal axis of the arcuate scaffold being greater than the cross-sectional area of the Schlemm's canal 110 can relieve a herniation 108' in the trabecular meshwork 108 into an entrance 121 of one of the plurality of collector channels 123.

In one embodiment, the first cross-sectional area of the aqueous humor outflow device in the plane normal to the longitudinal axis of the arcuate scaffold being greater than the cross-sectional area of the Schlemm's canal 110 improves a mechano-sensory or mechano-transducing feedback loop between the Schlemm's canal 110 and the trabecular meshwork 108. In particular, the trabecular meshwork 108 has both mechanosensing and mechanotransducing molecules which can "sense" trabecular meshwork 108 stretch as well as flow of the aqueous humor. Prolonged stretching to the trabecular meshwork 108 results in upregulation of MMPs and downregulation of TIMP (increasing permeability of the extracellular matrix and reducing resistance to aqueous humor flow). Stretching the trabecular meshwork 108 also results in release of Nitric Oxide (NO) and Vascular Endothelial Growth Factor (VEGF) by Schlemm's canal 110 endothelial smooth muscle cells resulting in increased outflow of aqueous humor through the drainage system and the accompanying reduction in IOP. Stretching the trabecular meshwork 108 also results in release of adenosine by the trabecular meshwork cells resulting in increased outflow of aqueous humor through the conventional aqueous outflow drainage system and the accompanying reduction in IOP. Evidence of other mechanisms by which stretching of the trabecular meshwork 108 leads to regulation of aqueous humor outflow and lowering of IOP also exists. As such, a potential IOP lowering benefit could be provided by this embodiment that stretches the trabecular meshwork 108 or otherwise results in tension across its surface.

According to the embodiments described herein, the trabecular meshwork 108 abuts at least one of the openings framed by the first and second arcuate rails and the structural components. For example, with respect to the embodiment 800 depicted in FIGS. 8A and 8B, recall the arcuate scaffold comprises a first arcuate rail 801 and a second arcuate rail 802, and the first and second arcuate rails 801 and 802 each comprise an anterior edge 803 defining an inside curve or circumference of the scaffold that is adjacent the trabecular meshwork 108 when inserted in the Schlemm's canal 110. Similarly, the first and second arcuate rails 801 and 802 each comprise a posterior edge 804 defining an outside curve or circumference of the arcuate scaffold that is adjacent the posterior wall 122 of the Schlemm's canal 110 and the one or more collector channel entrances 121 when inserted in the Schlemm's canal 110. Finally, recall the embodiment 800 further comprises a number of structural components 805 coupled to the first arcuate rail and the second arcuate rail to maintain the respective anterior and posterior edges 803, 804 of the first and second arcuate rails 801, 802 spaced apart from, and substantially parallel to, each other. The openings 808 are framed by the first and second arcuate rails and the structural components 805. When implanted into the Schlemm's canal 110, the space 808 bounded by the first and second arcuate rails 801, 802, adjacent structural components 805, trabecular meshwork 108, and posterior wall 122 of Schlemm's canal 110 defines a potential three dimensional space or chamber 808' that is analogous to the chambers 131 present in a healthy Schlemm's canal 110.

According to one embodiment, the trabecular meshwork 108, when subjected to an asymmetry in pressure between the anterior chamber and Schlemm's canal 110, and in particular, an intraocular pulse pressure, operates as a membrane (i.e., a diaphragm) that stretches and distends into the openings 808 and operates as a piston, in conjunction with a membrane valve (i.e., diaphragm valve) of the Schlemm's canal 110 (e.g., see membrane valve 132 in Schlemm's canal 110 in FIG. 5B), as a membrane pump (i.e., a diaphragm pump) to cause the flow of aqueous humor through the open area in a direction generally along the longitudinal axis of the arcuate scaffold within and between these analogous chambers 808' of the Schlemm's canal 110 to one or more collector channel entrances 121.

An embodiment 1400 is depicted in FIGS. 14A, 14B, 14C and 14D. As in the aqueous humor outflow device in embodiments 600, 700, 800, 900, 1000, 1100, 1200 and 1300, the first and second arcuate rails 1401, 1402 and the structural components 1405, frame an opening 1408, which, when combined with the trabecular meshwork 108 and the posterior wall 122 of Schlemm's canal 110, forms an analogous chamber 1408'. Further, structural components 1405 frame one or more respective openings, e.g., circular opening 1409, normal to the longitudinal axis of the arcuate scaffold. Like the embodiments 1000 and 1200 depicted in FIGS. 10A, 10B, 12A and 12B, the structural components 1405 (i.e., "posts") do not extend the full width between the anterior edges 1403 and posterior edges 1404 of the first and second arcuate rails 1401 and 1402. In particular, while the anterior edge 1406 of the structural components 1405 aligns with the anterior edges 1403 of the first and second arcuate rails 1401, 1402, the posterior edge 1407 of the structural components 1405 is recessed with respect to the posterior edges 1404 of the first and second arcuate rails 1401, 1402. Like the structural components 905, 1005, 1105, and 1205, structural components 1405 may further include openings 1419 along the longitudinal axis of the arcuate scaffold connecting opening 1409 with openings or spaces 1408. Additionally, in this embodiment 1400 of the aqueous humor outflow device, the opening 1409 within or between the structural components 1405 is posteriorly recessed, e.g., concave, indented, or bowed in, as depicted at 1426, and comprises edges that extend in a straight line from a vertex at the anterior edge of the first arcuate rail to a vertex at the anterior edge of the second arcuate rail. According to an embodiment, this posteriorly recessed portion 1426 of the structural components eases coupling of a tool or instrument to be positioned in opening 1409 to allow for mechanical translation (clockwise or counter-clockwise movement) of the arcuate scaffold about its longitudinal axis inside the Schlemm's canal 110. Moreover, the posteriorly recessed portion 1426 in conjunction with the opening 1409 and the instrument also allows for minor adjustments or movements of the aqueous humor outflow device, as a form of controlled testing/confirmation that the aqueous humor outflow device is properly seated in Schlemm's canal 110 after initial implantation within the Schlemm's canal 110. For example, the aqueous humor outflow device can be adjusted after insertion to confirm correct positioning within the Schlemm's canal 110. In this embodiment 1400 of the aqueous humor outflow device, the posteriorly recessed portion 1426 of the structural components 1405 comprises edges that extend in a straight line from a vertex at the anterior edge of the first arcuate rail to a vertex at the anterior edge of the second arcuate rail. However, it is appreciated that these edges may be beveled, or chamfered, according to other embodiments.

Figure 14A:
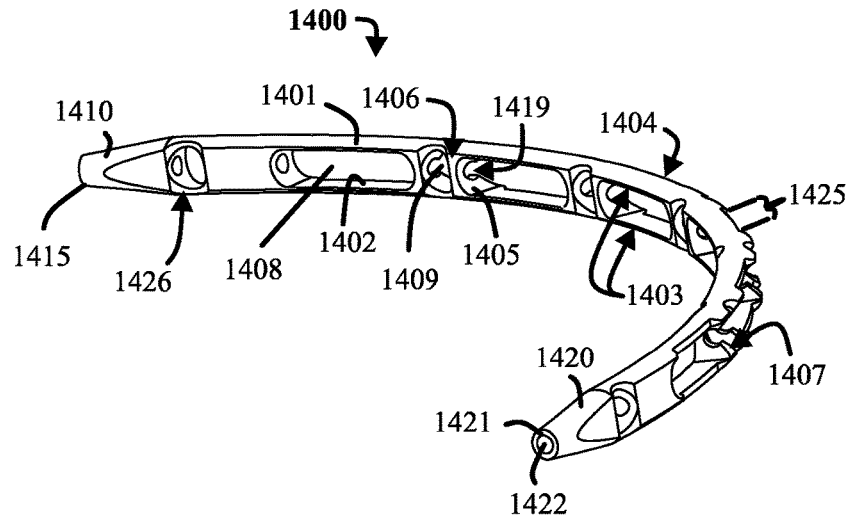
FIG. 14A is a perspective view of an embodiment of the aqueous humor outflow implants disclosed herein.
Figure 14B:
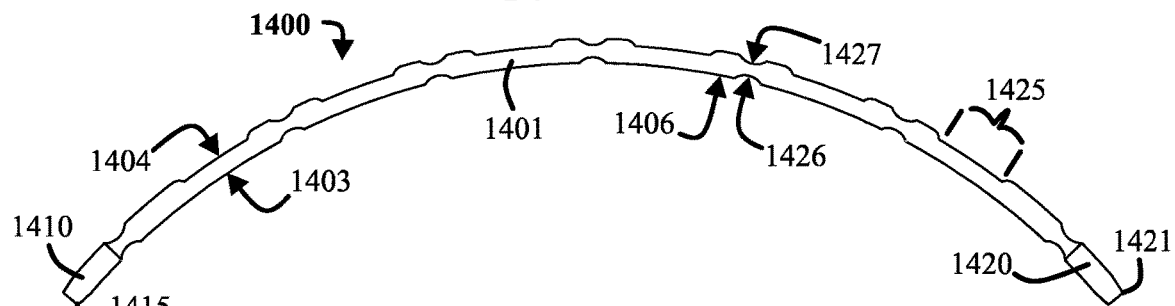
FIG. 14B is an overhead view of an embodiment of the aqueous humor outflow implants disclosed herein.
Figure 14C:
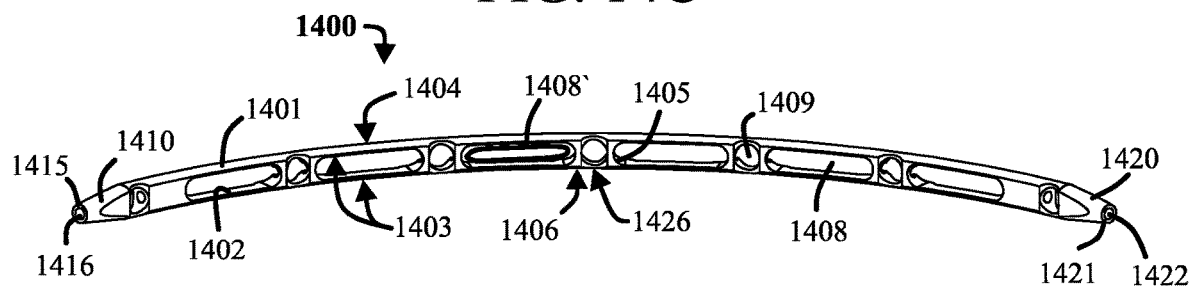
FIG. 14C is an anterior perspective view of an embodiment of the aqueous humor outflow implants disclosed herein.
Figure 14D:
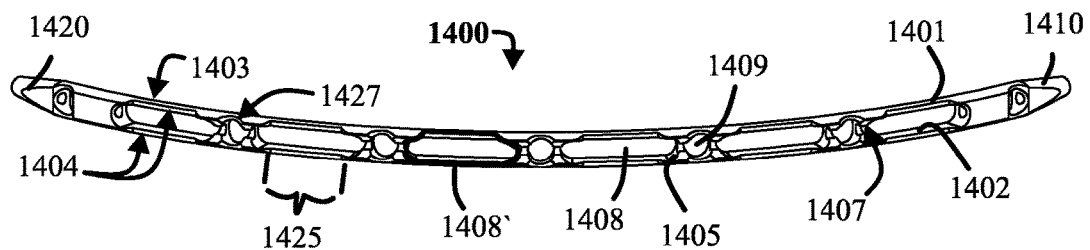
FIG. 14D is a posterior perspective view of an embodiment of the aqueous humor outflow implants disclosed herein.
Figure 14I:
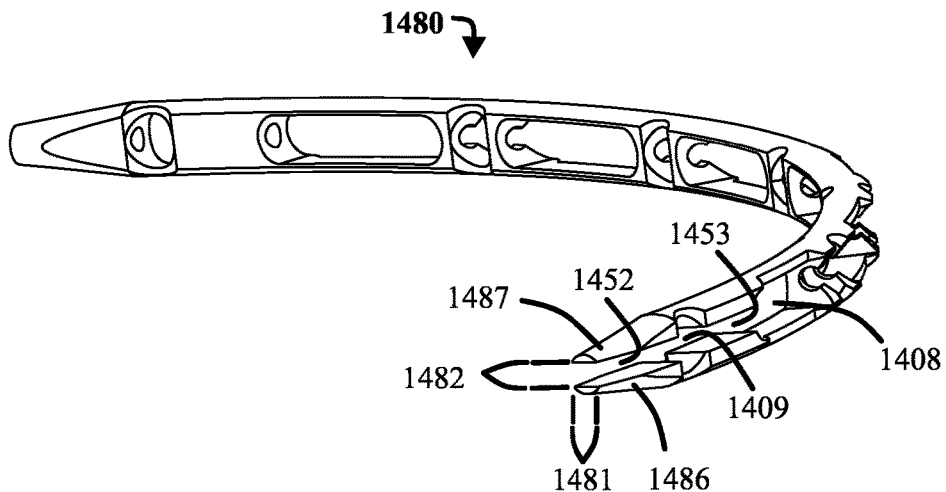
FIG. 14I is a perspective view of an embodiment of the aqueous humor outflow implants disclosed herein, in particular, with another alternative embodiment of an end thereof.
Figure 14J:
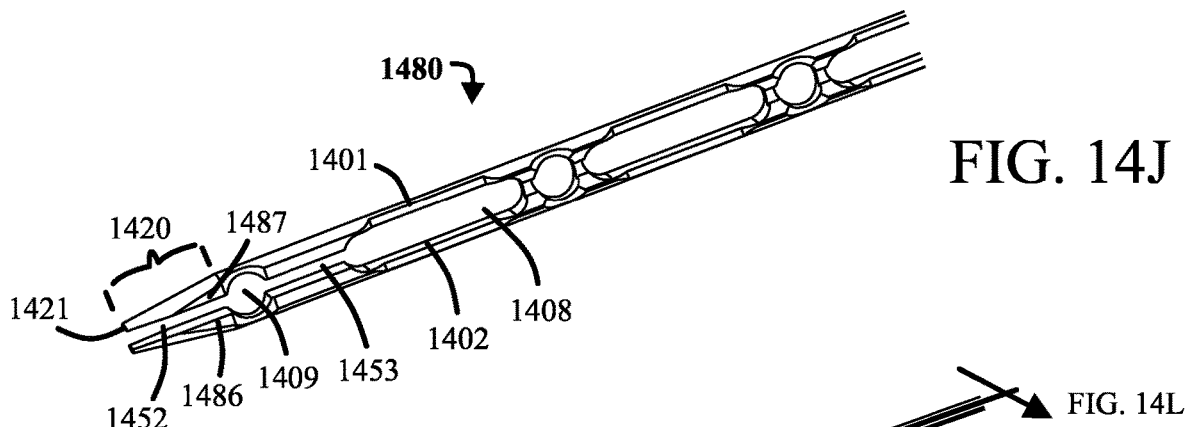
FIG. 14J is a posterior view of an embodiment of the aqueous humor outflow implants disclosed herein, in particular, with another alternative embodiment of an end thereof.
Figure 14K:
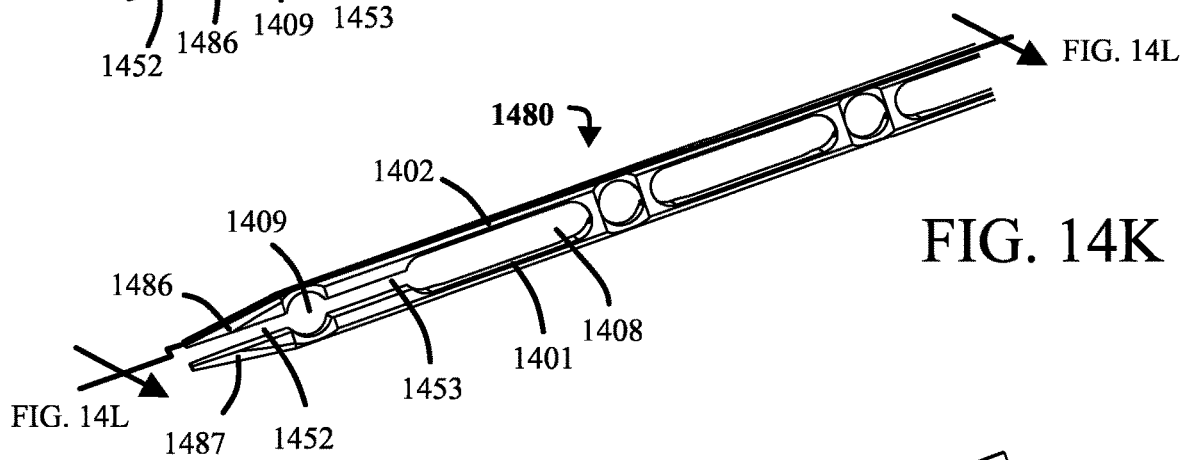
FIG. 14K is an anterior view of an embodiment of the aqueous humor outflow implants disclosed herein, in particular, with another alternative embodiment of an end thereof.
Figure 14L:
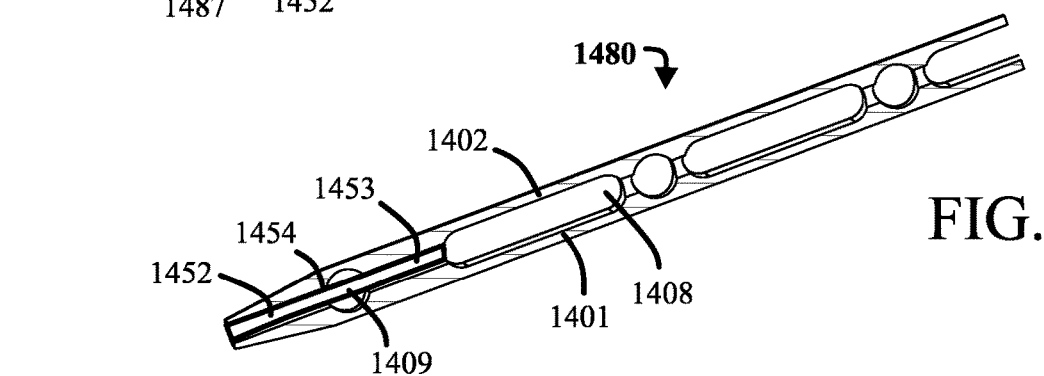
FIG. 14L is a cross-sectional view of an embodiment of the aqueous humor outflow implants disclosed herein, in particular, with another alternative embodiment of an end thereof.
Figure 14M:
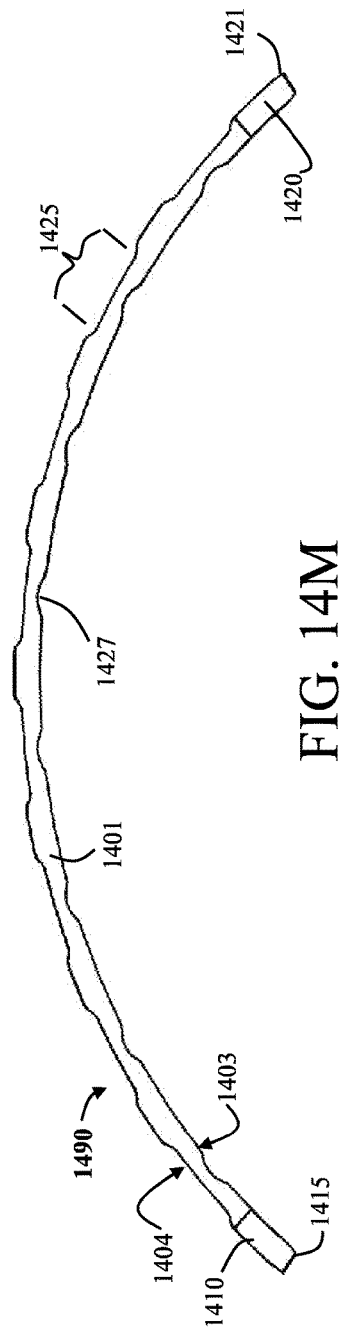
FIG. 14M is an overhead view of an embodiment of the aqueous humor outflow implants disclosed herein.
Figure 14N:
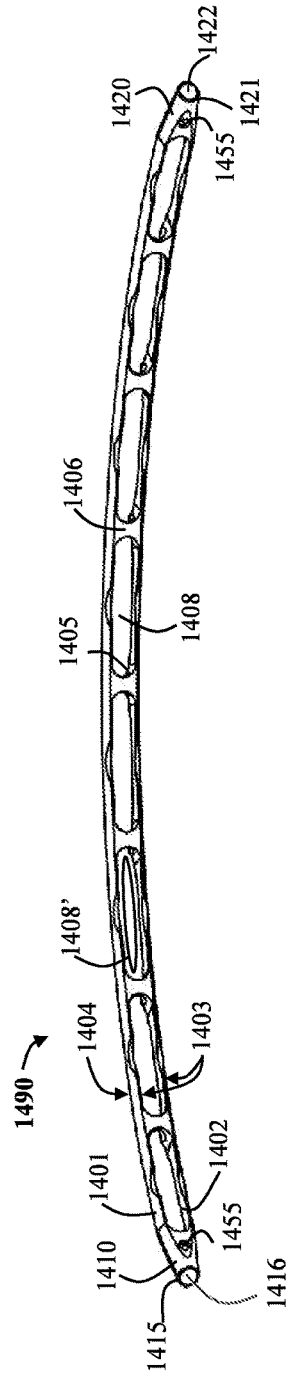
FIG. 14N is an anterior perspective view of an embodiment of the aqueous humor outflow implants disclosed herein.
Figure 14O:
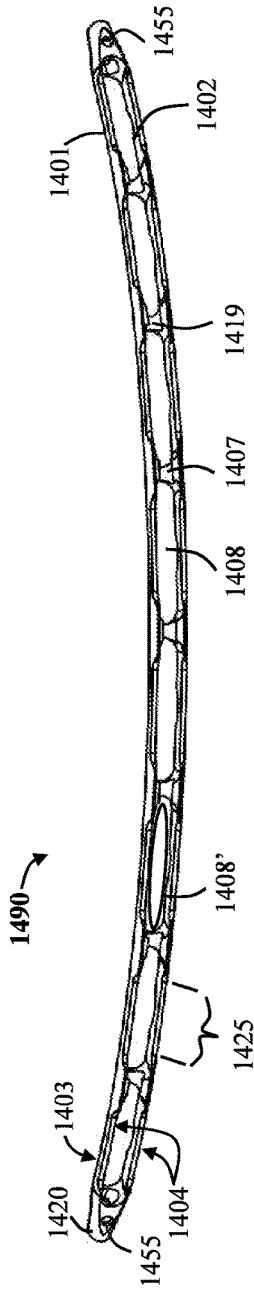
FIG. 14O is a posterior perspective view of an embodiment of the aqueous humor outflow implants disclosed herein.

An embodiment 1490 is depicted in FIGS. 14M, 14N and 14O. As in the aqueous humor outflow device in embodiments 600, 700, 800, 900, 1000, 1100, 1200 and 1300, the first and second arcuate rails 1401, 1402 and the structural components 1405, frame an opening 1408, which, when combined with the trabecular meshwork 108 and the posterior wall 122 of Schlemm's canal 110, forms an analogous chamber 1408'. Unlike the embodiments illustrated in FIGS. FIGS. 14A, 14B, 14C and 14D, structural components 1405 in embodiment 1490 do not frame one or more respective openings, e.g., circular opening 1409, normal to the longitudinal axis of the arcuate scaffold. That is, openings 1409 are absent in the embodiment 1490 illustrated in FIGS. 14M, 14N and 14O. However, the embodiment 1490 illustrated in FIGS. 14M, 14N and 14O comprises circular openings 1455 located proximate to or within each of ends 1410 and 1420. According to some embodiments, the circular openings 1455 enable an external device or secondary implant to be attached to either or both of ends 1410 and 1420. Like the embodiments 1000 and 1200 depicted in FIGS. 10A, 10B, 12A and 12B, the structural components 1405 (i.e., "posts") do not extend the full width between the anterior edges 1403 and posterior edges 1404 of the first and second arcuate rails 1401 and 1402. In particular, while the anterior edge 1406 of the structural components 1405 aligns with the anterior edges 1403 of the first and second arcuate rails 1401, 1402, the posterior edge 1407 of the structural components 1405 is recessed with respect to the posterior edges 1404 of the first and second arcuate rails 1401, 1402. Like the structural components 905, 1005, 1105, and 1205, structural components 1405 may further include openings 1419 along the longitudinal axis of the arcuate scaffold connecting adjacent openings or spaces 1408.

According to the embodiments 900, 1000, 1100, 1200, 1300, 1400 and 1490 depicted in FIGS. 9A, 9B 10A, 10B, 11A, 11B, 12A, 12B, 13A, 13B, 14A, 14B, 14C, 14D, 14M, 14N and 14O, the arcuate scaffold of the aqueous humor outflow device has a first end 910, 1010, 1110, 1210, 1310, 1410. The first end 910, 1010, 1110, 1210, 1310, 1410 also comprises a hole or opening 916, 1016, 1116, 1216, 1316, 1416 in an apex 915, 1015, 1115, 1215, 1315, 1415 to facilitate flow of aqueous humor. The first end is shaped as one of a polyhedron having a regular or an irregular polygon base, a cone or truncated cone having a base of any shape (e.g., curved, circular, an oval of some type, or irregular). For example, with reference to FIG. 15A, a base 1411 is curved where it meets the correspondingly curved first and second arcuate rails, and straight where it aligns with the respective anterior and posterior edges of the first and second arcuate rails. This is better illustrated in FIG. 16 where base 1411 is curved at 1412 where it meets the correspondingly curved first and second arcuate rails of the scaffold, and straight at 1413 where it aligns with the respective anterior and posterior edges of the first and second arcuate rails. According to the embodiments depicted in FIGS. 14M, 14N, and 14O, a circular opening 1455 is provided which can enable an external device or secondary implant to be attached to end 1410.

Figure 15A:
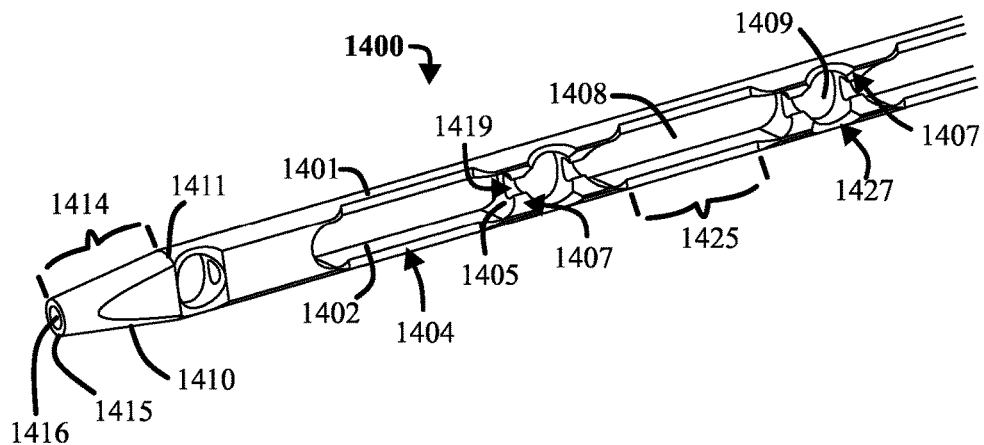
FIG. 15A is an enlarged posterior perspective view of one end of an embodiment.
Figure 15B:
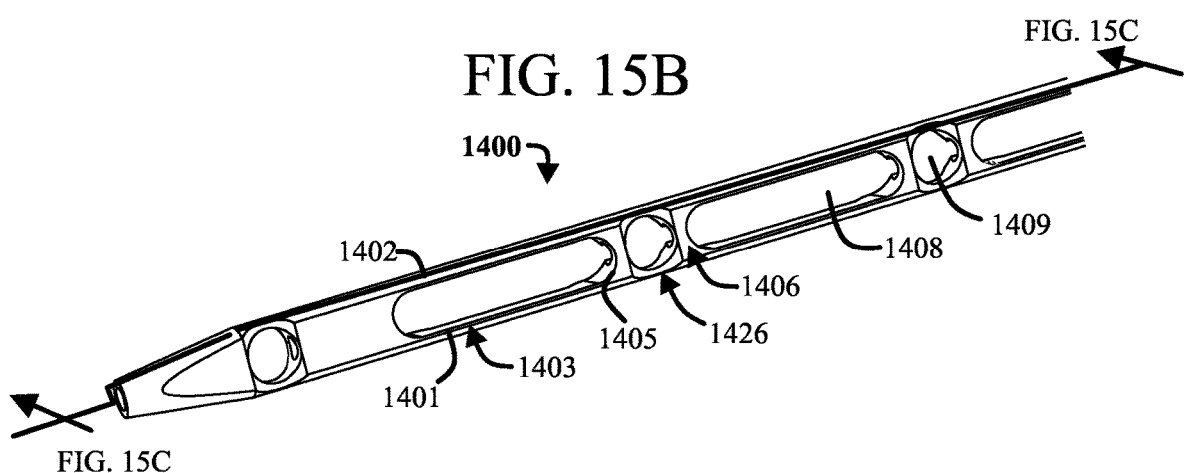
FIG. 15B is an enlarged anterior perspective view of one end of an embodiment.
Figure 15C:
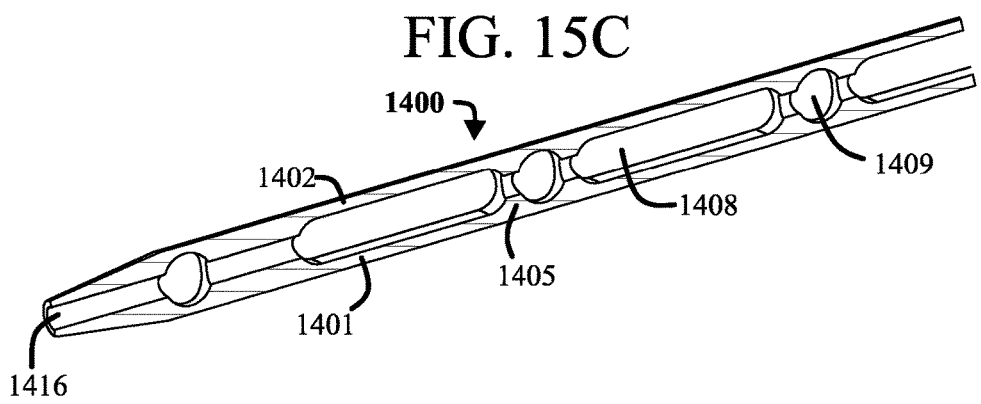
FIG. 15C is an enlarged perspective cross sectional view of one end of an embodiment.

As depicted in FIGS. 15A-15C, the base of the polyhedron or cone is in a plane normal to the longitudinal axis of the arcuate scaffold. The polyhedron or cone has a side 1414 extending along the longitudinal axis of the arcuate scaffold and converging, or tapering (either linearly or nonlinearly), toward an apex 1415 of the polyhedron or cone located outside a plane of the base. The embodiments depict the apex being centered with respect to the base. In other embodiments, it is appreciated the apex may be off-center with respect to the center of the base, whether in a superior, inferior, anterior or posterior direction with respect to the longitudinal axis of the scaffold. Further, while this embodiment depicts the base of the polyhedron or cone is in a plane normal to the longitudinal axis of the arcuate scaffold, in other embodiments the base is in a plane substantially normal to the longitudinal axis of the arcuate scaffold, or in a plane offset at an angle with respect to a plane normal to the longitudinal axis.

According to the embodiments, the arcuate scaffold having a first end, whether shaped as a cone, truncated cone, or polyhedron, that tapers to an apex, enables introduction of the arcuate scaffold into the Schlemm's canal 110, and the dilation thereof as the Schlemm's canal 110 widens to accommodate the increasing cross-sectional area of the scaffold as the scaffold is inserted into the Schlemm's canal 110. Similarly, in an alternative embodiment, the arcuate scaffold having a first end that tapers to an apex enables introduction of the arcuate scaffold into one of the one or more collector channels 123 that originate in the posterior wall 122 of the Schlemm's canal 110, via collector channel entrances 121, and dilations thereof. Likewise the tapered first end facilitates translation of the arcuate scaffold inside the Schlemm's canal 110, that is, the tapered first end facilitates movement within a three-dimensional space (x, y and z directions), including movement back and forth. According to an embodiment, sufficient tapering of the first end further enables piercing, or controlled repiercing, of the trabecular meshwork 108. It is appreciated that piercing of the trabecular meshwork 108 might be desirable upon insertion of the implant device. Once the implant device is in the Schlemm's canal 110 it is important that it not pierce through the trabecular meshwork 108 other than under intentional control of the implant device.

Figure 16:
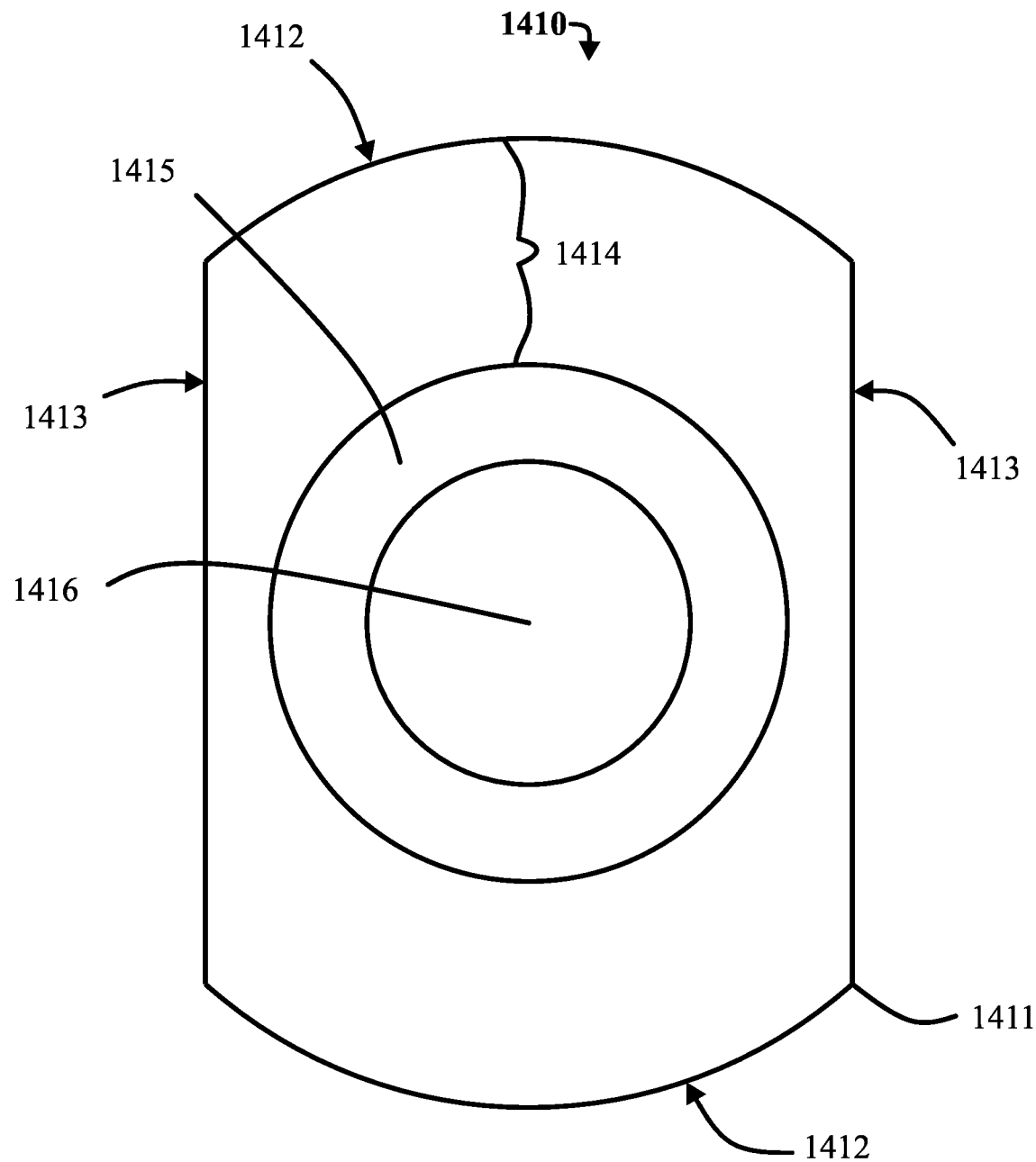
FIG. 16 is an enlarged elevation view of an end of the aqueous humor implant device according to embodiments of the invention.

With reference to FIG. 16, according to the embodiments 1400 and 1490 depicted in FIGS. 14A-14O and 14M-14O, the arcuate scaffold of the aqueous humor outflow device has a first end 1410 with an apex 1415 comprising a hole or opening 1416 through which to allow flow of aqueous humor to or from one of: the Schlemm's canal 110, one of the collector channels 123, or a device (such as another aqueous humor outflow device) positioned adjacent to, abutting, coupled, or docked with the aqueous humor outflow device.

According to the embodiments 900, 1000, 1100, 1200, 1300, 1400 and 1490 depicted in FIGS. 9A, 9B 10A, 10B, 11A, 11B, 12A, 12B, 13A, 13B, 14A, 14B, 14C, 14D and 14M-14O, the arcuate scaffold of the aqueous humor outflow device has a second end 920, 1020, 1120, 1220, 1320, 1420 opposite from the first end along the longitudinal axis of the arcuate scaffold. In the embodiments depicted, the second end is shaped similarly to the first end, as one of a polyhedron having a regular or an irregular polygon base, a cone or truncated cone having a base of any shape. According to an embodiment of the aqueous humor outflow device, the second end of the arcuate scaffold is shaped similarly as the first end, thereby providing a degree of symmetry so that the arcuate scaffold can be inserted into the Schlemm's canal 110 from either direction, with all the attendant benefits and applications, such as enabling introduction of the arcuate scaffold from the second end into the Schlemm's canal 110, and the dilation thereof as the Schlemm's canal 110 widens to accommodate the increasing cross-sectional area of the scaffold as the scaffold is inserted into the Schlemm's canal 110. Likewise, the tapered second end facilitates translation of the arcuate scaffold inside the Schlemm's canal 110, that is, the tapered second end facilitates movement within a three-dimensional space (x, y and z directions), including movement back and forth. The tapered second end also enables piercing the trabecular meshwork 108. As mentioned above, such an embodiment is capable of piercing the trabecular meshwork 108 during entry from the anterior chamber into Schlemm's canal 110 but once in the Schlemm's canal 110, the tip should not unintentionally pierce back through trabecular meshwork 108 into the anterior chamber. It is appreciated that ends 910, 1010, 1110, 1210, 1310, 1410 or 920, 1020, 1120, 1220, 1320, 1420, in alternative embodiments, may not be tapered. For example, one or both ends may be straight, or substantially straight, along its length (cylindrical or with straight parallel sides). In such embodiments, the tip of the end may be slightly tapered or rounded. According to the embodiments depicted in FIGS. 14M, 14N, and 14O, a circular opening 1455 is provided which can enable an external device or secondary implant to be attached to end 1420.

Figure 13G:
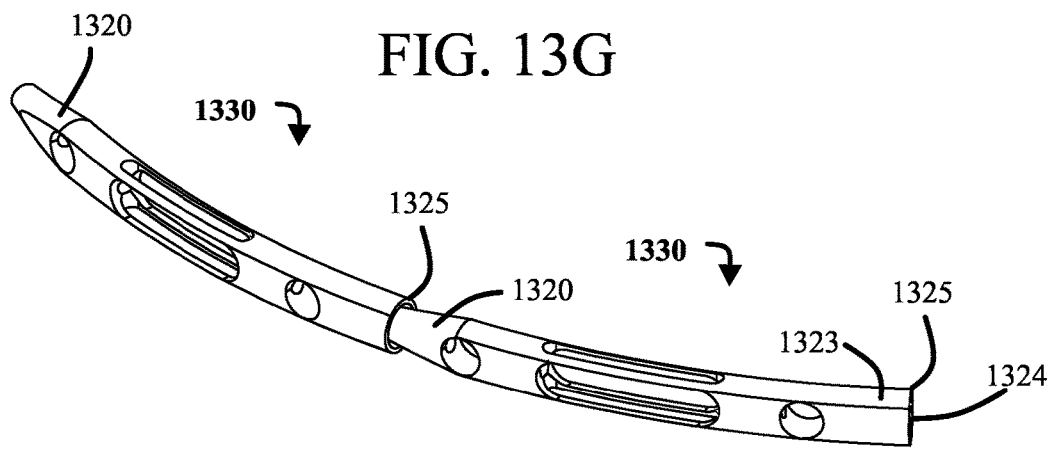
FIG. 13G is a posterior perspective view of a pair of aqueous humor outflow implants according to an alternative embodiment disclosed herein.
Figure 13H:
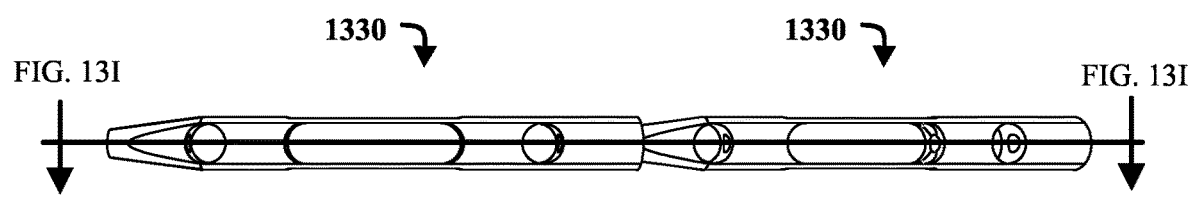
FIG. 13H is a posterior elevation view of a pair of aqueous humor outflow implants according to an alternative embodiment disclosed herein.
Figure 13I:
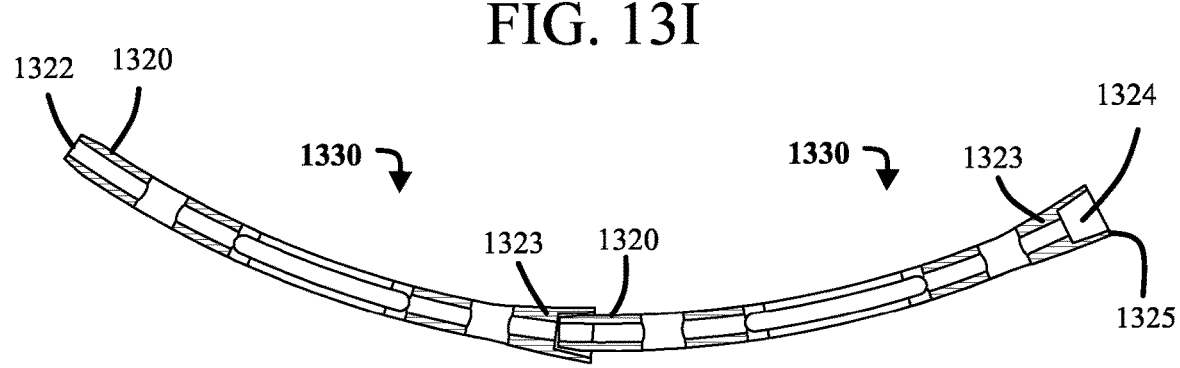
FIG. 13I is an overhead sectional view of a pair of aqueous humor outflow implants according to an alternative embodiment disclosed herein.

According to an alternative embodiment 1330, as illustrated in FIGS. 13C-13I, a flared end 1323 of a first aqueous humor outflow device 1330 allows for docking with a second aqueous humor outflow device, by insertion of a tapered or non-tapered end of the second aqueous humor outflow device into a space or cavity 1324 within the flared end 1323 of the first aqueous humor outflow device. In this embodiment, the flare is present in an anterior-posterior orientation, as more easily viewed on FIGS. 13F and 13I. FIGS. 13C-13I depict an embodiment 1330 of a first aqueous humor outflow device with a flared end 1323 that has a space or cavity 1324 and a flared, concave tip 1325 that act as a "guide" to accept an end of a second aqueous humor outflow device. The first aqueous humor outflow device is already positioned within Schlemm's canal 110, according to this embodiment, and then an end of the second aqueous humor outflow device passes through the tip 1325 and into the cavity 1324 of flared end 1323 of the first aqueous humor outflow device. Once an end of the second aqueous humor outflow device is docked in space 1324 of flared end 1323 of the first aqueous humor outflow device, as depicted in FIGS. 13G-13I, and the second aqueous humor outflow device within Schlemm's canal 110, manipulation of the second aqueous humor outflow device (by surgical instrumentation or insertion device) allows for controlled translational movement of both the first and second aqueous humor outflow devices. In this manner a properly docked second aqueous humor outflow device is used to position the first aqueous humor outflow device into a portion of the Schlemm's canal 110 that cannot be easily accessed by current gonioscopic surgical techniques. Additional aqueous humor outflow devices could be implanted in Schlemm's canal 110 behind the second aqueous humor outflow device paired to or docked with the first aqueous humor outflow device to achieve additional clinical benefit. It should be understood that embodiment 1330 can also be docked with a first aqueous humor outflow device with a tapered end by coupling the first aqueous humor outflow device with a flared end 1323 of embodiment 1330. That is, other embodiments described herein, such as embodiments 900, 1000, 1100, 1300, 1400, 1490, may be modified so that one or both ends of the embodiments are flared in a manner similar to end 1323 in embodiment 1300. In this manner embodiment 1330 or similar embodiments thereof may be used to push the aqueous humor outflow devices already implanted into Schlemm's canal 110 further along the canal regardless of the tip geometry (tapered, straight, or flared, symmetric or asymmetric) of the first aqueous humor outflow device.

According to an alternative embodiment (not depicted), a non-tapered end, e.g., a straight end (cylindrical or with straight parallel sides), of a first aqueous humor outflow device 1330 allows for docking with a second aqueous humor outflow device 1330, by insertion of a tapered end 1310 or 1320 of the second aqueous humor outflow device into the space or cavity 1324 within the straight end of the first aqueous humor outflow device. In such an embodiment of an aqueous humor outflow device 1330, the end 1323 is straight along its length from its base to its tip 1325.

Just as in the case of the first end of the aqueous humor outflow device, according to one embodiment, the second end 720, 920, 1020, 1120, 1220, 1320, 1420 also comprises a hole or opening 722, 922, 1022, 1122, 1222, 1322, 1422 in an apex 721, 921, 1021, 1121, 1221, 1321, 1421 to facilitate flow of aqueous humor. The hole in the apex at both ends of the arcuate scaffold, as discussed further below, can be used to interact with a delivery device mechanism.

FIG. 14E is a perspective view of an embodiment 1450 of the aqueous humor outflow implants disclosed herein, in particular, with an alternative embodiment of the end 1420. Embodiment 1450 is characterized by a continuous longitudinal slot (depicted by dotted line 1454 in FIG. 14H) in the arcuate scaffold that opens or extends from the anterior side through to the posterior side of the arcuate scaffold, and extends from the opening 1408 closest to end 1420 through to nearly the tip or apex 1421 of end 1420. The longitudinal slot comprises two portions 1452 and 1453 on either side of the opening 1409 closest to end 1420. Portion 1453 of the longitudinal slot 1454 extends from the closest opening 1408 to the closest opening 1409. Portion 1452 extends from closest opening 1409 to just short of apex 1421. An annular ring 1451 is formed at apex 1421, and hole 1422 is present, as in embodiments 1400 and 1490.

It is appreciated that embodiment 1450 also or alternatively provides for slot 1454 at end 1410. In any case, it is thought that slot 1454 in embodiment 1450 improves the flow of aqueous humor through the embodiment in Schlemm's canal 110.

FIG. 14F is a posterior view of the same embodiment 1450 depicted in FIG. 14E. FIG. 14G is an anterior view of embodiment 1450 further illustrating the longitudinal slot extends from the anterior side through to the posterior side of the arcuate scaffold. FIG. 14H provides a cross-sectional view of embodiment 1450.

A variation of embodiment 1450, not shown in the figures, is characterized by a discontinuous longitudinal slot 1454 in the arcuate scaffold. The slot still opens or extends from the anterior side through to the posterior side of the arcuate scaffold, and extends from the opening 1408 closest to end 1420 through to nearly the tip or apex 1421 of end 1420, but may include one or more structural supports between top and bottom rails 1401 and 1402.

FIG. 14I is a perspective view of an embodiment 1480 of the aqueous humor outflow implants disclosed herein, in particular, with another alternative embodiment of an end 1420. Embodiment 1480 is characterized by a longitudinal slot (depicted by dotted line 1454 in FIG. 14L) in the arcuate scaffold that opens or extends from the anterior side through to the posterior side of the arcuate scaffold, and extends from the opening 1408 closest to end 1420 through the tip or apex 1421 of end 1420. The longitudinal slot comprises two portions 1452 and 1453 on either side of the opening 1409 closest to end 1420. Portion 1453 of the longitudinal slot 1454 extends from the closest opening 1408 to the opening 1409 closest to apex 1421. Portion 1452 extends from closest opening 1409 to apex 1421. Unlike embodiment 1450, no annular ring 1451 is formed at apex 1421, and there is, necessarily then, no hole 1422. Rather, the slot continues through apex 1421. Doing so creates a top portion 1487 of end 1420 that is separated by a distance 1482 from a corresponding bottom portion 1486 of end 1420. The slot at the apex 1421 has a width of distance 1481 that substantially corresponds with the diameter of hole 1422 or annular ring 1451 in embodiment 1450.

It is appreciated that embodiment 1480 also or alternatively provides for slot 1454 at end 1410. In any case, it is thought that slot 1454 in embodiment 1480 improves the flow of aqueous humor through embodiment 1480 in Schlemm's canal 110.

FIG. 14J is a posterior view of the same embodiment 1480 depicted in FIG. 14I. FIG. 14K is an anterior view of embodiment 1480 further illustrating the longitudinal slot extends from the anterior side through to the posterior side of the arcuate scaffold. FIG. 14L provides a cross-sectional view of embodiment 1480.

A variation of embodiment 1480, not shown in the figures, is characterized by a discontinuous longitudinal slot 1454 in the arcuate scaffold. The slot still opens or extends from the anterior side through to the posterior side of the arcuate scaffold, and extends from the opening 1408 closest to end 1420 through the tip or apex 1421 of end 1420, but may include one or more structural supports between top and bottom rails 1401 and 1402.

Figure 25A:
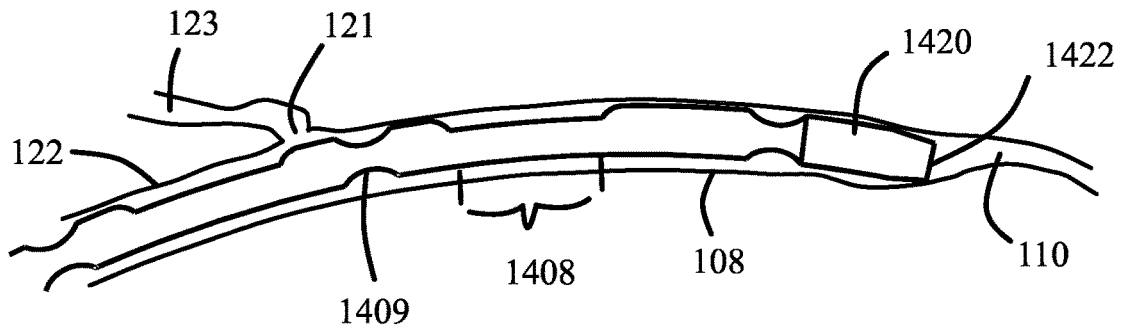
FIG. 25A is an enlarged overhead view of the end or tip of an embodiment fully implanted within the Schlemm's canal.
Figure 25B:
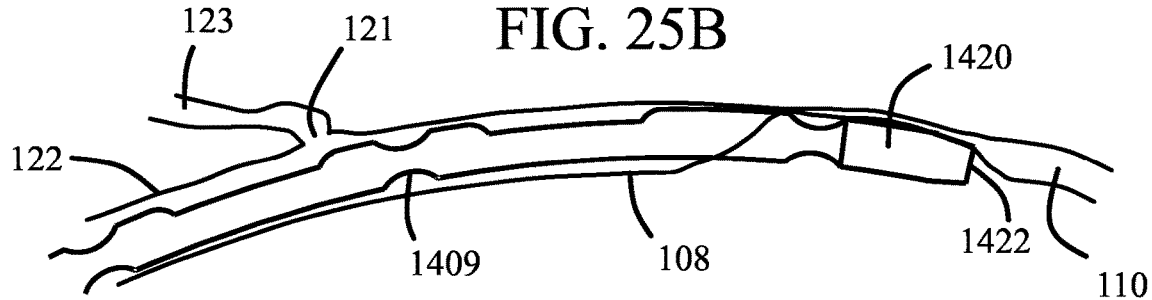
FIG. 25B is an enlarged overhead view of the end or tip of an embodiment positioned within the Schlemm's canal demonstrating the tip positioned through the trabeculotomy, anterior to trabecular meshwork, but still within the angle depression formed by Schlemm's canal.
Figure 25C:
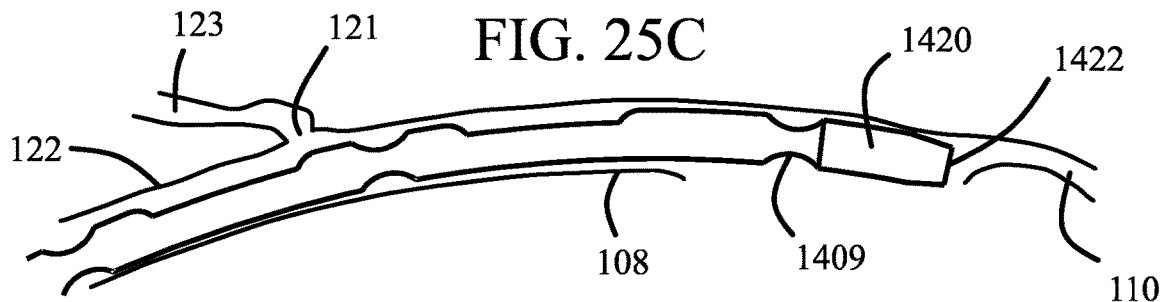
FIG. 25C is an enlarged overhead view of the end or tip of an embodiment demonstrating exposure of the terminal inlet and tip sideport through a small trabeculotomy allowing direct aqueous flow into the implant openings.

In both of the embodiments 1450 depicted in FIGS. 14E-14H and 1480 depicted in FIGS. 14I-14L, it is contemplated that the aqueous humor outflow device, when implanted, will be positioned within Schlemm's canal 110, no matter the location of the end 1420, which may be positioned underneath the trabecular meshwork 108, or exposed through a trabeculotomy (as, for example, depicted in FIG. 25C). It is also contemplated that during insertion of the aqueous humor outflow device a portion of the tip may not be fully inserted through a trabeculotomy (either by intention or not) so that the tip is anterior to the trabecular meshwork 108 even though still within the channel formed by Schlemm's canal 110, or may be pressing the anterior surface of the trabecular network into Schlemm's canal 110 (as, for example, depicted in FIG. 25B).

It is contemplated that the trailing end 1420 of the embodiments 1450 and 1480 of the aqueous humor outflow device may be anterior to the trabecular meshwork 108 or be exposed by a trabeculotomy that was created to implant the device, when the device is in position in Schlemm's canal 110. Doing so provides better flow into the aqueous humor outflow device through the trabeculotomy or through the portion of device that is anterior to the trabecular meshwork 108 even though the device itself is situated within the Schlemm's canal 110.

According to an embodiment of the aqueous humor outflow device, the first and second arcuate rails provide a docking station or port within the respective anterior edges of the first and second arcuate rails in which to insert and dock, position, or retain in a stable position (either permanently or removably retained), an implant device, also referred to herein as a secondary implant device (the aqueous humor outflow device being the primary implant device, ("primary implant" herein below). According to embodiments, the secondary implant device may be: 1) an ocular anterior chamber implant device; 2) an ocular support device, a device intended to support or attach to other structures within the eye whether natural or synthetic, such as an intraocular lens, an iris or iris prosthesis, an iris clip/hook, a capsular bag or capsular bag support device; or 3) a non-ocular support device, such as a drug eluting device, a drug delivery device, a sensor device, a transducer device, a gene/vector delivery device, a trabecular microbypass device, an intrascleral implant, a suprachoroidal/supraciliary implant, a fluid injection device, an ultrasound energy emitting device, a radio frequency emitting device, or an electromagnetic wave emitting device. It is appreciated that the above discussed manufacturing processes for, and possible functional coatings, on the aqueous humor outflow device are equally applicable to the secondary implant device.

Figure 17:
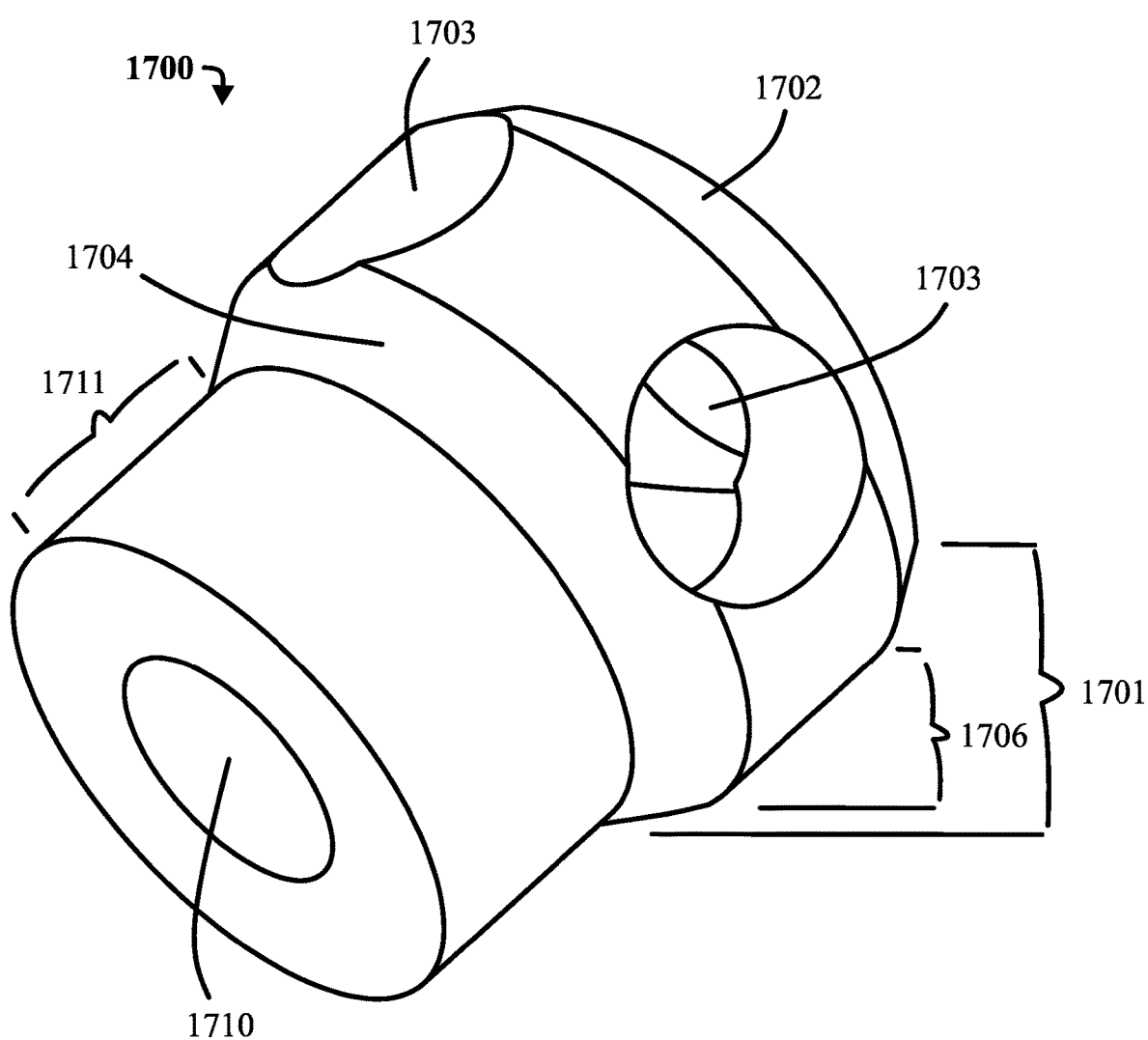
FIG. 17 is a perspective view of an embodiment of one of the secondary implants discussed herein.
Figure 19A:
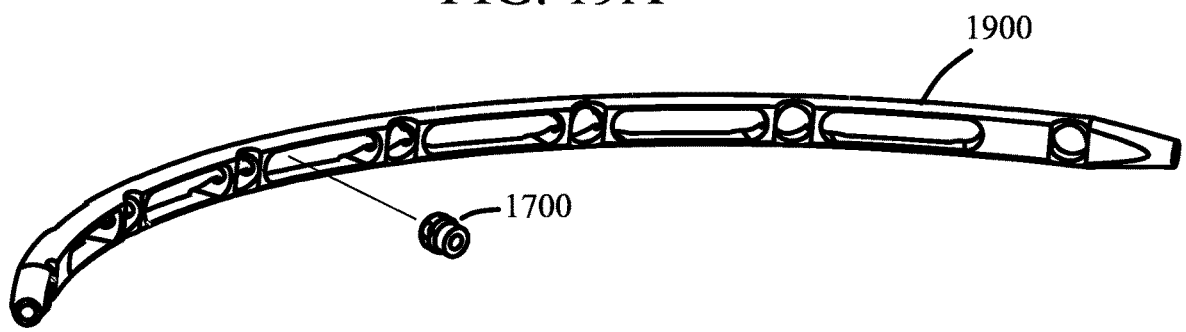
FIG. 19A is a perspective view of a primary implant and a secondary implant prior to docking of the secondary implant onto the primary implant according to embodiments of the invention.
Figure 19B:
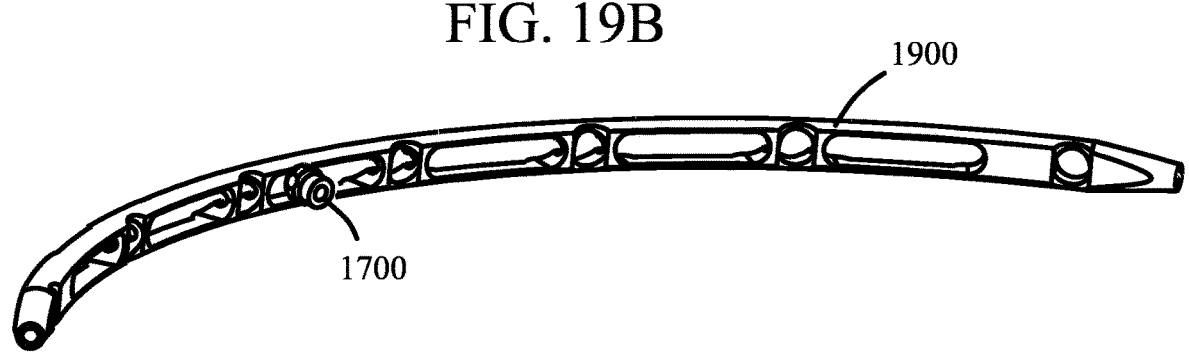
FIG. 19B is a perspective view of the primary implant and the secondary implant after docking of the secondary implant onto the primary implant according to embodiments of the invention.
Figure 19C:
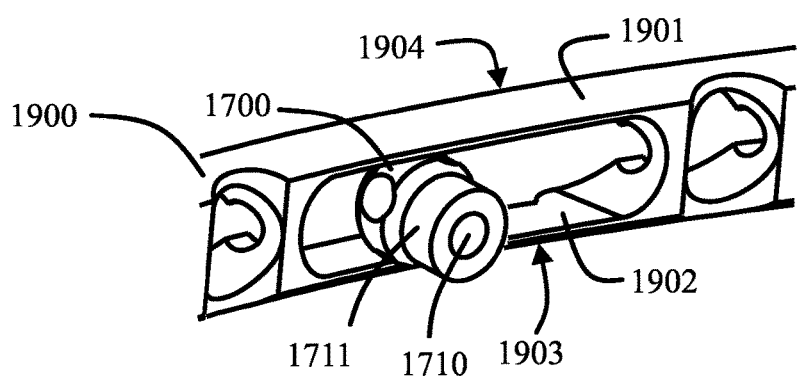
FIG. 19C is an enlarged perspective view of the primary implant and the secondary implant after docking of the secondary implant onto the primary implant according to embodiments of the invention.

FIG. 17 is a perspective view of an embodiment of one of the secondary implants 1700 discussed herein. In particular, FIG. 17 depicts a secondary implant 1700 with a bulbous head 1701. FIG. 19A is a perspective view of the primary implant 1900 and the secondary implant according to embodiment 1700 prior to docking of the secondary implant 1700 onto the primary implant 1900 according to embodiments of the invention. FIG. 19B depicts a perspective view of the primary implant 1900 and the secondary implant according to embodiment 1700 after docking of the secondary implant 1700 onto the primary implant 1900. FIG. 19C is an enlarged perspective view of the primary implant 1900 and a secondary implant according to embodiment 1700 after docking of the secondary implant 1700 onto the primary implant 1900. The bulbous head 1701 is tapered at 1702 to ease insertion of the secondary implant 1700 between the respective anterior edges of the first and second arcuate rails 1904, 1903. The bulbous head 1701 is likewise tapered at 1704. The distance between the anterior edges, and the distance between the posterior edges, of the first and second arcuate rails of the primary implant 1900 is less than the diameter of the bulbous head 1701 at its largest circumference 1706 for the secondary implant 1700. When the secondary implant 1700 is inserted into the primary implant 1900, at an angle substantially normal to the longitudinal axis of the primary implant, the bulbous head 1701 at its largest circumference 1706 engages the inside surfaces of first and second arcuate rails 1901, 2101, 1902, 2102, and the secondary implant 1700 is thereby held in position, by frictional and/or compressive forces. Additionally, or alternatively, according to one embodiment, the secondary implant 1700 is removably positioned within the respective anterior and posterior edges of respective windows in the first and second arcuate rails (such as windows 1128, 1328, 2128 for respective embodiments 1100, 1300 and 2100 illustrated in FIGS. 11A, 13A and 21A-C). Additionally, or alternatively, according to one embodiment, the secondary implant 1700 is removably positioned within the respective anterior and posterior edges of the first and second arcuate rails 1901 and 1902 and held in place at least in part by pressure provided by the trabecular meshwork 108.

One or more through holes 1703 allows for aqueous humor to flow through the secondary implant once it is in place in the arcuate scaffold. As discussed above with reference at least to embodiments 600, 700, 800, 900, 1000, 1100, 1200, 1400 and 1490, as depicted in FIGS. 6A, 6B, 7A, 7B, 8A, 8B, 9A, 9B, 10A, 10B, 11A, 11B, 12A, 12B, 14A-14D, 14M-14O and 15A-15C, the arcuate scaffold (primary implant) 600, 700, 800, 900, 1000, 1100, 1200, 1400 and 1490, allows for the flow of the aqueous humor through the open area in a direction generally along the longitudinal axis of the arcuate scaffold 600, 700, 800, 900, 1000, 1100, 1200, 1400 and 1490 when inserted in the Schlemm's canal 110, in particular, within and between chambers 131 of the Schlemm's canal 110 or analogous chambers 1408' to the one or more collector channels 123 that originate in the posterior wall 122 of the Schlemm's canal 110 when inserted in the Schlemm's canal 110. Through hole 1703 maintains continuity in the open area in a direction generally along the longitudinal axis of the arcuate scaffold 600, 700, 800, 900, 1000, 1100, 1200, 1400 and 1490 even when the secondary implant 1700 is in position between the first and second arcuate rails 601, 701, 801, 901, 1001, 1101, 1201, 1401, 602, 702, 802, 902, 1002, 1102, 1202 and 1402. It is appreciated that the secondary implant 1700 may need to be rotated upon insertion so that a through hole 1703 substantially aligns with the open area 608, 708, 808, 908, 1008, 1108 1208 and 1408 in a direction generally along the longitudinal axis of the arcuate scaffold 600, 700, 800, 900, 1000, 1100, 1200, 1400 and 1490, depending on the number and position of the through holes 1703 in a particular embodiment.

It is further appreciated that while the embodiment 1700 depicted in FIG. 17 is generally circular in geometry, other geometries would also work, such as an oval or substantially oval geometry in which a length of the oval along a first axis through a cross section of the secondary implant is longer than a width of the oval along a second axis through the cross section of the secondary implant normal to the first axis. The secondary implant may be inserted and then rotated as required, e.g., 90 degrees, after insertion so that the length of the oval, which may be greater than the distance between the respective anterior and posterior edges 603, 703, 803, 903, 1003, 1103, 1203, 1403, 604, 704, 804, 904, 1004, 1104, 1204, 1404 of the first and second arcuate rails 601, 701, 801, 901, 1001, 1101, 1201, 1401, 602, 702, 802, 902, 1002, 1102, 1202, 1402 of the primary implant, engages the respective posterior edges 604, 704, 804, 904, 1004, 1104, 1204, 1404 of the first and second arcuate rails 601, 701, 801, 901, 1001, 1101, 1201, 1401, 602, 702, 802, 902, 1002, 1102, 1202, 1402 to hold the secondary implant 1700 in position. According to another embodiment, the secondary implant has a square or rectangular cross section.

According to the embodiments 1400 and 1490 of the aqueous humor outflow device, the respective posterior edges 1404 are recessed as depicted at 1425, where directly opposite the frame openings 1408. In particular, according to one embodiment of the aqueous humor outflow device, the respective posterior edges 1404 are recessed, as depicted at 1425, directly opposite the general location of the respective anterior edges of the first and second arcuate rails into which the secondary implant device is inserted. The posterior edges 1404 are recessed anteriorly in order to protect the posterior wall 122 of Schlemm's canal 110 from traumatic damage from either the posterior edge of the rail or from that portion of the secondary implant that is secured in place posterior to the rail. Likewise, with reference to FIGS. 14D and 15A, a portion of the respective posterior edges 1404 is recessed as depicted at 1427, where directly opposite the frame openings 1409. In particular, according to one embodiment of the aqueous humor outflow device, the respective posterior edges 1404 are recessed anteriorly, as depicted at 1427, in order to limit the amount of contact between the posterior edges 1404 of the rails and the posterior wall 122 of Schlemm's canal 110, thereby further protecting the posterior wall 122 of Schlemm's canal 110 from traumatic damage from the posterior edge of the rail.

The recession as depicted at 1427 also provides for an area of preferred articulation, i.e., bending, of the preferred embodiment as the recession narrows the width of the top and bottom rails at the recession's location along the rails. While an anterior recession is depicted at 1427 as being located along the posterior edge of the first and second accurate rails, it is appreciated that a posterior recession as depicted at 1426 may be located at one or more locations along an anterior edge of the first and second accurate rails, or both the anterior and posterior edges of the first accurate and second accurate rails may accommodate respective posterior and anterior recessions. One of the purposes of the one or more recessions is to allow the embodiment to articulate at the locations of the recession(s) so as to accommodate varying sizes of Schlemm's canals across a population of Schlemm's canals that may have different radii, wherein the radii is defined by the radius of the Schlemm's canal in the horizontal plane with radius drawn from the center of the vertical axis of the pupil of the eye and the end of the radius terminating at either the anterior wall of Schlemm's canal, the posterior wall of Schlemm's canal, or at some point on the horizontal plane between the anterior and posterior walls of Schlemm's canal.

The embodiments 1400 and 1490 may have an external device or a secondary implant device attached to its first and/or second ends that may have diagnostic or therapeutic functions either related or unrelated to the regulation of aqueous humor outflow. The tips or apexes thereof, or holes therein, provide a docking station or port in which to insert and dock, position, or retain in a stable position (either permanently or removably retained), an implant device, also referred to herein as a secondary implant device (the aqueous humor outflow device being the primary implant device). In one embodiment, the secondary implant provides for injection or delivery of a fluid into the hole of the first or second ends. In an embodiment, the injected fluid may pass through the structure and egress from the opposite end. Additionally, the embodiments 1400 and 1490 may have as a secondary implant device an ultrasonic frequency signal emitting element or device attached to its first or second ends to provide for the delivery of an ultrasonic signal into the embodiment such that the embodiment transfers the ultrasonic signal into Schlemm's Canal during or after implantation of the embodiment into Schlemm's canal. Additionally, the embodiments 1400 and 1490 may have as a secondary implant device a radio frequency (RF) signal emitting element or device attached to its first or second ends to provide for the delivery of an RF signal into the embodiment such that the embodiment transfers the RF signal into Schlemm's Canal during or after the implantation of the embodiment into Schlemm's canal.

Embodiment 1700 includes a portion 1711 that extends in an anterior direction normal to the longitudinal axis of the arcuate scaffold 1000, 1200, 1400 and 1490. In one embodiment, the portion 1711 extends through the trabecular meshwork 108 and into the ocular anterior chamber when the secondary implant 1700 is positioned in the primary implant 1000, 1200, 1400 and 1490.

According to one embodiment, the secondary implant has a hole or opening or portal 1710 via which aqueous humor can flow, depending on the length of the secondary implant 1700, from the anterior chamber, or from the trabecular meshwork 108, into the secondary implant 1700. The hole 1710 is connected to one or more through holes 1703 so that the flow of aqueous humor received via hole 1710 can flow through the open area in the arcuate scaffold 1000, 1200, 1400 and 1490 in a direction generally along the longitudinal axis of the arcuate scaffold 1000, 1200, 1400 and 1490 even when the secondary implant 1700 is in position between the first and second arcuate rails 1001, 1201, 1401, 1002, 1202, 1402.

Figure 18:
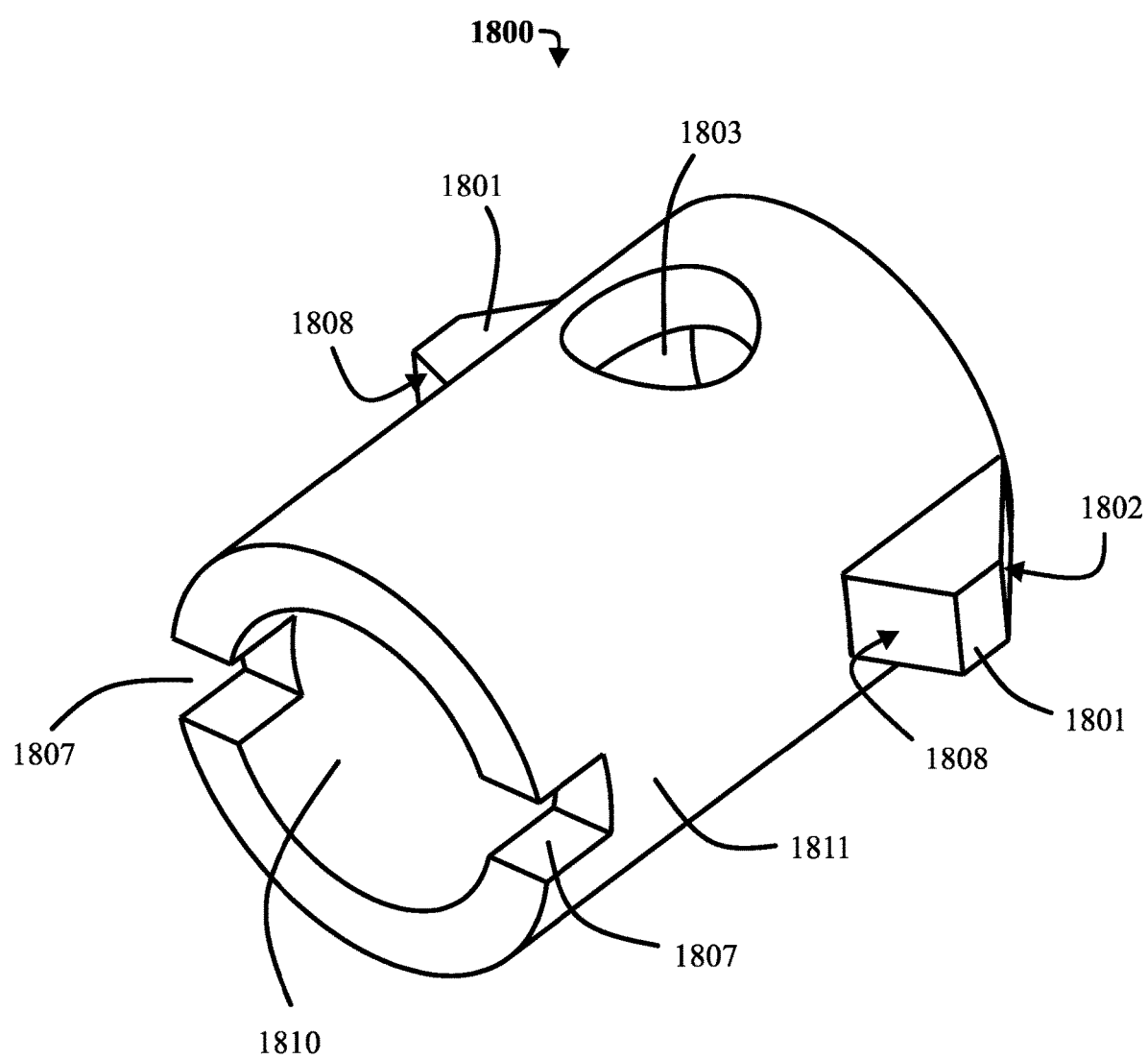
FIG. 18 is a perspective view of an embodiment of one of the secondary implants discussed herein.

FIG. 18 is a perspective view of an embodiment 1800 of one of the secondary implants discussed herein. In particular, FIG. 18 depicts a secondary implant with wings 1801. The wings are tapered at 1802 to ease insertion of the secondary implant between the respective anterior edges 603, 703, 803, 903, 1003, 1103, 1203, 1303, 1403 of the first and second arcuate rails 601, 701, 801, 901, 1001, 1101, 1201, 1301, 1401, 602, 702, 802, 902, 1002, 1102, 1202, 1302, 1402. The distance between the anterior edges of the first and second arcuate rails of the primary implant is less than the width of the secondary implant 1800 from the tip of one wing 1801 to the tip of the other wing 1801.

According to embodiment 1800, the secondary implant is inserted into the primary implant with wings 1801 substantially aligned with the longitudinal axis of the primary implant 700, 1100, 1200, 1300. The secondary implant is then rotated substantially 90 degrees so that the wings are docked into the windows 728, 1128, 1228, 1328 present within the first and second arcuate rails 701, 1101, 1201, 1301, 702, 1102, 1202, 1302, and the secondary implant is thereby held in position. Alternatively, with regard to primary implants such as embodiments 600, 800, 900, 1000, 1400, 1490, which lack windows in the first and second arcuate rails 601, 801, 901, 1001, 1401, 602, 802, 902, 1002, 1402 the secondary implant is inserted into the primary implant with wings 1801 substantially normal to the longitudinal axis of the primary implant. When the secondary implant is so inserted into the primary implant, the tapered edges 1802 of wings 1801 engage the respective anterior edges 603, 803, 903, 1003, 1403 of the first and second arcuate rails 601, 801, 901, 1001, 1401, 602, 802, 902, 1002, 1402 resulting in flexion of the rails away from the implant. Continued insertion of the secondary implant results in the anterior edges 1808 of the wings 1801 passing beyond the posterior edges 604, 804, 904, 1004, 1404 of the arcuate rails allowing the rails to substantially return to their original resting position effectively locking the anterior edges 1808 of the secondary implant wings 1801 against the posterior edges 604, 804, 904, 1004, 1404 of the first and second arcuate rails 601, 801, 901, 1001, 1401, 602, 802, 902, 1002, 1402.

One or more through holes 1803 allows for aqueous humor to flow through the secondary implant once it is in place in the arcuate scaffold. Through holes 1803 maintain continuity in the open area in a direction generally along the longitudinal axis of the arcuate scaffold even when the secondary implant is in position between the first and second arcuate rails. It is appreciated that the secondary implant may be rotated upon insertion so that a through hole 1803 substantially aligns with the open area in a direction generally along the longitudinal axis of the arcuate scaffold.

It is further appreciated that while the embodiment 1800 depicted in FIG. 18 is generally circular in geometry, other geometries would also work, such as an oval or substantially oval geometry in which a length of the oval along a first axis through a cross section of the secondary implant is longer than a width of the oval along a second axis through the cross section of the secondary implant normal to the first axis, with the wings 1801 affixed along the first axis. The secondary implant may be inserted and then, if needed, rotated after insertion, e.g., rotated 90 degrees after insertion, so that the length of the oval, including the wings, which may be greater than the distance between the respective anterior and posterior edges of the first and second arcuate rails of the primary implant, engages the respective posterior edges of the first and second arcuate rails to hold the secondary implant in position.

Embodiment 1800 includes a portion 1811 that extends in an anterior direction normal to the longitudinal axis of the arcuate scaffold. In one embodiment, the portion 1811 extends through the trabecular meshwork 108 and into the ocular anterior chamber when the secondary implant is positioned in the primary implant.

According to one embodiment, the secondary implant has a hole or opening or portal 1810 via which aqueous humor can flow from the anterior chamber, or from the trabecular meshwork 108, into the secondary implant. The hole 1810 is connected to the through holes 1803 so that the flow of aqueous humor received via hole 1810 can flow through the open area in the arcuate scaffold in a direction generally along the longitudinal axis of the arcuate scaffold even when the secondary implant is in position between the first and second arcuate rails. Embodiment 1800 also includes a slotted section 1807 in opening 1810. (It is appreciated that embodiment 1700 may also include such a slotted section.) The slotted section facilitates receiving an insertion device or tool keyed to the slotted section, in the similar way that a flathead screw receives a flathead screwdriver. It is appreciated that there may be other configurations for the opening 1810 to receive a corresponding tool, such as an internal hex, square recess, or star configurations.

Figure 20A:
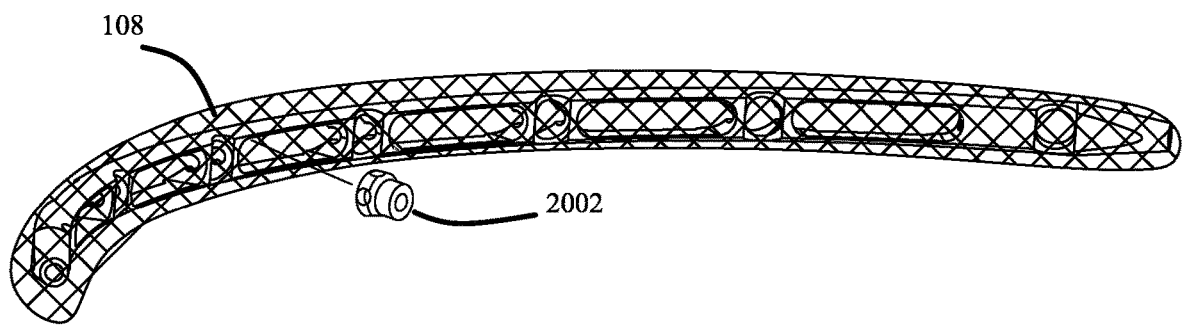
FIG. 20A is a perspective view of the primary implant positioned within the Schlemm's canal behind the trabecular meshwork, and a secondary implant positioned in the anterior chamber prior to docking of the secondary implant onto the primary implant according to embodiments of the invention.
Figure 20B:
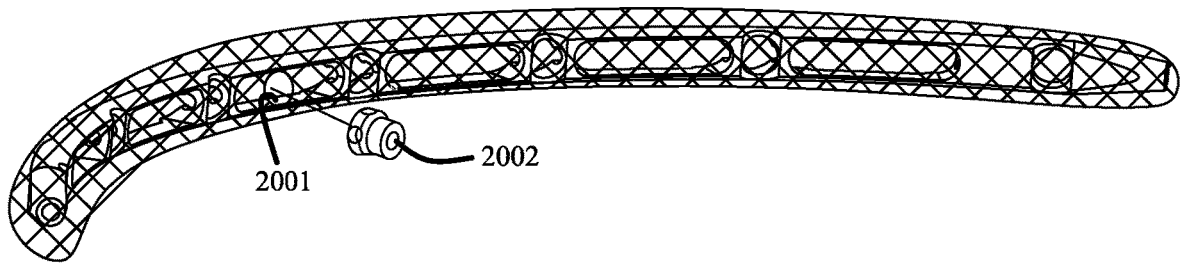
FIG. 20B is a perspective view of the primary implant positioned within the Schlemm's canal behind the trabecular meshwork, and the secondary implant positioned in the anterior chamber prior to docking of the secondary implant through the trabecular meshwork onto the primary implant demonstrating the trabeculotomy through which the secondary implant would be placed according to embodiments of the invention.
Figure 20C:
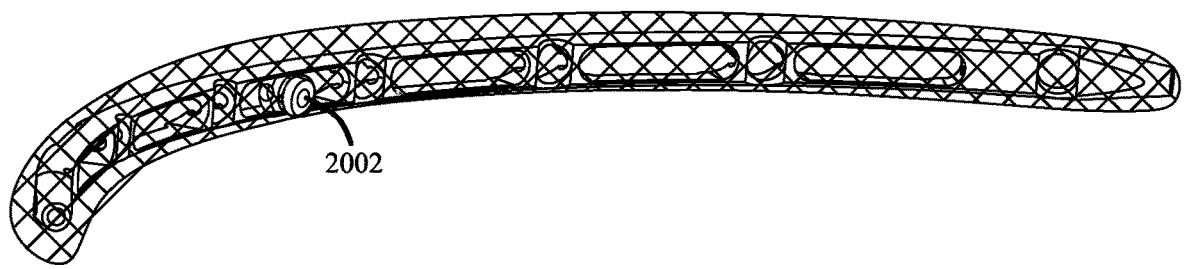
FIG. 20C is an perspective view of the primary implant positioned within the Schlemm's canal behind the trabecular meshwork, and the secondary implant after docking of the secondary implant through the trabecular meshwork onto the primary implant according to embodiments of the invention.
Figure 20D:
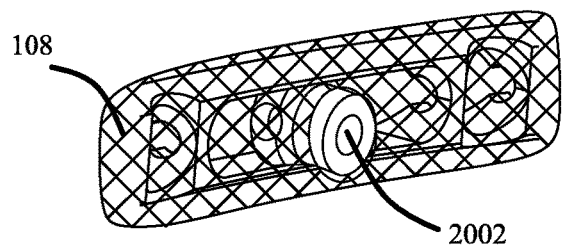
FIG. 20D is an enlarged perspective view of the primary implant positioned within the Schlemm's canal behind the trabecular meshwork, and the secondary implant after docking of the secondary implant through the trabecular meshwork onto the primary implant according to embodiments of the invention.

FIGS. 20A and 20B provide perspective views of the primary implant 2001 positioned within the Schlemm's canal 110 behind the trabecular meshwork 108, and a secondary implant 2002 positioned in the ocular anterior chamber prior to docking of the secondary implant 2002 onto the primary implant 2001 according to embodiments of the invention. FIG. 20B illustrates an opening in trabecular meshwork 108 (also referred to as a "trabeculotomy") created with a surgical instrument or insertion device or by the secondary implant 2002 during placement of the secondary implant 2002 through the trabecular meshwork 108 between the first and second rails of the aqueous humor outflow device within Schlemm's canal 110. FIG. 20C is a perspective view of the primary implant 2001 positioned within the Schlemm's canal 110 behind the trabecular meshwork 108, and the secondary implant 2002 after docking of the secondary implant 2002 through the trabecular meshwork 108 onto the primary implant 2001 according to embodiments of the invention. FIG. 20D is an enlarged perspective view of the primary implant 2001 positioned within the Schlemm's canal 110 behind the trabecular meshwork 108, and the secondary implant 2002 after docking of the secondary implant 2002 through the opening in the trabecular meshwork 108 onto the primary implant 2001 according to embodiments of the invention. The distance between the anterior edges, and the distance between the posterior edges, of the first and second arcuate rails of the primary implant 2001 is less than the diameter of the head of the secondary implant 2002 at its largest circumference. When the secondary implant 2002 is inserted into the primary implant 2001, at an angle substantially normal to the longitudinal axis of the primary implant, the head of the secondary implant at its largest circumference engages the inside surfaces of first and second (i.e., top and bottom) arcuate rails, and the secondary implant 2002 is thereby held in position, by frictional and/or compressive forces.

Figure 21A:
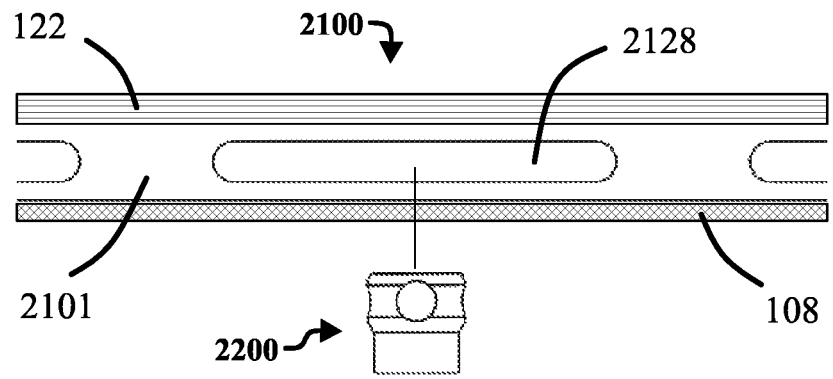
FIG. 21A is an enlarged overhead view of the primary implant positioned within the Schlemm's canal behind the trabecular meshwork, and a secondary implant positioned in the anterior chamber prior to docking of the secondary implant onto the primary implant according to embodiments of the invention.
Figure 21B:
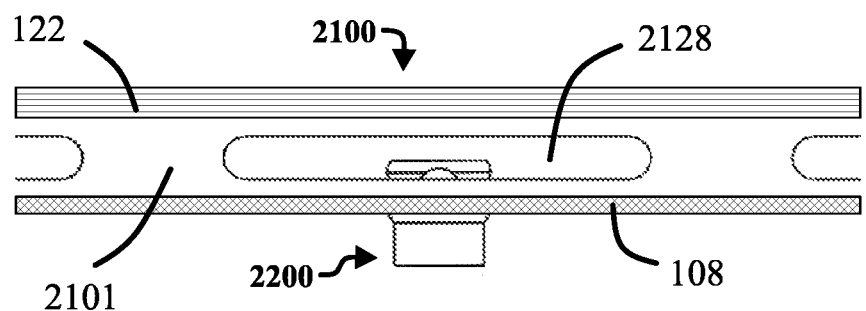
FIG. 21B is an enlarged overhead view of the primary implant positioned within the Schlemm's canal behind the trabecular meshwork, and the secondary implant during docking of the secondary implant through the trabecular meshwork onto the primary implant according to embodiments of the invention.
Figure 21C:
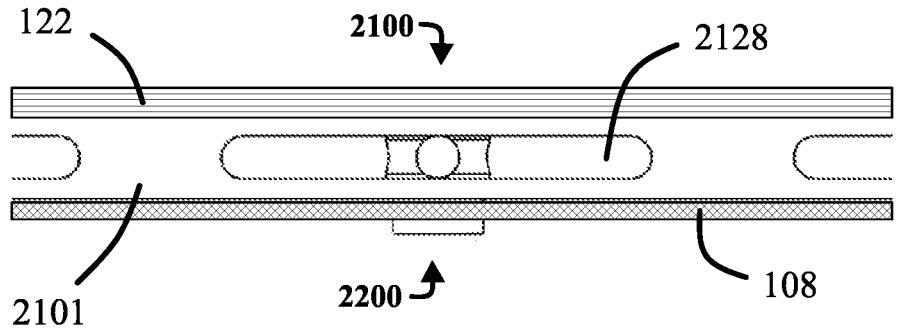
FIG. 21C is an enlarged overhead view of the primary implant positioned within the Schlemm's canal behind the trabecular meshwork, and the secondary implant after docking of the secondary implant through the trabecular meshwork onto the primary implant according to embodiments of the invention.

FIG. 21A is an enlarged overhead view of an embodiment of the primary implant 2100 positioned within the Schlemm's canal 110 behind the trabecular meshwork 108, and a secondary implant 2200 positioned in the anterior chamber prior to docking of the secondary implant 2200 onto the primary implant 2100 according to embodiments of the invention. As can be seen looking through window 2128 in the top (first arcuate) rail 2101, as the secondary implant has yet to be inserted or docked onto the primary implant, the space between the first arcuate rail 2101 and second arcuate rail (not visible in the top down view) is empty. FIG. 21B is an enlarged overhead view of the primary implant 2100 positioned within the Schlemm's canal 110 behind the trabecular meshwork 108, and the secondary implant 2200 during docking of the secondary implant 2200 through the trabecular meshwork 108 onto the primary implant 2100 according to embodiments of the invention. As can be seen looking through window 2128 in the top (first arcuate) rail 2101, since the secondary implant is in the process of being inserted or docked onto the primary implant, the space 2108 between the first and second arcuate rails is partially filled with the secondary implant. FIG. 21C is an enlarged overhead view of the primary implant 2100 positioned within the Schlemm's canal 110 behind the trabecular meshwork 108, and the secondary implant 2200 after docking of the secondary implant through the trabecular meshwork 108 onto the primary implant according to embodiments of the invention. As can be seen looking through window 2128 in the top (first arcuate) rail 2101, now that the secondary implant is fully inserted or docked onto the primary implant, the space between the first and second arcuate rails shows the secondary implant docked in position. In this manner, according to one embodiment, the secondary implant 2200 is removably positioned within the respective anterior and posterior edges of window 2128 in the first and second arcuate rails.

Figure 22A:
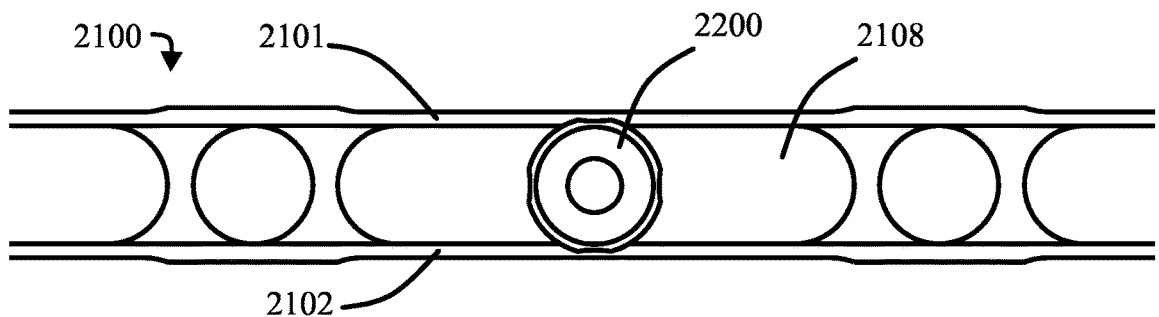
FIG. 22A is an enlarged front view of the primary implant, and a secondary implant positioned adjacent to the primary implant prior to docking of the secondary implant onto the primary implant according to embodiments of the invention.
Figure 22B:
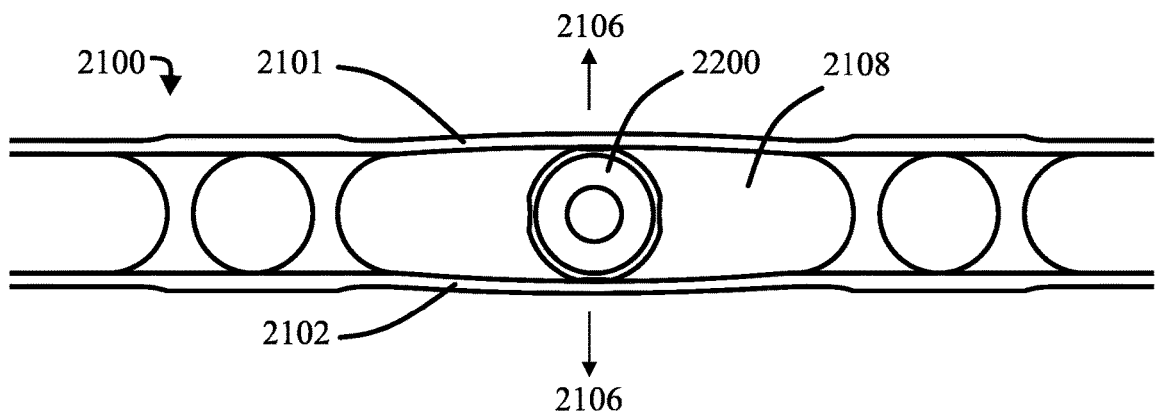
FIG. 22B is an enlarged front view of the primary implant, and a secondary implant during docking of the secondary implant onto the primary implant showing flexion of the rails away from the secondary implant, according to embodiments of the invention.
Figure 22C:
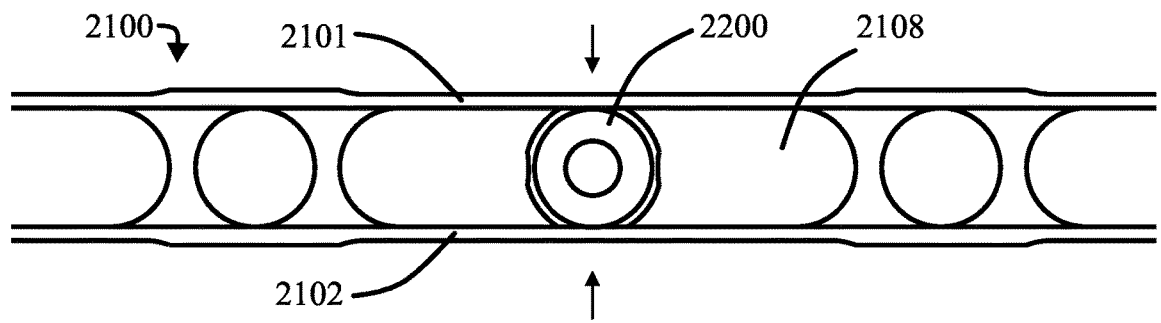
FIG. 22C is an enlarged front view of the primary implant, and a secondary implant after docking of the secondary implant onto the primary implant showing return of the rails to their resting position effectively locking the secondary implant onto the primary implant, according to embodiments of the invention.

As discussed above, according to an embodiment, the first and second arcuate rails 2101, 2102 provide a guide or opening between which to insert the secondary implant device 2200. In one embodiment, the first and second arcuate rails 2101, 2102 flex to allow insertion of the secondary implant device 2200. FIG. 22A is an enlarged front view of the primary implant 2100, with the secondary implant 2200 positioned adjacent to the primary implant 2100 prior to docking of the secondary implant 2200 onto the primary implant 2100 according to embodiments of the invention. As the secondary implant has yet to be inserted or docked onto the primary implant, the space 2108 between the first and second arcuate rails 2101, 2102 is empty. FIG. 22B is an enlarged front view of the primary implant 2100, and a secondary implant 2200 during docking of the secondary implant onto the primary implant showing flexion 2106 of the first and second arcuate rails 2101, 2102 away from the secondary implant 2200, according to embodiments of the invention. FIG. 22B depicts the space 2108 between the first and second arcuate rails 2101, 2102 in which the secondary implant is in the process of being inserted or docked onto the primary implant. FIG. 22C is an enlarged front view of the primary implant 2100, and the secondary implant 2200 after docking of the secondary implant 2200 onto the primary implant 2100 showing substantial return of the rails to their original resting position effectively locking the secondary implant 2200 onto the primary implant 2100, according to embodiments of the invention. FIG. 22C depicts the space 2108 between the first and second arcuate rails 2101, 2102 in which the secondary implant 2200 is fully and finally inserted or docked onto the primary implant 2100.

Figure 23A:
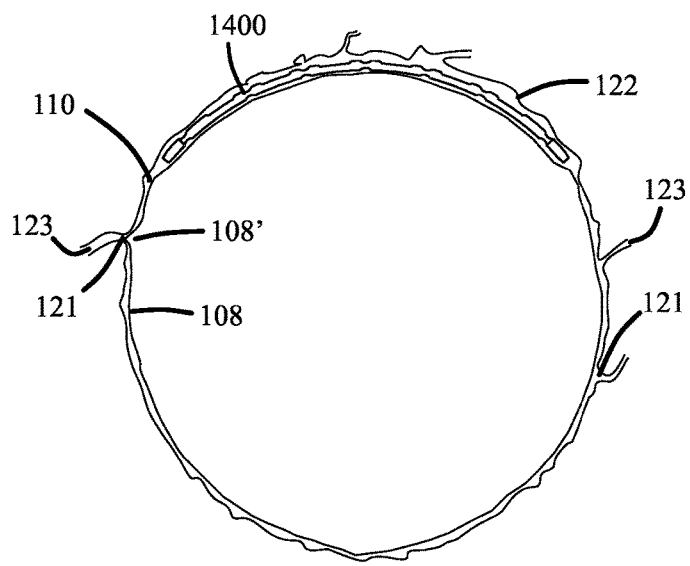
FIG. 23A is an overhead view of a Schlemm's canal with an embodiment of the arcuate scaffold implanted into the Schlemm's canal, according to an embodiment.
Figure 23B:
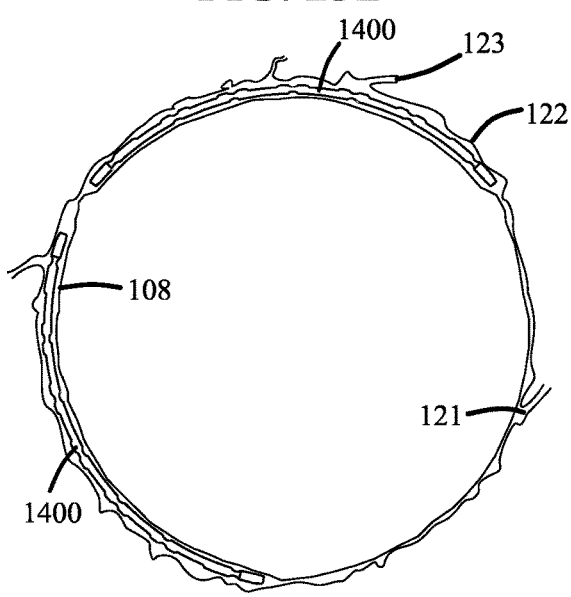
FIG. 23B is an overhead view of a Schlemm's canal with two embodiments of the arcuate scaffold implanted into the canal, according to an embodiment.
Figure 23C:
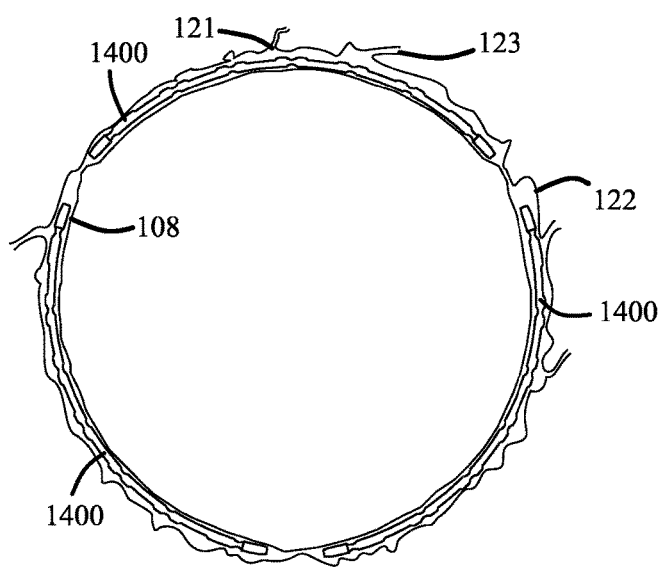
FIG. 23C is an overhead view of a Schlemm's canal with three embodiments of the arcuate scaffold implanted into the canal, according to an embodiment.

FIGS. 23A-23C depict an overhead view of a Schlemm's canal 110 with one or more arcuate scaffolds implanted into the canal 110, according to embodiments of the invention. In particular, FIG. 23A illustrates a single arcuate scaffold, according to embodiment 1400, or embodiment 1490 (not shown), implanted into the canal 110. As also discussed above with reference to FIG. 5C, the trabecular meshwork 108 is collapsed onto the posterior wall 122 of the Schlemm's canal 110 limiting circumferential flow. Insertion of an arcuate scaffold, as depicted in FIG. 23A, remedies the collapse of the trabecular meshwork 108 onto the posterior wall 122 of the Schlemm's canal 110, thereby improving circumferential flow at least in that portion of the Schlemm's canal 110 in which the arcuate scaffold is present. The trabecular meshwork 108 may also herniate 108' into the collector channel entrance 121 blocking flow of aqueous humor into the collector channel 123, as depicted in FIG. 5C and FIG. 23A. Insertion of a second arcuate scaffold, as depicted in FIG. 23B, remedies the herniation 108' of the trabecular meshwork 108 into the collector channel entrance 121, thereby improving aqueous humor flow from at least that portion of the Schlemm's canal 110 in which the second arcuate scaffold is present to the collector channel entrance 121. Insertion of a third arcuate scaffold, as depicted in FIG. 23C, in addition to the insertion of the first and second arcuate scaffolds, remedies the collapse of the trabecular meshwork 108 onto the posterior wall 122 of the Schlemm's canal 110 along substantially the entire circumference of the Schlemm's canal 110, thereby improving circumferential flow in the Schlemm's canal 110.

Figure 24A:
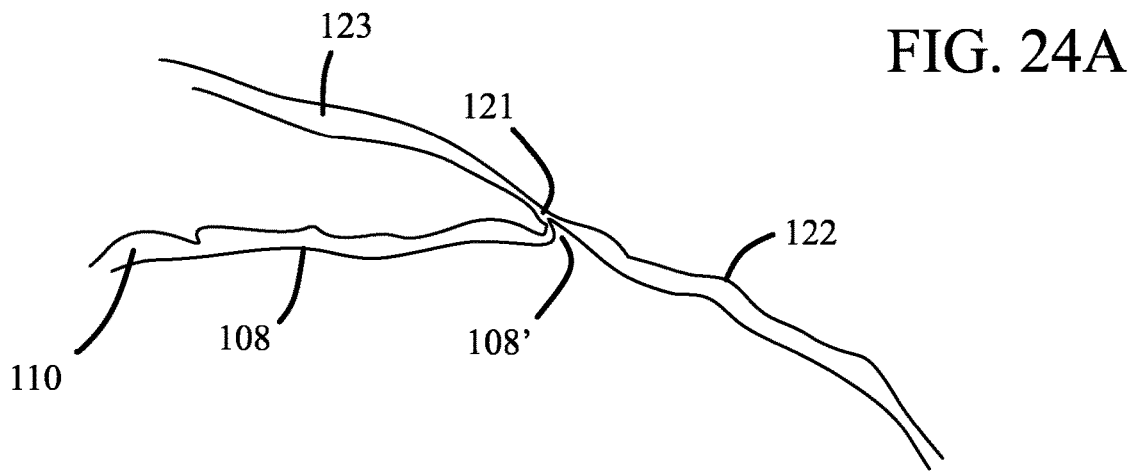
FIG. 24A is an enlarged overhead view of a Schlemm's canal with herniation of trabecular meshwork into a collector channel opening.
Figure 24B:
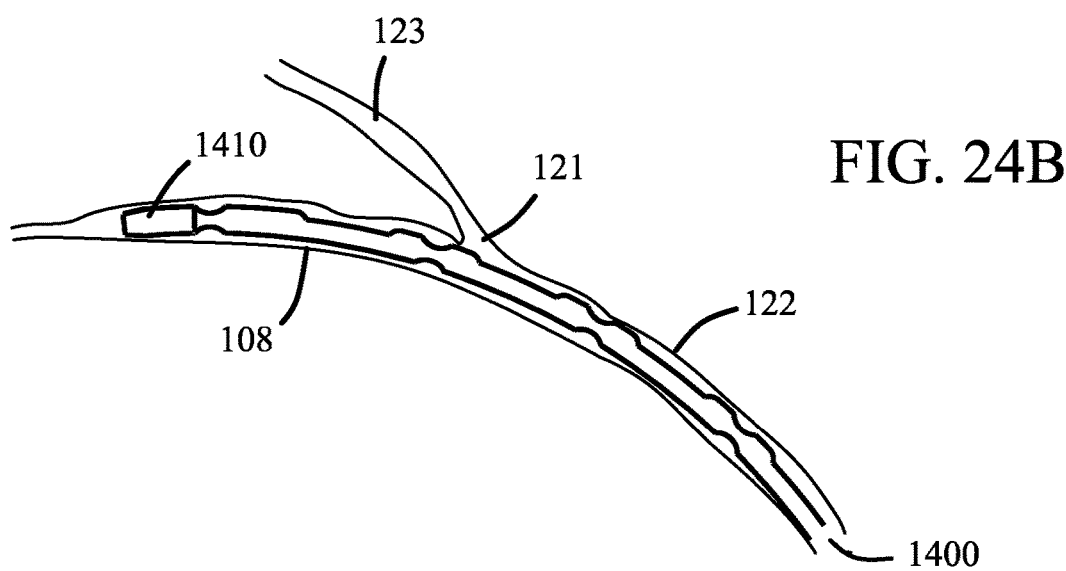
FIG. 24B is an enlarged overhead view of a Schlemm's canal with an embodiment implanted into the canal separating the trabecular meshwork from the posterior wall of the Schlemm's canal and relieving the herniation of trabecular meshwork.
Figure 24C:
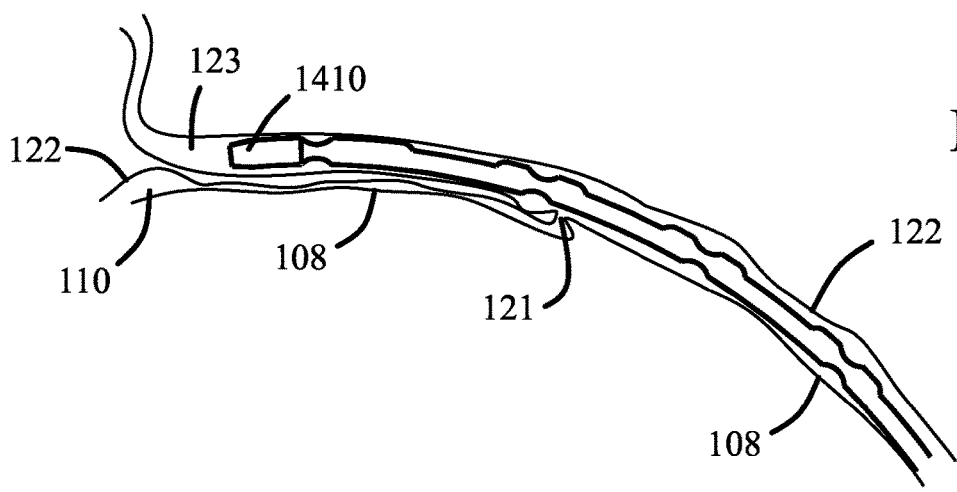
FIG. 24C is an enlarged overhead view of a Schlemm's canal with an embodiment implanted into the canal such that the end or tip of the implant has passed through the collector channel opening both resolving the herniation of trabecular meshwork and dilating a collector channel entrance and a proximal collector channel.

FIG. 24A is an overhead view of a portion of a Schlemm's canal 110 and collapsed collector channel 123 at a point of herniation 108' of the trabecular meshwork 108 into the collector channel entrance 121. FIG. 24B is an overhead view of a portion of a Schlemm's canal 110 and an arcuate scaffold according to the embodiment 1400, or embodiment 1490 (not shown), positioned within the Schlemm's canal 110 effectively separating the trabecular meshwork 108 from the posterior wall 122 of the Schlemm's canal 110 resolving and further preventing herniation 108' of trabecular meshwork 108 into the collector channel entrance 121. FIG. 24C is an overhead view of a portion of a Schlemm's canal 110 and an embodiment an arcuate scaffold according to the embodiments 1400 and 1490 inserted through the collector channel entrance 121 and dilating the proximal collector channel 123.

Figure 25D:
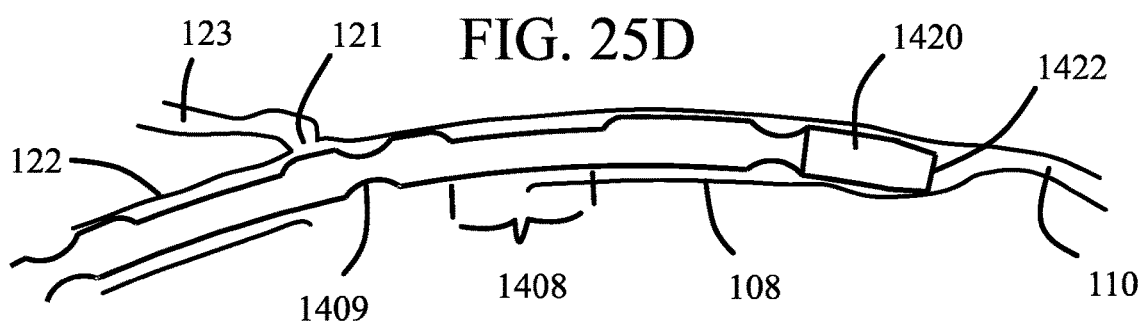
FIG. 25D is an enlarged overhead view of the end or tip of an embodiment demonstrating exposure of an internal window through a small trabeculotomy created either at the time of initial surgery or at a later time with laser goniopuncture.

FIG. 25A is an overhead view of a portion of a Schlemm's canal 110 and an arcuate scaffold according to embodiments 1400 and 1490 fully positioned within the Schlemm's canal 110 and openings 1408, 1409 and 1416 (not visible) in the scaffold covered by trabecular meshwork 108. As further depicted in the figure, the end opening 1422 is in communication with the lumen of Schlemm's canal 110 allowing for direct flow of aqueous between the lumen of Schlemm's canal 110 and the end opening 1422. FIG. 25B is an overhead view of a portion of a Schlemm's canal 110 and an arcuate scaffold according to embodiments 1400 and 1490 positioned within the Schlemm's canal 110 with the end 1420 of the scaffold positioned through a trabeculotomy, anterior to the trabecular meshwork 108, but still within the angle depression formed by Schlemm's canal 110. FIG. 25C is an overhead view of a portion of a Schlemm's canal 110 and an arcuate scaffold according to embodiments 1400 and 1490 positioned within the Schlemm's canal 110 with the opening 1409, and end 1420 of the scaffold exposed by the trabeculotomy allowing direct aqueous flow into both opening 1409 and the opening 1422 in the end 1420 of the scaffold. FIG. 25D is an overhead view of a portion of a Schlemm's canal 110 and an arcuate scaffold according to embodiments 1400 and 1490 inserted with a window or opening 1409 of the scaffold exposed and another window or opening 1408 partially exposed by a trabeculotomy created either at the time of initial surgery or at a later time with laser goniopuncture, as discussed further below.

It may be considered desirable (for example, in the case where the trabecular meshwork mechanosensing/mechanotransducing mechanisms are either inadequate or unable to be sufficiently enhanced by the placement of the aqueous humor outflow device according to embodiments of the invention) to create a direct opening in the trabecular meshwork 108 (also known as a trabeculotomy) in order to allow aqueous humor direct access into the space within the primary implant and from there to a collector channel entrance 121 and out through a collector channel 123.

Although it is possible for a trabeculotomy to be surgically created through a trabecular meshwork 108 in an eye without an aqueous humor outflow device implanted, to do so currently requires incisional surgery performed under sterile conditions within an operating room. A trabeculotomy may be used in embodiments of the invention, and can be performed later, after installation of the aqueous humor outflow device. A type of laser, Nd:YAG (neodymium-doped yttrium aluminum garnet) more commonly referred to as a "YAG" laser can be used, according to one embodiment, to perform trabeculotomy through a goniolens or gonioprism. This procedure is often referred to as YAG laser goniopuncture.

In common practice this procedure is performed only after canaloplasty (a type of Schlemm's canal-dilating surgery in which a polypropylene suture is used to dilate the Schlemm's canal 110). Because polypropylene suture is often dyed blue it can be easily seen behind the trabecular meshwork 108 allowing for targeting of the laser beam. However, when performed in this setting it is possible for the laser to break the suture or for the suture to cheese wire, or slice, through the trabeculotomy, resulting in loss of dilation of the Schlemm's canal 110.

Without the presence of a polypropylene suture it is often difficult to visualize the trabecular meshwork 108 unless it is pigmented or the Sclemm's canal 110 is filled with blood. A laser treatment placed anterior to the trabecular meshwork 108 could damage the corneal endothelium, whereas if placed too posteriorly it could damage vascular tissues resulting in bleeding within the eye. Both of these complications could result in transient or permanent loss of vision. Although trabecular microbypass implants can be visualized through the trabecular meshwork 108, placement of a laser treatment over such microbypass implants could result in displacement of the implant potentially reducing the effectiveness of the implant and damaging intraocular tissue.

According to embodiments of the aqueous humor outflow device described herein, the device is fully implanted within the conventional aqueous humor outflow pathway. The device can be visualized with a gonioprism or goniolens through the trabecular meshwork 108. This allows for the safe placement of a trabeculotomy in the office or outpatient surgery setting with use of a laser at any time after the initial surgical placement of the implant according to embodiments of the invention. The first and second arcuate rails combined with the structural components can be visualized through the trabecular meshwork 108 providing a target at which the laser can be aimed. This reduces the risk of unintentional damage to adjacent structures of the eye. It should be additionally noted that as the aqueous humor outflow device sits fully within the Sclemm's canal 110 the risk of extrusion from the Schlemm's canal 110 or displacement into the anterior chamber is reduced compared to what would be expected with trabecular microbypass devices.

Figure 26A:
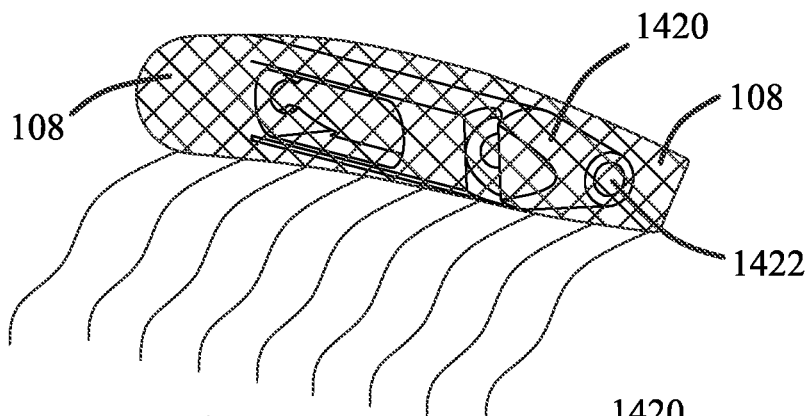
FIG. 26A is an enlarged perspective view of the end or tip of an embodiment fully implanted within the Schlemm's canal.
Figure 26B:
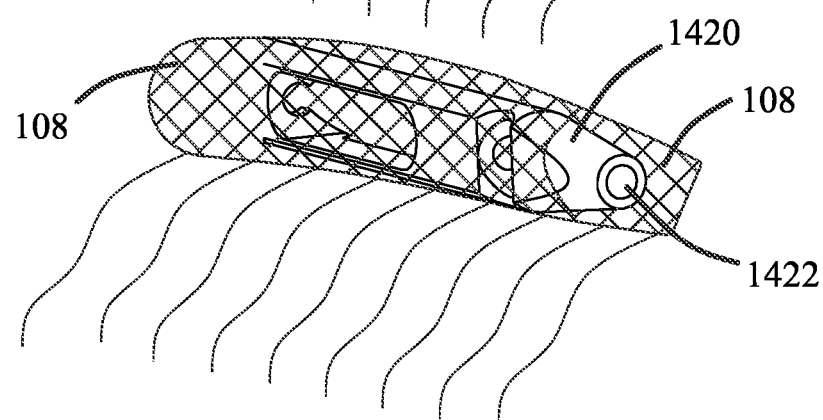
FIG. 26B is an enlarged perspective view of the end or tip of an embodiment positioned within the Schlemm's canal demonstrating the tip positioned through the trabeculotomy, anterior to trabecular meshwork, but still within the angle depression formed by Schlemm's canal.
Figure 26C:
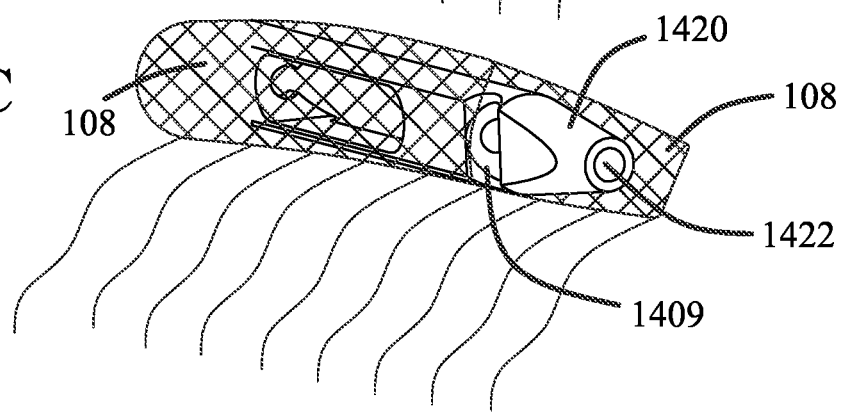
FIG. 26C is an enlarged perspective view of the end or tip of an embodiment demonstrating exposure of the terminal inlet and tip sideport through a small trabeculotomy allowing direct aqueous flow into the implant openings.
Figure 26D:
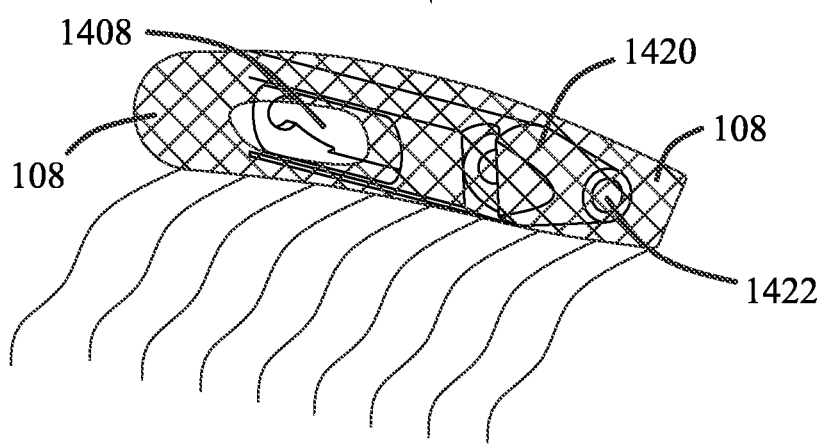
FIG. 26D is an enlarged perspective view of the end or tip of an embodiment demonstrating exposure of an internal window through a small trabeculotomy created either at the time of initial surgery or at a later time with laser goniopuncture.

FIG. 26A is an enlarged perspective view of a portion of a Schlemm's canal 110 and an arcuate scaffold according to embodiment 1400, or embodiment 1490 (not shown), fully positioned within the Schlemm's canal 110 and all openings 1408, 1409, 1416 (not visible) and 1422 in the scaffold covered by trabecular meshwork 108. FIG. 26B is an enlarged perspective view of a portion of a Schlemm's canal 110 and an arcuate scaffold according to the embodiment 1400, or embodiment 1490 (not shown), positioned within the Schlemm's canal 110 with the end 1420 of the scaffold positioned through the trabeculotomy, anterior to trabecular meshwork 108, but still within the angle depression formed by Schlemm's canal 110. FIG. 26C is an enlarged perspective view of a portion of a Schlemm's canal 110 and an arcuate scaffold according to the embodiment 1400, or embodiment 1490 (not shown), positioned within the Schlemm's canal 110 with the end 1420 of the scaffold exposed by the trabeculotomy allowing direct aqueous flow into the respective end and side openings 1422 and 1409 in the scaffold. FIG. 26D is an enlarged perspective view of a portion of a Schlemm's canal 110 and an arcuate scaffold according to the embodiment 1400, or embodiment 1490 (not shown), inserted with a window or opening 1408 of the scaffold exposed by a trabeculotomy created either at the time of initial surgery or at a later time with laser goniopuncture.

Figure 27:
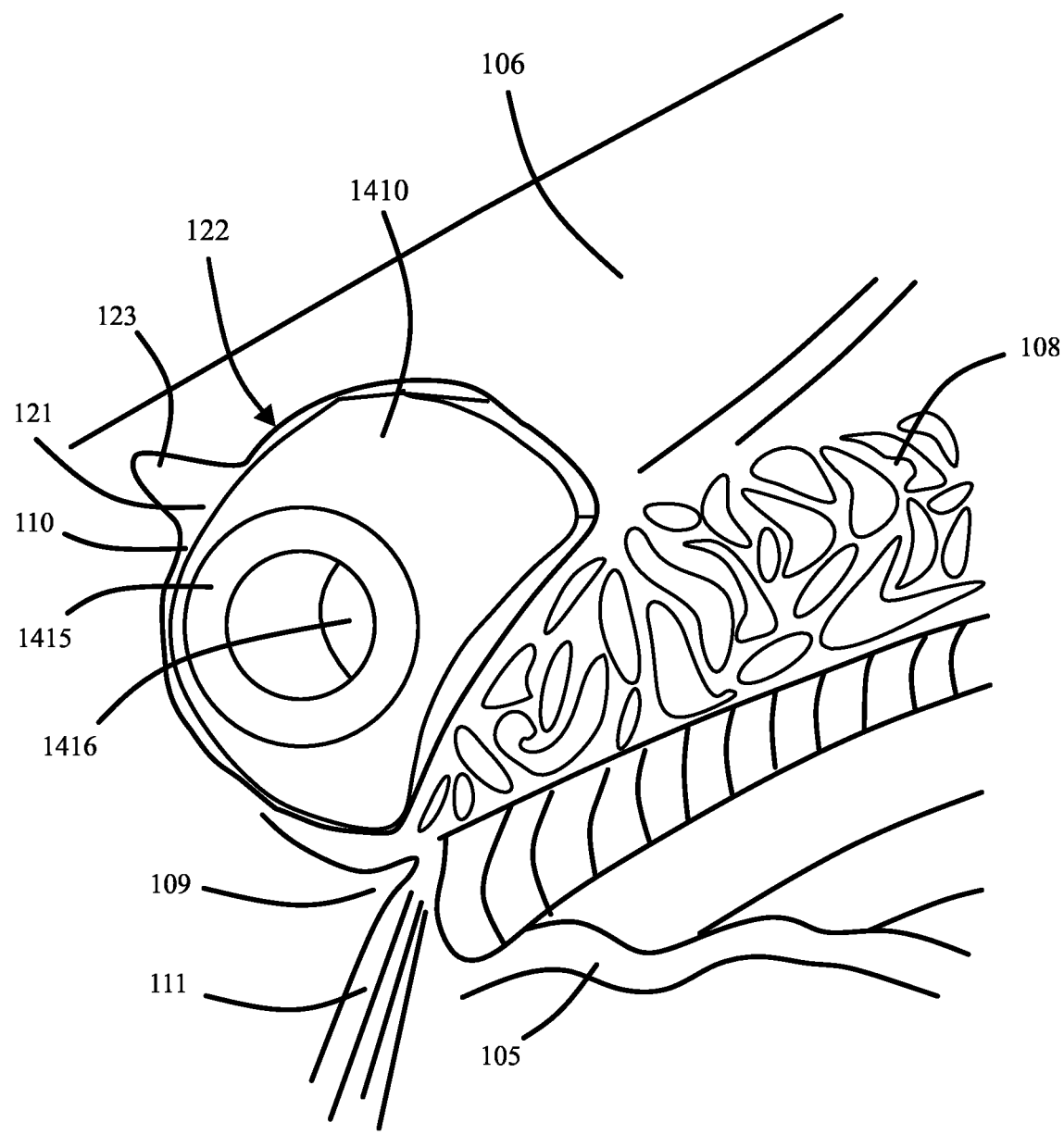
FIG. 27 is an enlarged cross-sectional view of the anterior chamber angle showing the relationship of the implant to the angle structures.

With reference to the discussion of FIGS. 2-4, FIG. 27 is an enlarged cross-sectional view of the anterior chamber angle showing the relationship of an arcuate scaffold to the angle structures, according to embodiments of the invention. In particular, FIG. 27 is an enlarged cross-sectional view of an anterior chamber angle showing an end 1410 of an arcuate scaffold according to embodiments 1400 and 1490 positioned in the Schlemm's canal 110. This figure demonstrates:

dilation of Schlemm's canal 110;
distension of the trabecular meshwork 108;
separation of the trabecular meshwork 108 from the posterior wall 122 of Schlemm's canal 110; and
resolution of herniation 108' of trabecular meshwork 108 from collector channel entrances 121.

Figure 1:
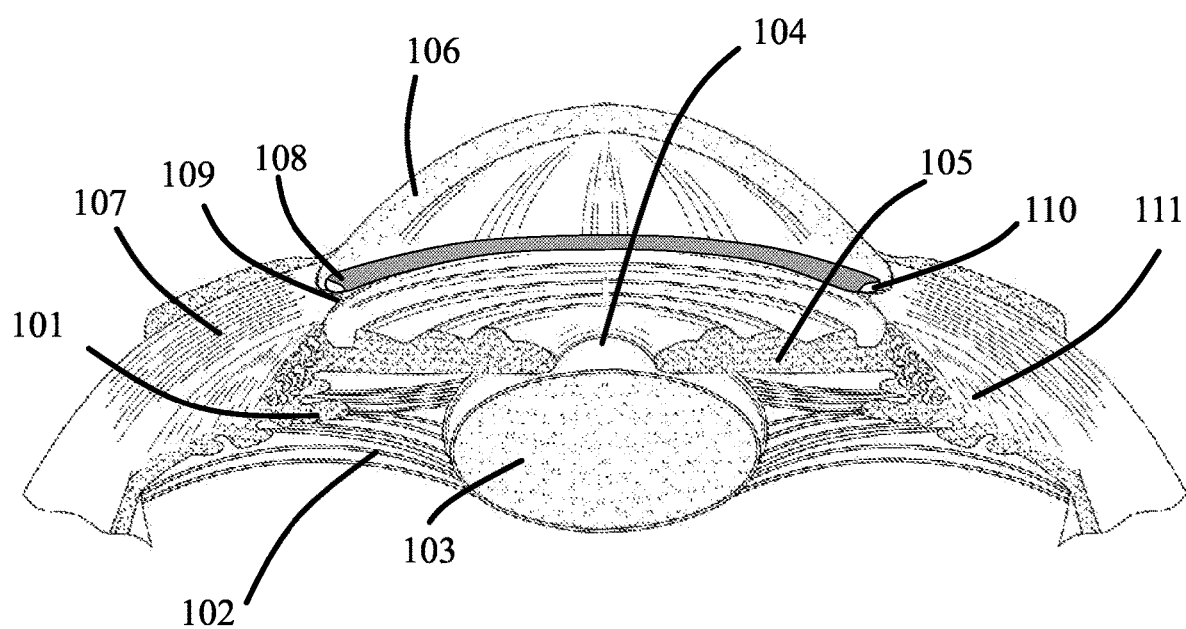
FIG. 1 depicts a cross-sectional view of an anterior segment of an eye.
Figure 2:
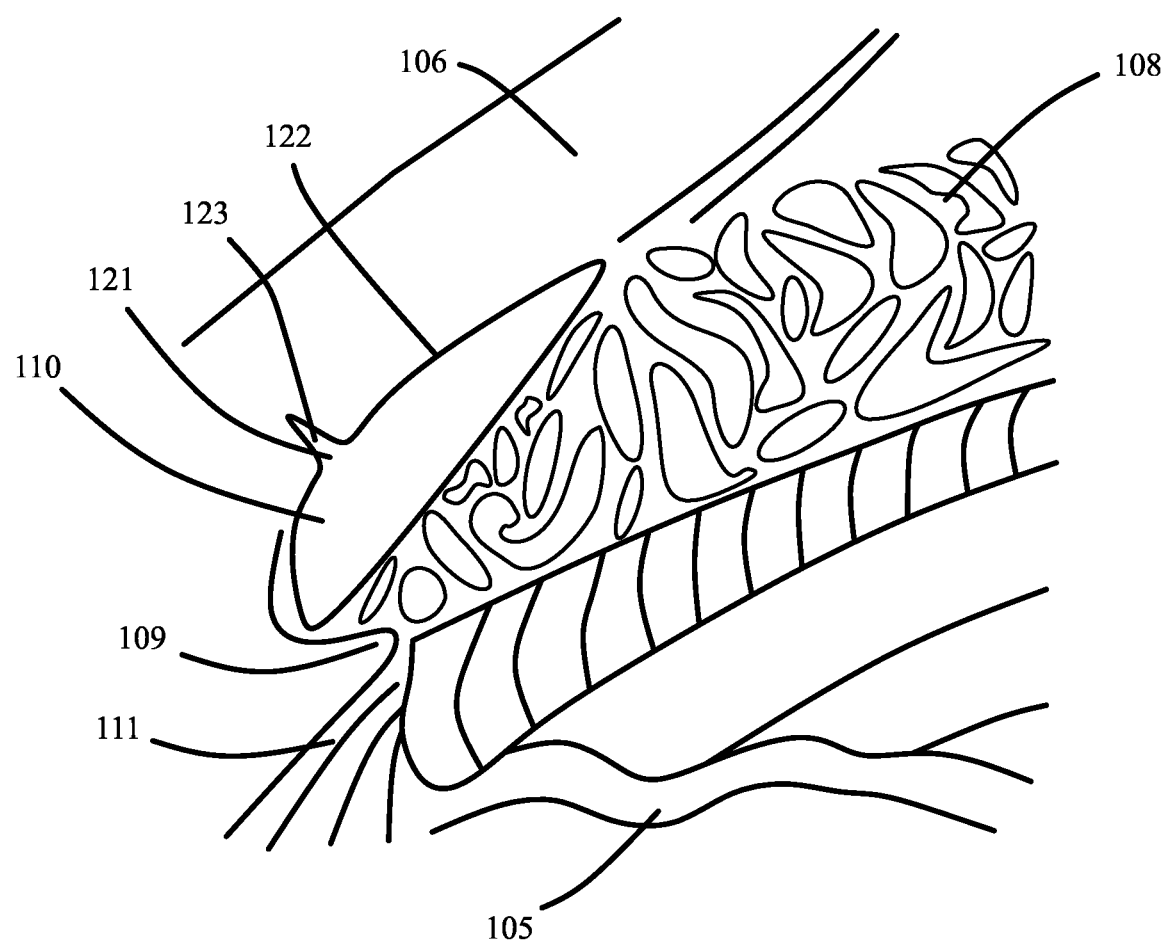
FIG. 2 depicts an enlarged cross-sectional view of the anterior chamber of the eye illustrating the normal physiologic state of the angle in an eye without glaucoma.
Figure 3:
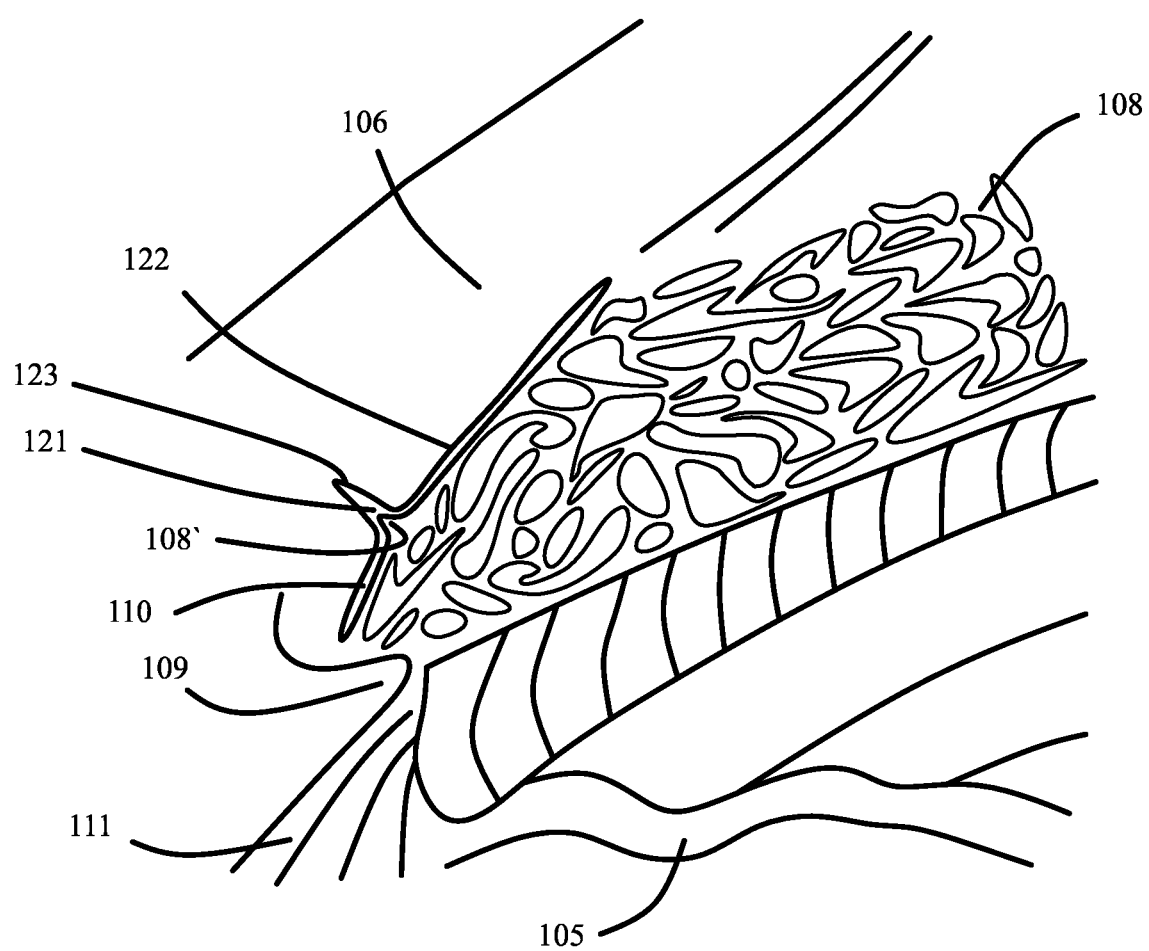
FIG. 3 depicts an enlarged cross-sectional view of the anterior chamber of an eye illustrating an angle in an eye with glaucoma.
Figure 4:
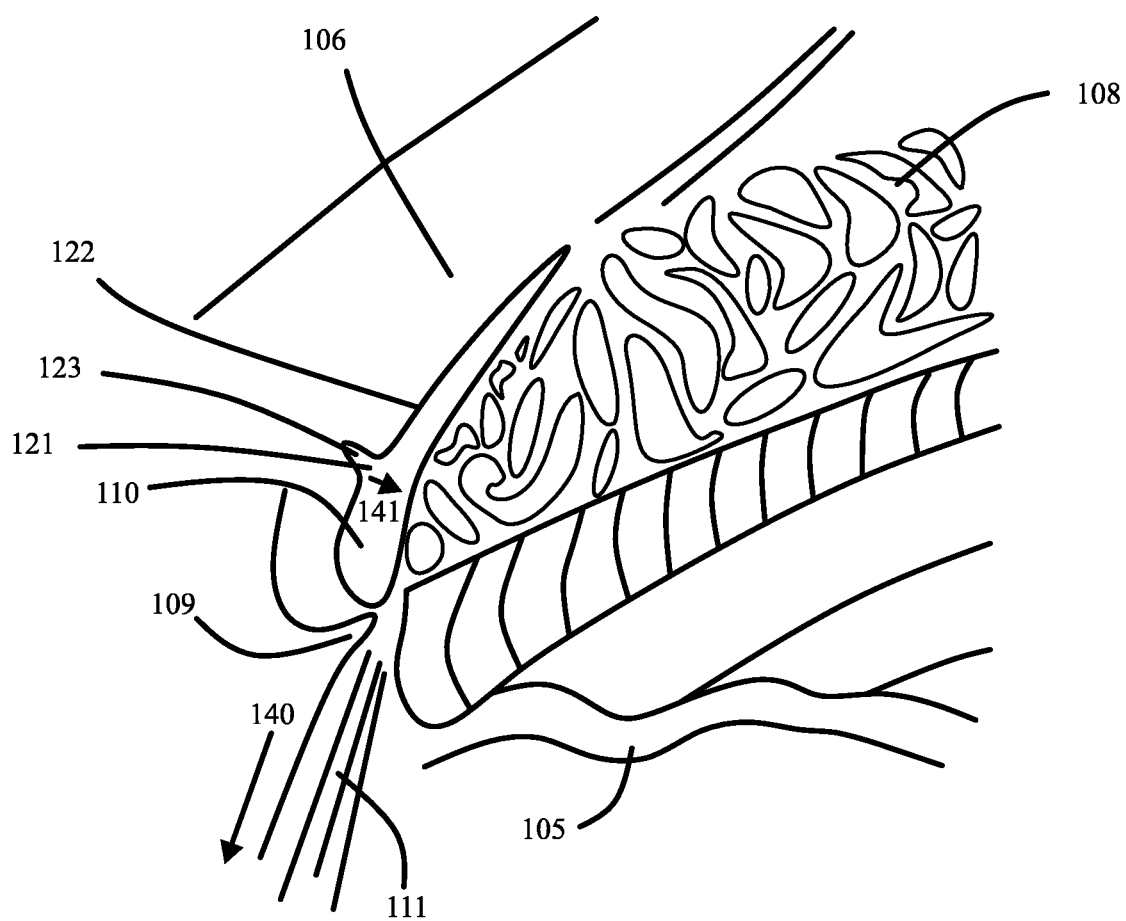
FIG. 4 depicts an enlarged cross-sectional view of the anterior chamber of the eye illustrating the effect of pilocarpine on the angle anatomy.

Recall from the discussion of FIGS. 2-4 that the portion of the anterior chamber where the iris 105, the sclera 107, and cornea 106 meet is termed the "angle". In what is termed the conventional outflow pathway, aqueous humor leaves the anterior chamber through the angle structure termed the trabecular meshwork 108 which is bordered by a scleral spur 109 inferiorly, cornea 106 superiorly, and posteriorly by a Schlemm's canal 110. Aqueous humor passes through the trabecular meshwork 108 into the Schlemm's canal 110 and from there through a collector channel entrance 121 located on a posterior wall 122 of the Schlemm's canal 110 into a collector channel 123 which connects to an aqueous humor outflow vein from which aqueous humor may enter the larger venous blood vessels of the body.

Figure 28:
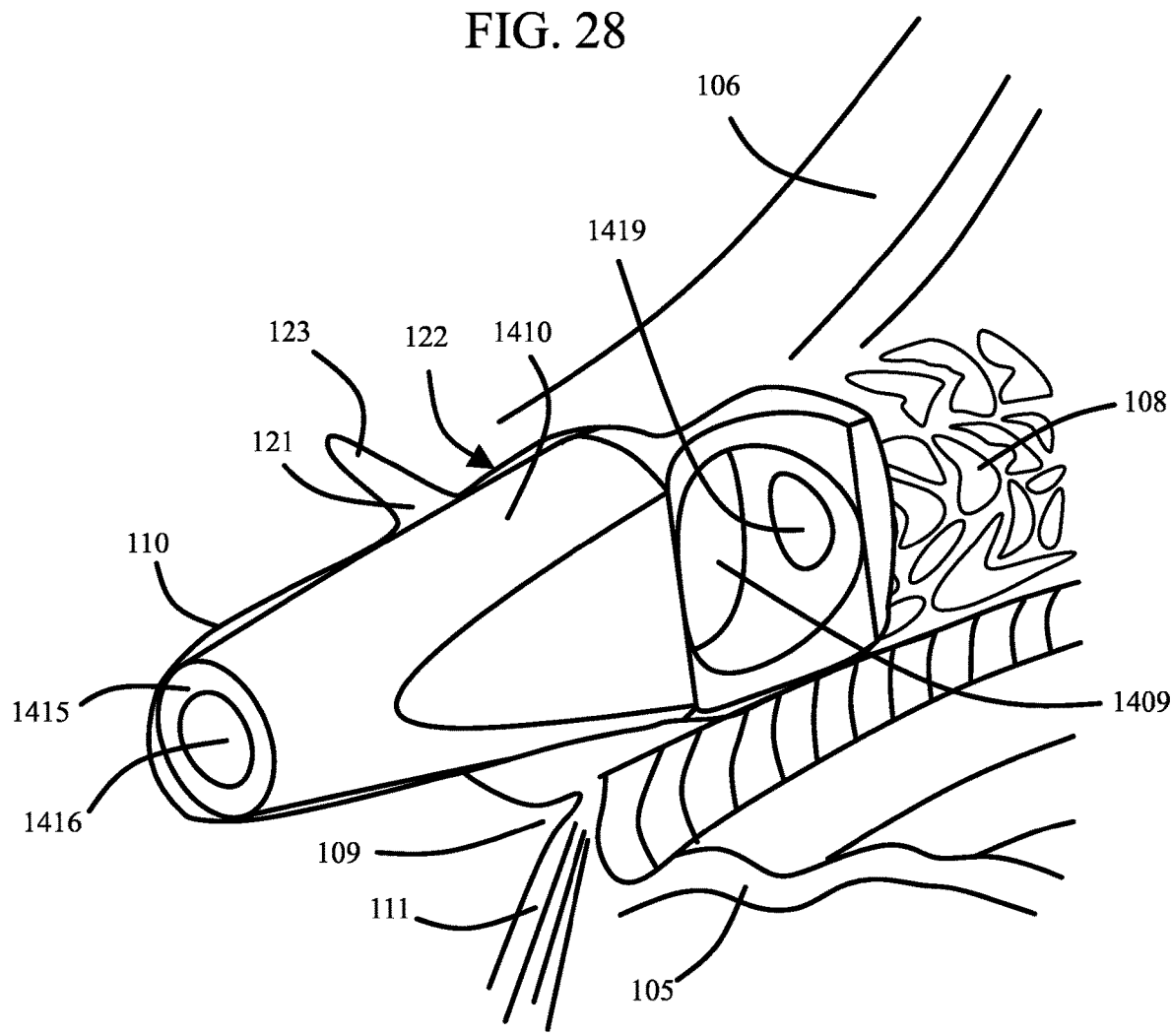
FIG. 28 is an enlarged cross-sectional view of the anterior chamber angle showing the tip of an embodiment positioned in the Schlemm's canal with direct access of aqueous to the sideport opening.

FIG. 28 is an enlarged cross-sectional view of an anterior chamber angle showing an end 1410 of an arcuate scaffold according to embodiment 1400, or embodiment 1490 (not shown), positioned in the Schlemm's canal 110 with direct access of aqueous humor to the sideport opening 1409.

FIGS. 29A and 29B depict enlarged front and back perspective views of an arcuate scaffold according to the embodiment 1400 showing the flow 2900 of aqueous humor through the trabecular meshwork 108 into the lumen of the arcuate scaffold wherein the flow can move in a longitudinal direction 2901 within (intra-chamber flow) and between (inter-chamber flow) Schlemm's canal 110 chambers 131. As mentioned above, the combination of the aqueous humor outflow device according to embodiment 1400, the trabecular meshwork 108, and the posterior wall 122 of the Schlemm's canal 110 results in chambers 1408' analogous to those chambers 131 present in a normal Schlemm's canal 110. For the purposes of this discussion, the "lumen of the arcuate scaffold" is understood to mean the volume defined by the combination of internal surfaces of the arcuate scaffold, the trabecular meshwork 108, the walls of Schlemm's canal 110, and internal surface of collector channel 123 in direct contact with the arcuate scaffold.

FIGS. 30A-30D depict cross sectional views of a Schlemm's canal 110 with an arcuate scaffold according to the embodiment 1400 implanted into the Schlemm's canal 110 demonstrating flow of aqueous humor within the scaffold and out the collector channel 123.

Figure 5A:
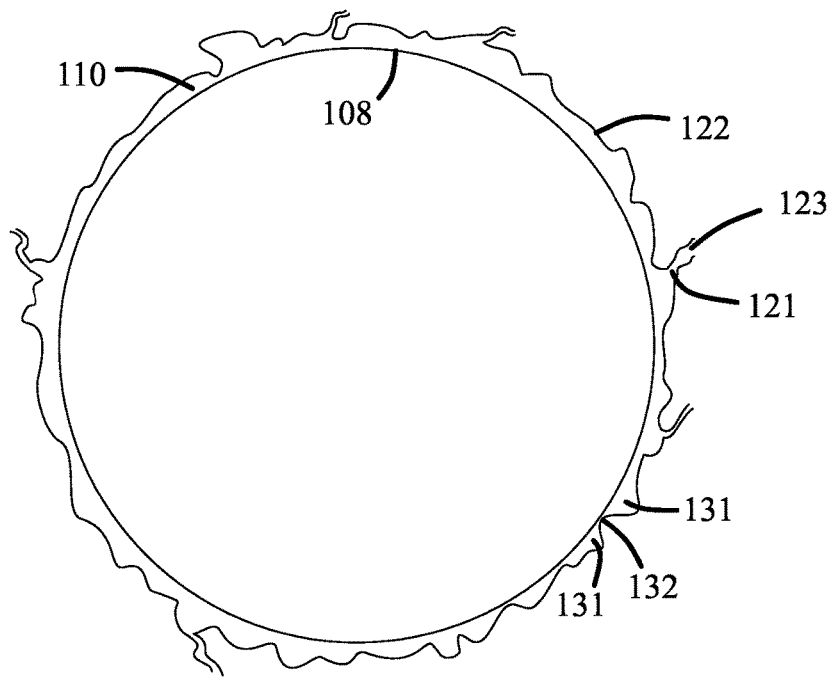
FIG. 5A depicts an overhead view of a Schlemm's canal.
Figure 5B:
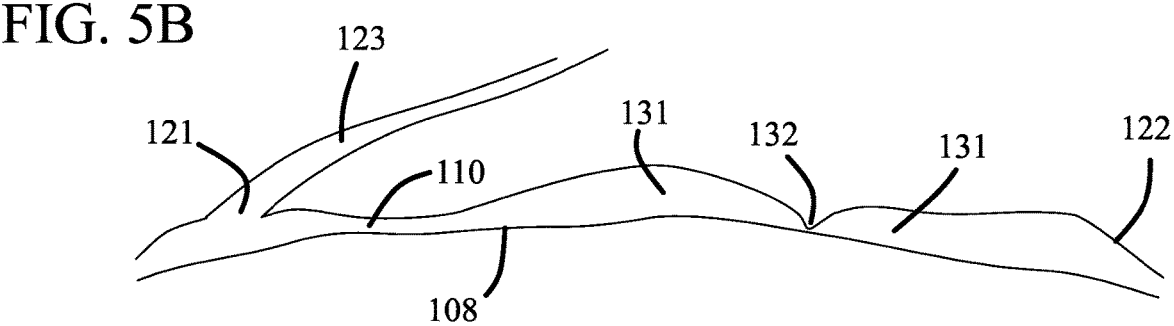
FIG. 5B depicts an enlarged portion of the overhead view of a Schlemm's canal.
Figure 5C:
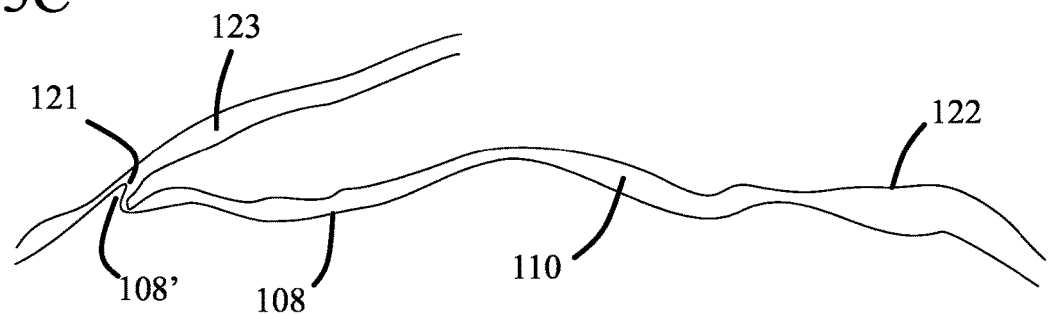
FIG. 5C depicts another view of the enlarged overhead view of a Schlemm's canal.

Recall the discussion with reference to the overhead view of a Schlemm's canal 110 in FIGS. 5A and 5B demonstrating the irregular contour of the posterior wall 122 of the Schlemm's canal 110, the interaction of the trabecular meshwork 108 and the posterior wall 122 of the Schlemm's canal 110 to create a membrane valve 132 functionally separating the Schlemm's canal 110 into irregularly shaped and sized chambers 131, and the chain of such chambers 131, in which the flow of aqueous through the Schlemm's canal 110 is non-uniform. When combined with the ocular pulse pressure depicted by +P at 3001 in FIGS. 30B-30D, aqueous humor moves through the trabecular meshwork 108 into the analogous chambers 1408'A and 1408'B and from chamber 1408'A to chamber 1408'B toward a collector channel entrance 121 and collector channel 123 through which aqueous humor drains into an aqueous vein (not shown) and into the general circulatory system of the body (not shown). The portions of the posterior wall 122 of Schlemm's canal 110 in apposition to the posterior surface 1407 of the structural components 1405 that separate these analogous chambers 1408'A and 1408'B may act in a manner similar to membrane valves 132 providing some element of directional flow 3002 of aqueous humor down a pressure gradient toward the collector channel entrances 121. Essentially, the pulse pressure on the trabecular meshwork 108 causes analogous chamber 1408'A to operate as a piston and push aqueous humor into the adjacent analogous chamber 1408'B. The displacement of the trabecular meshwork 108 also causes analogous chamber 1408'B to operate as a piston to push aqueous humor through collector channel entrance 121 and out the collector channel 123. Note that both the displacement of the trabecular meshwork 108 at analogous chamber 1408'B during the pulse pressure and the flow of aqueous humor from analogous chamber 1408'A function to force aqueous humor down a pressure gradient out of Schlemm's canal 110 into the collector channel 123.

With reference to FIGS. 14A-14O, 14M-14O and 30A-30D, the trabecular meshwork 108 abuts openings 1408 framed by the first and second arcuate rails 1401 and 1402 and the structural components 1405. According to one embodiment, the trabecular meshwork 108, when subjected to an intraocular pressure 3001, in particular, an intraocular pulse pressure, operates as a membrane (i.e., a diaphragm) that stretches and distends into the openings 1408 as depicted at 3003, which creates positive pressure in the chamber, depicted as "+P", in FIGS. 30B-30D. The openings 1408 are framed by the first and second arcuate rails 1401, 1402 and the structural components 1405. When implanted into the Schlemm's canal 110, the openings 1408 bounded by the first and second arcuate rails 1401, 1402, adjacent structural components 1405, trabecular meshwork 108, and posterior wall 122 of Schlemm's canal 110 defines a potential three dimensional space or chamber 1408'A and 1408'B that is analogous to the chambers 131 present in a healthy Schlemm's canal 110. Aqueous humor flows through the openings 1408 and 1409, and then in a direction 3002 generally along the longitudinal axis of the arcuate scaffold within and between chambers of the Schlemm's canal 110 to the one or more collector channels 123.

Figure 30A:
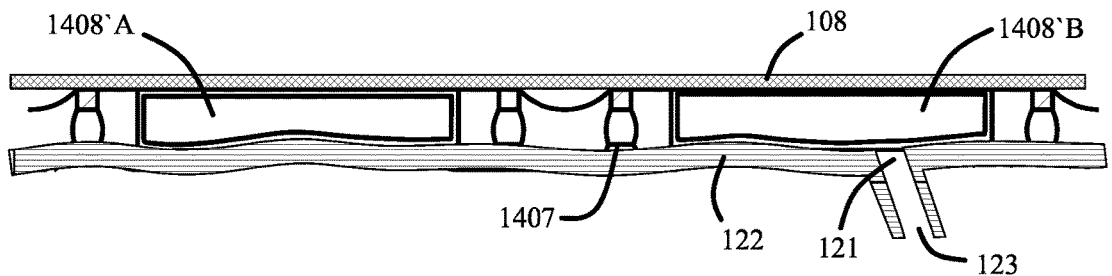
FIG. 30A is an enlarged overhead view of an embodiment showing its relationship to a trabecular meshwork and a posterior wall of a Schlemm's canal during a low pressure phase of an ocular pulse.
Figure 30B:
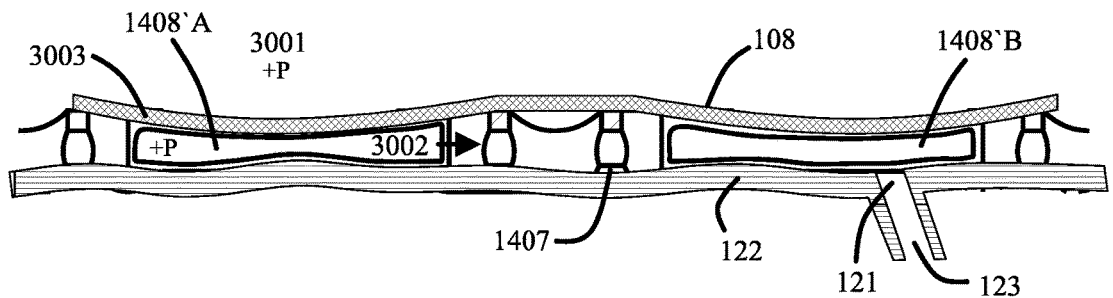
FIG. 30B is an enlarged overhead plan view of an embodiment showing its relationship to a trabecular meshwork and a posterior wall of a Schlemm's canal as well as the flow of aqueous humor during a rise of a pressure phase of the ocular pulse.
Figure 30C:
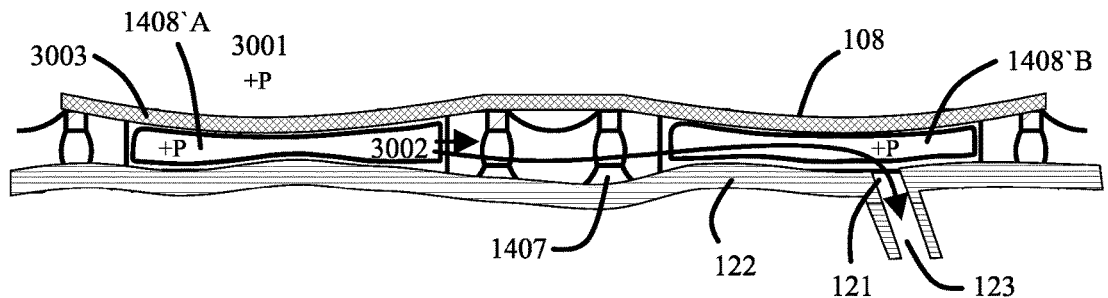
FIG. 30C is an enlarged overhead plan view of an embodiment showing its relationship to a trabecular meshwork and a posterior wall of a Schlemm's canal as well as the flow of aqueous humor toward the end of a high pressure phase of the ocular pulse.

FIG. 30C demonstrates the directional flow 3002 of aqueous humor as it passes from one analogous chamber 1408'A to another analogous chamber 1408'B which occurs when the pressure differential between chambers is sufficient to force the posterior wall 122 of Schlemm's canal 110 away from the posterior edge 1407 of the structural component 1405. Such a pressure differential would be expected, for example, between one analogous chamber 1408'A without a collector channel entrance 121 and another analogous chamber 1408'B with a collector channel entrance 121. This pressure differential would effectively open the membrane valve 132 formed by the posterior wall 122 of Schlemm's canal 110 and the posterior edge 1407 of the structural component 1405 allowing flow of aqueous fluid from one analogous chamber 1408'A to another analogous chamber 1408'B. As aqueous humor passes circumferentially along the posterior wall 122 of Schlemm's canal 110, a greater shear stress is experienced by the endothelial cells which line the posterior wall 122 of Schlemm's canal 110 in this area due to the relatively reduced effective diameter of the canal lumen posterior to the structural elements 1405. It should be noted that the endothelial cells of Schlemm's canal 110 have been demonstrated to exhibit mechanosensing/mechanotransducing abilities, similar to that seen within the trabecular meshwork 108. Whereas the cells of the trabecular meshwork 108 appear to be most sensitive to stretch, the endothelial cells of Schlemm's canal 110 have been shown to respond to changes in shear stress by increasing nitric oxide (NO) production resulting in increased facility of aqueous humor outflow (reduced resistance of outflow) leading to a reduction of IOP. Thus, another function of the structural elements 1405 is to increase the shear stress experienced by the endothelial cells of Schlemm's canal 110 in order to activate mechanosensing/mechanotransducing homeostatic mechanisms that would result in further reduction in IOP.

According to the embodiment 1400, a depression in the posterior edge 1407 of the structural element 1405 may combine or merge with a respective opening 1419 as depicted, e.g., in FIGS. 14A, 15A, to further increase the flow of aqueous humor between the respective analogous chambers 1408', which would function to allow some flow of aqueous humor between analogous chambers 1408' even when the pressure differential between chambers was insufficient to fully open the membrane valve 132. Given the small effective diameter of the lumen in the area of this depression in the posterior edge 1407 of the structural element 1405, the Schlemm's canal 110 endothelial cells would be expected to experience an increase in shear stress as aqueous humor passed through this space, potentially resulting in triggering of the Schlemm's canal endothelial cell mechanosensing/mechanotransducing mechanisms discussed above resulting in decreased IOP.

Figure 30D:
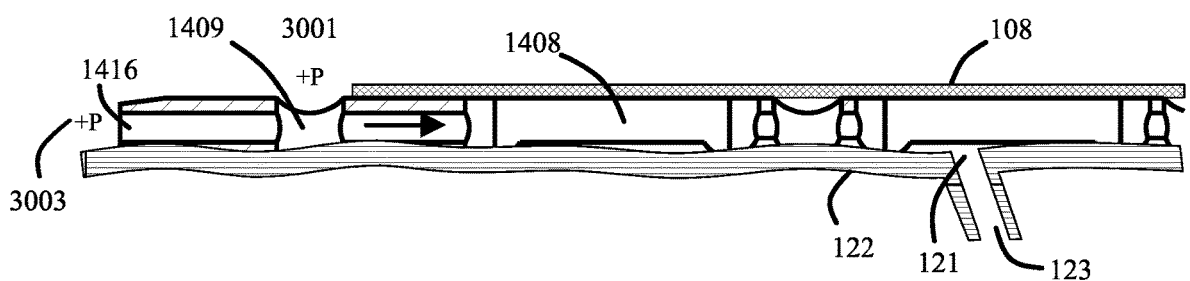
FIG. 30D is an enlarged overhead plan partial view of an embodiment showing the direction of aqueous flow through a hole in the end and side opening into the lumen of the embodiment.

FIG. 30D is an enlarged overhead plan view of an arcuate scaffold according to an embodiment 1400 showing the direction of aqueous flow through a hole 1416 in the end 1410 and side opening 1409 into the lumen of the scaffold.

Figure 31:
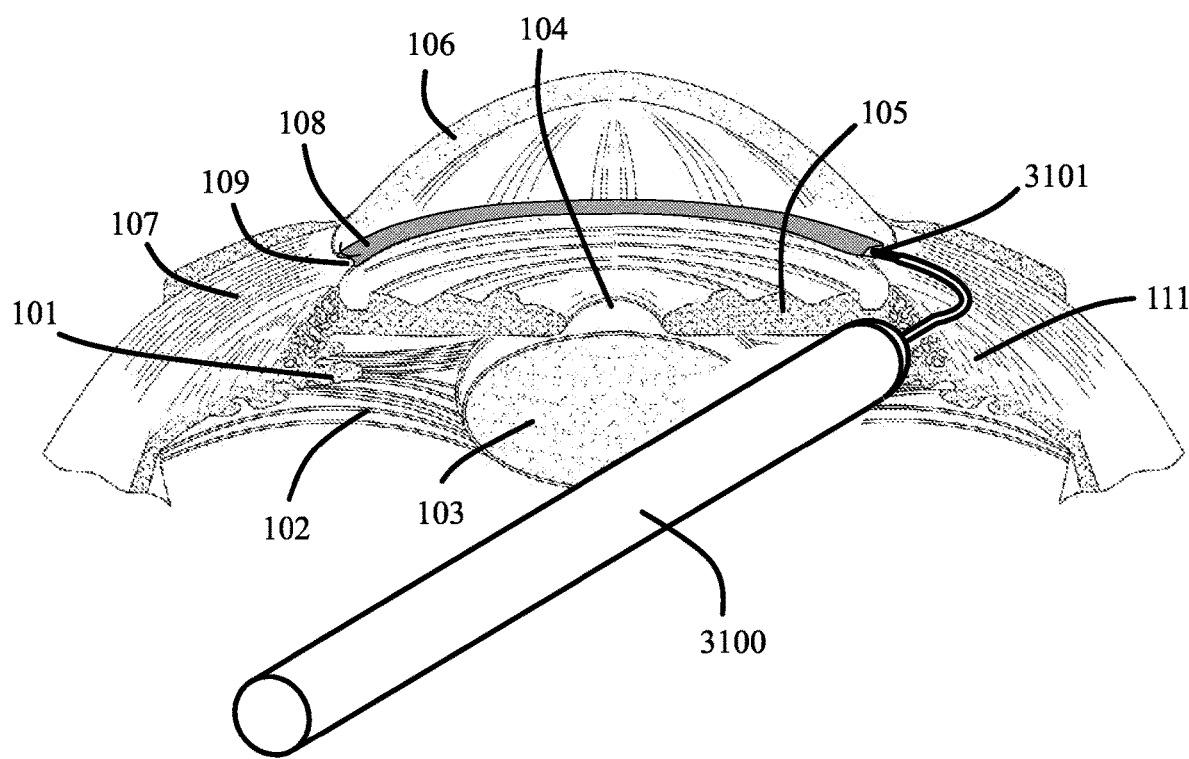
FIG. 31 is a cross-sectional view of an anterior segment of an eye with a perspective view of a device used to insert one of an embodiment showing its position during initial insertion of the embodiment through a trabecular meshwork into a Schlemm's canal.
Figure 32:
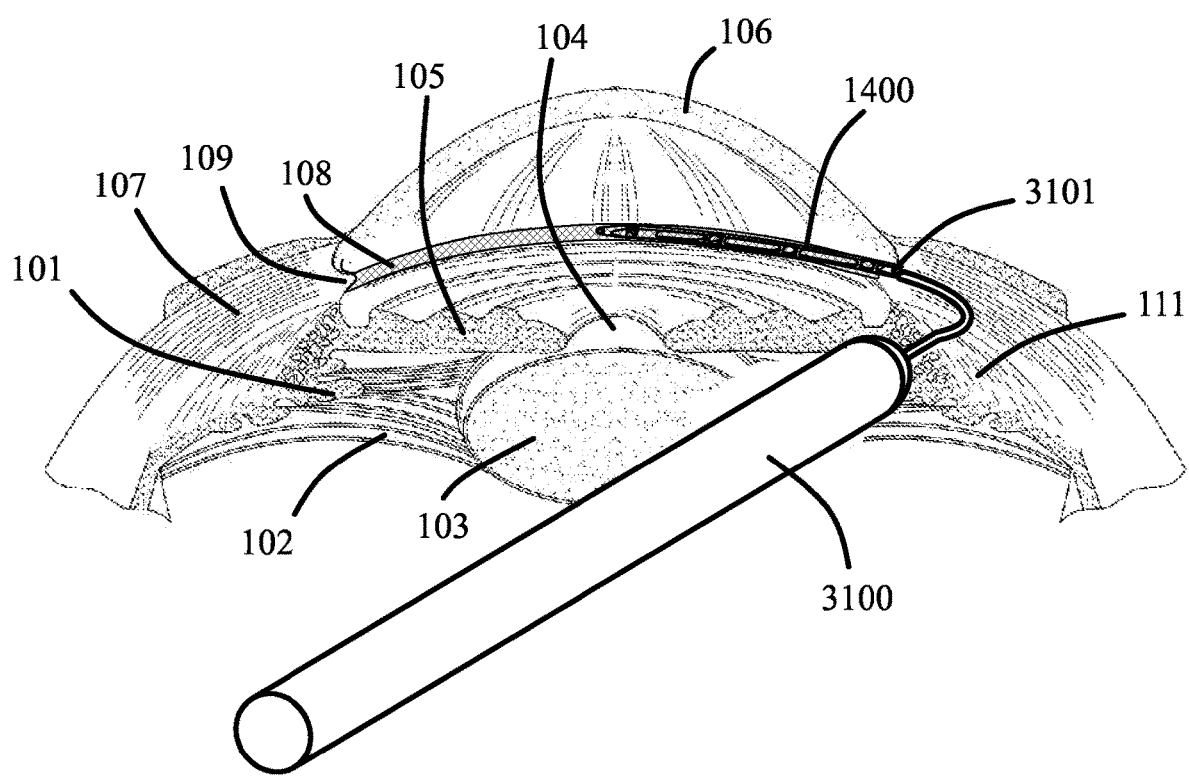
FIG. 32 is a cross-sectional view of an anterior segment of an eye with a perspective view of the insertion device of FIG. 31 showing the insertion of the embodiment within the lumen of a Schlemm's canal.
Figure 33:
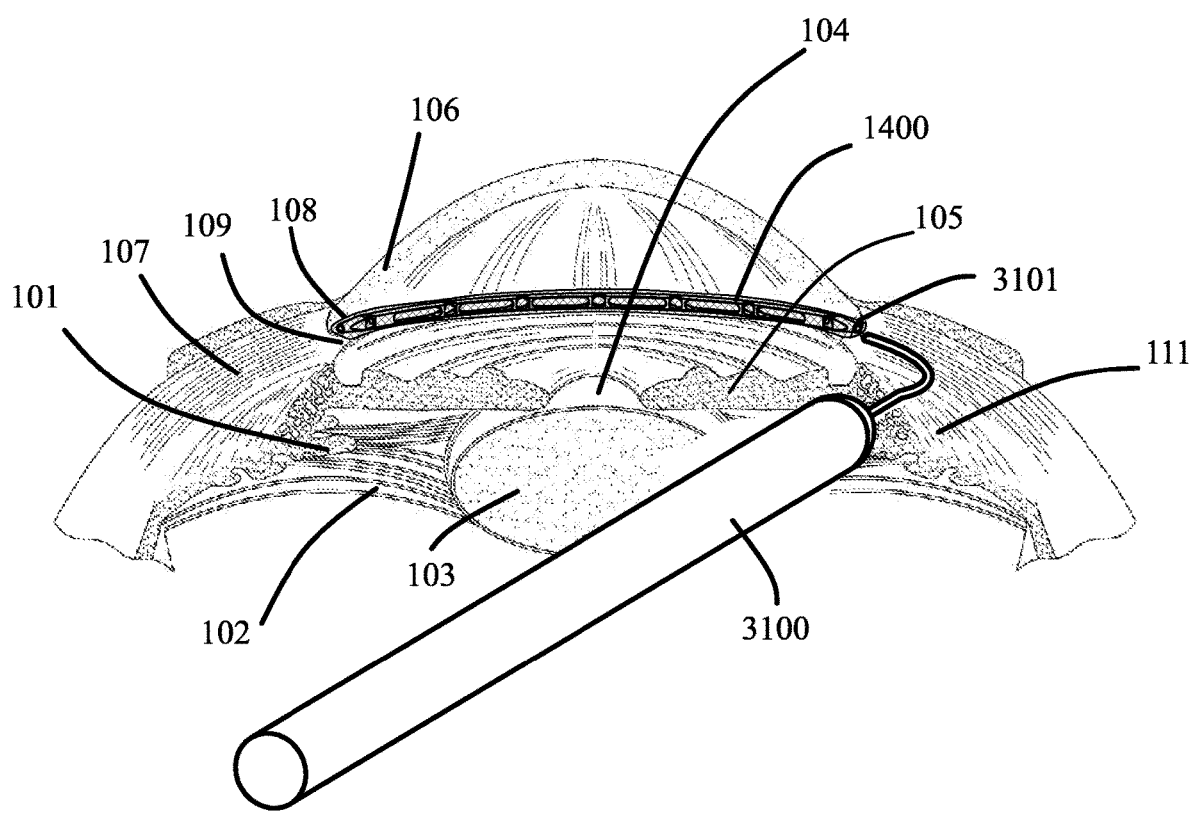
FIG. 33 is a cross-sectional view of an anterior segment of an eye with a perspective view of the insertion device of FIG. 31 showing the embodiment fully inserted within the lumen of a Schlemm's canal.
Figure 34:
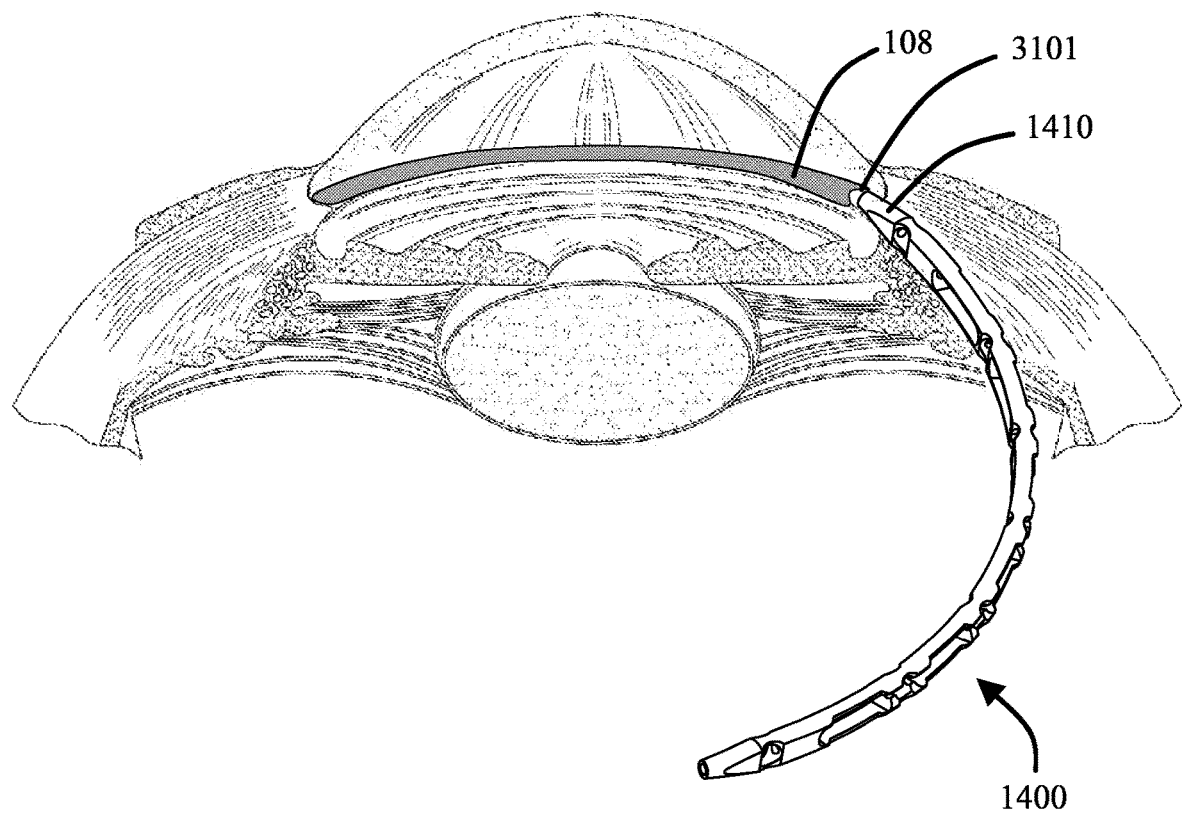
FIG. 34 is a cross-sectional view of an anterior segment of an eye with a perspective view of the embodiment showing its position prior to insertion through a trabecular meshwork into a Schlemm's canal.

FIG. 31 is a view of a representative insertion system 3100 with a cannula positioned at the Schlemm's canal 110 insertion location 3101. FIG. 32 is a view of a representative insertion system 3100 with a cannula positioned at the Schlemm's canal 110 insertion location 3101 with approximately half of the arcuate scaffold (e.g., according to the embodiments 1400 and 1490) in Schlemm's canal 110. FIG. 33 is a view of a representative insertion system 3100 with a cannula positioned at the Schlemm's canal 110 insertion location 3101 with the arcuate scaffold fully positioned in Schlemm's canal 110. FIG. 34 is a cross-sectional view of an anterior segment of an eye with a perspective view of an arcuate scaffold according to an embodiment showing the scaffold's position prior to insertion at location 3101 through a trabecular meshwork 108 into a Schlemm's canal 110. Note the end 1410 of the arcuate scaffold 1400, or arcuate scaffold 1490 (not shown), is tapered to facilitate inserting the arcuate scaffold into the Schlemm's canal 110. Tapering of the tip also allows for ease of threading the implant along Schlemm's canal 110 with minimal damage to the canal structures.

According to embodiments, inserting the arcuate scaffold may be performed through a small incision in the cornea, or through a small incision in other ocular tissue.

According to embodiments, while the insertion device simplifies insertion of the aqueous humor outflow device, the design of the aqueous humor outflow device tip is such that it could also be inserted manually with either standard microsurgical instrumentation or surgical instrumentation that could be designed specifically for the process of inserting and/or repositioning the device.

Figure 35:
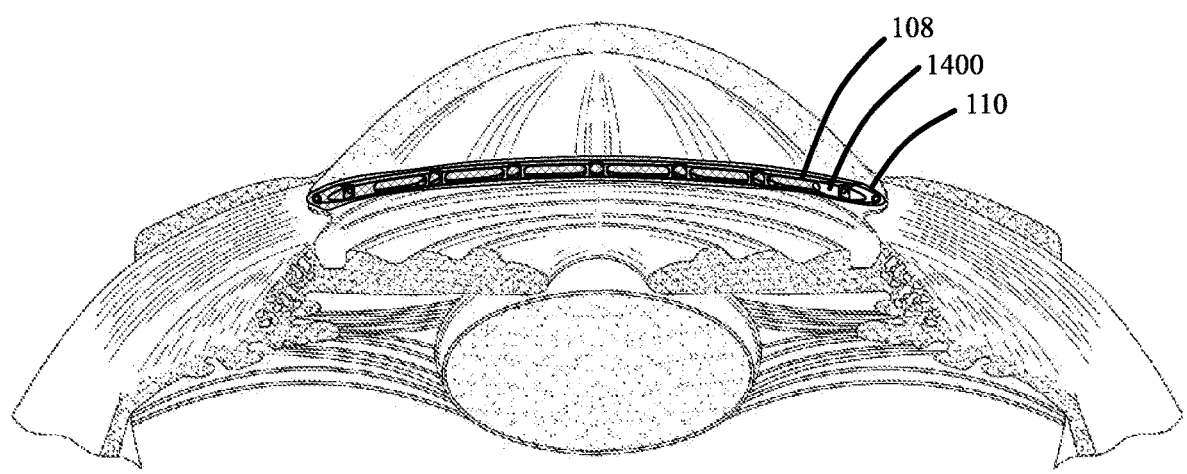
FIG. 35 is a cross-sectional view of an anterior segment of an eye with a perspective view of the embodiment showing its position after near-complete insertion through the trabecular meshwork into the Schlemm's canal.

FIG. 35 is a cross-sectional view of an anterior segment of an eye with a perspective view of an arcuate scaffold according to the embodiments 1400 and 1490 showing its position after being nearly completely inserted through the trabecular meshwork 108 into the Schlemm's canal 110.

Figure 36:
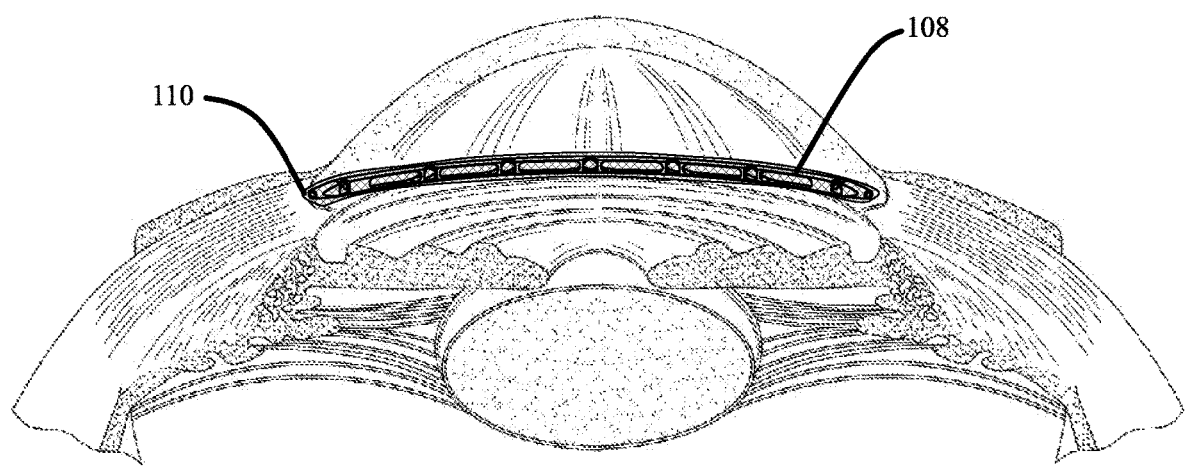
FIG. 36 is a cross-sectional view of an anterior segment of an eye with a perspective view of the embodiment showing its position fully within the Schlemm's canal.

FIG. 36 is a cross-sectional view of an anterior segment of an eye with a perspective view of an arcuate scaffold according to the embodiments 1400 and 1490 showing its position fully within the Schlemm's canal 110.

Although embodiments of the invention have been described in considerable detail, other embodiments are possible. It will be apparent to one with skill in the art that embodiments of the device may be provided using some or all of the aforementioned features and components without departing from the spirit and scope of the invention. It will also be apparent to the skilled artisan that the embodiments described above are specific examples of a single broader device which may have greater scope than any of the singular descriptions taught. There may be many alterations made in the descriptions without departing from the spirit and scope of the invention. Therefore, the spirit and scope of the appended claims should not be limited to the description of the embodiments contained therein.

The invention claimed is:

1. An aqueous humor outflow device, comprising:
an arcuate scaffold to fit within a conventional aqueous humor outflow pathway of a mammalian eye to receive aqueous humor from a trabecular meshwork of the mammalian eye and allow flow of the aqueous humor through the arcuate scaffold to one or more collector channels that originate in a posterior wall of a Schlemm's canal, the arcuate scaffold comprising:
a first arcuate rail;
a second arcuate rail spaced apart from, and substantially parallel to, the first arcuate rail;
the first and second arcuate rails each comprising:
an anterior edge defining an inside circumference of the arcuate scaffold that is adjacent the trabecular meshwork when inserted in the Schlemm's canal; and
a posterior edge defining an outside circumference of the arcuate scaffold that is adjacent to the posterior wall of the Schlemm's canal and one or more collector channels when inserted in the Schlemm's canal; and
a plurality of structural components coupled to the first arcuate rail and the second arcuate rail to maintain the respective anterior and posterior edges of the first and second arcuate rails spaced apart from, and substantially parallel to, each other.

2. The aqueous humor outflow device of claim 1,
wherein the arcuate scaffold extends along a longitudinal axis,
wherein the arcuate scaffold comprises a first end along the longitudinal axis of the arcuate scaffold, and a second, opposite, end along the longitudinal axis of the arcuate scaffold, and
wherein the first arcuate rail and the second arcuate rail spaced apart from, and substantially parallel to, the first arcuate rail, extend continuously from the first end to the second end of the arcuate scaffold.

3. The aqueous humor outflow device of claim 1, wherein the arcuate scaffold further comprises a tapered end that enables introduction of the arcuate scaffold into one of the one or more collector channels that originate in the posterior wall of the Schlemm's canal, or an entrance thereof, and the dilation thereof, as the collector channel entrance and the collector channel widen to accommodate an increasing cross-sectional area of the arcuate scaffold as the arcuate scaffold is inserted into the collector channel.

4. The aqueous humor outflow device of claim 1, wherein the arcuate scaffold comprises a biocompatible material selected from a group of materials consisting of: a metal, an alloy, Nitinol®, titanium, stainless steel, polymer, drug eluting polymer, ceramic, biological material, or combinations thereof.

5. The aqueous humor outflow device of claim 4, wherein the arcuate scaffold further comprising a functional coating selected from a group of functional coatings consisting of: a drug coating, an anticoagulant drug coating, and a wetting agent to improve aqueous humor flow within the arcuate scaffold.

6. The aqueous humor outflow device of claim 1, wherein the first and second arcuate rails and the plurality of structural components frame one or more openings through which to receive the aqueous humor from the trabecular meshwork and to allow the flow of the aqueous humor through the arcuate scaffold to the one or more collector channels when inserted in the Schlemm's canal.

7. The aqueous humor outflow device of claim 6, wherein the one or more openings through which to receive the aqueous humor from the trabecular meshwork are exposed to an anterior chamber of the mammalian eye by a trabeculotomy created when or after the arcuate scaffold is fitted within the conventional aqueous humor outflow pathway of the mammalian eye.

8. The aqueous humor outflow device of claim 1,
wherein the first and second arcuate rails and their respective anterior and posterior edges define a first cross-sectional area in a plane normal to a longitudinal axis of the arcuate scaffold;
wherein a cross section of at least one of the plurality of structural components defines a second cross-sectional area in the plane normal to the longitudinal axis of the arcuate scaffold less than the first cross-sectional area;
wherein a difference between the first cross-sectional area and the second cross-sectional area defines an open area; and
wherein the arcuate scaffold allows flow of the aqueous humor through the open area in a direction generally along the longitudinal axis of the arcuate scaffold when inserted in the Schlemm's canal.

9. The aqueous humor outflow device of claim 8, wherein the first cross-sectional area in the plane normal to the longitudinal axis of the arcuate scaffold is greater than a cross-sectional area of the Schlemm's canal in its natural resting state.

10. The aqueous humor outflow device of claim 8, wherein the arcuate scaffold allows flow of the aqueous humor through the open area in a direction generally along the longitudinal axis of the arcuate scaffold within and between a plurality of chambers of the Schlemm's canal to the one or more collector channels that originate in the posterior wall of the Schlemm's canal when inserted in the Schlemm's canal.

11. The aqueous humor outflow device of claim 10,
wherein the trabecular meshwork abuts at least one of the openings framed by the first and second arcuate rails and the plurality of structural components; and
wherein the openings framed by the first and second arcuate rails and the plurality of structural components allow the trabecular meshwork, to stretch into at least one of the openings to facilitate the flow of aqueous humor from a first to a second of the plurality of chambers of the Schlemm's canal in a direction generally along the longitudinal axis of the arcuate scaffold within and between chambers of the Schlemm's canal to the one or more collector channels.

12. The aqueous humor outflow device of claim 10, wherein a pressure differential between two adjacent chambers of the plurality of chambers is sufficient to force the posterior wall of Schlemm's canal away from a posterior edge of the structural component there between to open a membrane valve formed by the posterior wall of Schlemm's canal and the posterior edge of the structural component allowing flow of aqueous humor from one of the adjacent chambers to the other of the adjacent chambers along the posterior wall of Schlemm's canal.

13. The aqueous humor outflow device of claim 10, wherein the flow of aqueous humor along the posterior wall of Schlemm's canal causes a shear stress on a plurality of endothelial cells that line the posterior wall of Schlemm's canal.

14. The aqueous humor outflow device of claim 1, wherein the plurality of structural components each comprises:
a first face coupled to the first arcuate rail;
a second face coupled to the second arcuate rail;
an anterior face having respective edges that meet at the anterior edges of the first and second arcuate rails; and
a posterior face having at least a portion of the posterior face that is recessed with respect to at least one of the posterior edges of the first and second arcuate rails.

15. The aqueous humor outflow device of claim 14, wherein the posterior face that is recessed with respect to at least one of the posterior edges of the first and second arcuate rails comprises a posterior face with at least one edge that is recessed with respect to at least one of the posterior edges of the first and second arcuate rails.

16. The aqueous humor outflow device of claim 14, wherein the anterior face of at least one of the plurality of structural components is posteriorly recessed.

17. The aqueous humor outflow device of claim 1, wherein the arcuate scaffold has a first end shaped as one of:
a polyhedron having a polygon base; and
a cone having a base of any shape, the base in a plane substantially normal to the longitudinal axis of the arcuate scaffold; and
wherein the polyhedron or cone having a side extending along the longitudinal axis of the arcuate scaffold and converging toward an apex of the polyhedron or cone located outside a plane of the base.

18. The aqueous humor outflow device of claim 17, wherein the apex comprises a hole or opening through which to allow flow of aqueous humor to or from one of: the Schlemm's canal, one of the plurality of collector channels, and a device positioned adjacent to, abutting, or docked with the aqueous humor outflow device.

19. The aqueous humor outflow device of claim 17, wherein the arcuate scaffold has a second end shaped as one of:
a polyhedron having a polygon base; and
a cone having a base of any shape, the base in a plane substantially normal to the longitudinal axis of the arcuate scaffold; and
wherein the second end's polyhedron or cone having a side extending along the longitudinal axis of the arcuate scaffold and converging toward an apex of the second end's shaped polyhedron or cone located outside a plane of the base.

20. The aqueous humor outflow device of claim 19, wherein the apex of the second end's shaped polyhedron or cone comprises a hole or opening through which to allow flow of aqueous humor to or from one of: the Schlemm's canal, one of the plurality of collector channels, and a device positioned adjacent to, abutting, or docked with the aqueous humor outflow device.

21. The aqueous humor outflow device of claim 1, wherein the first and second arcuate rails and the plurality of structural components that frame the one or more openings, or a tip of or hole in a first or second end of the device, provide a port within which to retain an implant device in a stable position.

22. The aqueous humor outflow device of claim 21, wherein the implant device is selected from a group of implant devices consisting of: an ocular support device to support or attach to other natural or synthetic structures within the eye, such as an intraocular lens, an iris or iris prosthesis, an iris clip/hook, a capsular bag or capsular bag support device; and a non-ocular support device, such as a drug eluting device, a drug delivery device, a fluid delivery device, a sensor device, a transducer device, a gene/vector delivery device, a trabecular microbypass device, an intrascleral implant, a suprachoroidal/supraciliary implant, an ultrasound signal emitting device, a radio frequency signal emitting device, and an electromagnetic wave emitting device.

23. The aqueous humor outflow device of claim 1, wherein the respective anterior edges of the first and second arcuate rails provide a guide between which to insert an implant device.

24. The aqueous humor outflow device of claim 23, wherein the first and second arcuate rails flex to allow insertion of the implant device.

25. The aqueous humor outflow device of claim 23, wherein respective posterior edges of the first and second arcuate rails are recessed at a location that is opposite a location of the respective anterior edges of the first and second arcuate rails into which the implant device is inserted.

26. The aqueous humor outflow device of claim 1, further comprising an implant device removably positioned within the first and second arcuate rails.

27. The aqueous humor outflow device of claim 26, wherein the implant device is held in place at least in part by pressure provided by the trabecular meshwork.

28. The aqueous humor outflow device of claim 1, wherein the arcuate scaffold further comprises a non-tapered end into which a tapered end or a non-tapered end of a second arcuate scaffold is inserted.

* * * * *